United States Patent [19]
Danishefsky et al.

[11] Patent Number: 6,020,341
[45] Date of Patent: Feb. 1, 2000

[54] ENEDIYNE QUINONE IMINES AND METHODS OF PREPARATION AND USE THEREOF

[75] Inventors: Samuel J. Danishefsky, Englewood, N.J.; Matthew D. Shair, Somerville, Mass.; Taeyoung Yoon, East Haven, Conn.; Ting-Chao Chou, Paramus, N.J.; Karoline K. Mosny, Somerville, Mass.

[73] Assignee: Sloan-Kettering Institute for Cancer Research, New York, N.Y.

[21] Appl. No.: 08/849,658

[22] PCT Filed: Dec. 1, 1995

[86] PCT No.: PCT/US95/15678

§ 371 Date: Oct. 16, 1997

§ 102(e) Date: Oct. 16, 1997

[87] PCT Pub. No.: WO96/16655

PCT Pub. Date: Jun. 6, 1996

Related U.S. Application Data

[63] Continuation-in-part of application No. 08/347,952, Dec. 1, 1994, Pat. No. 5,622,958.

[51] Int. Cl.$^7$ .......................... A61K 31/47; C07D 221/18
[52] U.S. Cl. .............................................. 514/280; 546/47
[58] Field of Search ................................ 514/280; 546/47

[56] References Cited

U.S. PATENT DOCUMENTS

| | | | |
|---|---|---|---|
| 5,276,159 | 1/1994 | Smith et al. | 548/147 |
| 5,281,710 | 1/1994 | Smith et al. | 546/18 |

OTHER PUBLICATIONS

Hinman, L.M. and Yarranton, G., "New Approaches to Non–Immunogenic Monoclonal Antibody Cancer Therapies," *Ann. Repts. Med. Chem.*, 1993, 237–246.

Konishi, M., et al., "Dynemicin A, A Novel Antibiotic with the Anthraquinone and 1,5–Diyn–3–ene Subunit," *J. Antiobiot.*, 1989, 42(9): 1449–1452.

Myers, A.G., et al., "Highly Convergent Route to Dynemicins of Wide Structural Variability. Enantioselective Synthesis of Quinone Imine Precursors to Natural and Nonnatural Dynemicins," *J.Amer. Chem. Soc.*, 1994, 116: 11556–11557.

Nicolaou, K.C., and Dai, W.–M., "Chemistry and Biolgy of the Enediyne Anticancer Antibiotics," *Angew. Chem. Int. Ed. Engl.*, 1991, 30(11): 1387–1416.

Nicolau, K.C., et al., "Designed Enediynes: A New Class of DNA–Cleaving Molecules with Potent and Selective Anticancer Activity," *Science*, 1992, 256: 1172–1178.

Semmelhack, M.F., and Gallagher, J.J., "THe Effect on DNA Cleavage Potency of Tethering A Simple Cyclic Enediyne to a Netropsin Analog," *J. Org. Chem.*, 1994, 59: 4357–4359.

Shair M.D., et al., "Enediyne Quinone Imines: Truncated, Biologically Active Dynemicin Congeners," *Angew. Chem. Int. Ed. Engl.*, 1994, 33(23/24): 2477–2479.

Shair, M.D., et al., "A Remarkable Cross Coupling Reaction to Construct the Enediyne Linkage Relevant to Dynemicin A: Synthesis of the Deprotected ABC System," *J. Org. Chem.*, 1994, 59(14): 3755–3757.

Trail, P.A., et al., "Cure of Xenografted Human Carcinomas by BR96–Doxorubicin Immunoconjugates," *Science*, 1993, 261: 212–215.

Wender, P.A., et al., "A Photochemically Triggered DNA Cleaving Agent: Synthesis, Mechanistic and DNA Cleavage Studies on a New Analog of the Antitumor Antibiotic Dynemicin," *J. Org. Chem.*, 1993, 53(22): 5867–5869.

Yoon, T., Ph.D. Dissertation, Yale University, "Part 1 Synthetic Studies Towards Dynemicin A," May 25, 1994, pp. 23–31, and 57–63.

(List continued on next page.)

*Primary Examiner*—Mukund J. Shah
*Assistant Examiner*—Brenda Coleman
*Attorney, Agent, or Firm*—John P. White; Cooper & Dunham LLP

[57] ABSTRACT

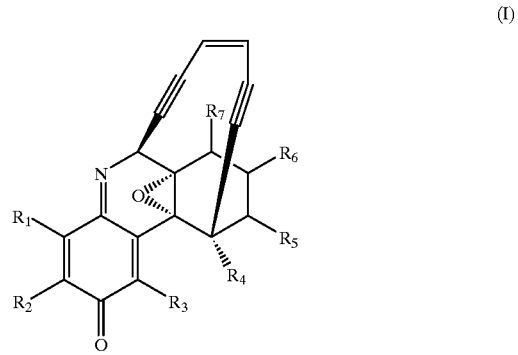

A quinone imine enediyne possessing cytotoxic activity towards cancer cells having general structure (I) wherein $R_1$, $R_2$ and $R_3$ are independently the same or different and are H, Br, Cl, F, $NH_2$, $CO_2H$, OH, linear or branched alkyl, etc.; wherein $R_4$ is H, OH or linear or branched alkoxy, linear or branched alkoxycarbonyl, etc.; wherein $R_5$ is H, Br, Cl, F, O=, OH or S—SR, or linear or branched alkyl, etc.; wherein $R_6$ is H, Br, Cl, F, $CO_2H$, OH or S—SR', or linear or branched alkyl, etc.; wherein $R_7$ is H, OH or S—SR", or linear or branched alkyl, linear or branched alkoxycarbonyl, linear or branched alkoxy or linear or branched hydroxyalkyl; and wherein R, R' and R" are independently the same or different and are linear or branched alkyl, linear or branched acyl or linear or branched alkoxyalkyl. Also provided are conjugates of the compound with cleavable peptides, enzymes, carbohydrates and monoclonal antibodies immunoreactive with cancer cells, as well as compositions comprising the analogues and conjugates, and methods of synthesis and treatment of tumors.

6 Claims, 12 Drawing Sheets

OTHER PUBLICATIONS

Yoon, T., et al., "Experiments Directed Toward a Total Synthesis of Dynemicin A: A Solution to the Stereochemical Problem," J. Org. Chem., 1994, 59(14): 3752–3757.

Myers, et al., Chemical Abstract, vol. 121, Abstract No. 280,446 (1995).

Chem. & Eng. News, Jan. 23, 1995, p. 22.

Chemical Abstract Registry Nos. 158818–85–0 and 158818–83–8, available Nov. 8, 1994.

18: X = Oα
19: X = Oβ

ENEDIYNE QUINONE IMINES AND METHODS OF PREPARATION AND USE THEREOF

This application ia a national stage entry under 35 U.S.C. 371 filed Dec. 1, 1995 which is a continuation-in-part of U.S. Ser. No. 08/347,952, filed Dec. 1, 1994, now U.S. Pat. No. 5,622,958 the contents of which are incorporated by reference into this application.

The invention described herein was made in the course of work under Grant Number CA28824 from the National Institutes of Health, U.S. Department of Health and Human Services. The U.S. Government may have certain rights in this invention.

BACKGROUND OF THE INVENTION

This invention relates to enediyne quinone imines, compounds useful for the treatment of cancer, conjugates thereof with peptides, enzymes, carbohydrates, and monoclonal antibodies, and to methods of preparing and using them.

The novel enediyne antibiotic dynemicin A (1) (Konishi, M.; Ohkuma, H.; Matsumoto, K.; Tsuno, T.; Kamei, H.; Miyaki, T.; Oki, T.; Kawaguchi, H.; Van Duyne, G. D.; Clardy, J. *J. Antibiot.*, 1989, 42, 1449. Konishi, M.; Ohkuma, H.; Tsuno, T.; Oki, T.; VanDuyne, G. D.; Clardy, J. *J. Am. Chem. Soc.*, 1990, 112, 3715) has stimulated the pursuit of DNA cleavage studies (Sugiura, Y.; Shiraki, T.; Konishi, M.; Oki, T. *Proc. Nat. Acad. Sci. U.S.A.*, 1990, 87, 3831), the design of new pro-drug constructs and the development of novel methodology directed at total synthesis. Nicolaou, K. C.; Dai, W.-M. *Angew. Chem. Int. Ed. Enql.*, 1991, 30 1387; Taunton, J.; Wood, J. L.; Schreiber, S. L. *J. Am. Chem. Soc.*, 1993, 115, 10378. The prevailing assumption (Semmelhack, M. F.; Gallagher, J.; Cohen, D. *Tetrahedron Lett.*, 1990, 31, 1521; Sugiura, Y.; Shiraki, T.; Konishi, M.; Oki, T. *Proc. Nat. Acad. Sci. U.S.A.*, 1990, 87, 3831) concerning the ignition mechanism for the drug to operate as a diyl precursor presupposes reduction of the quinone ring to the hydroquinone state. In this way the "lone pair" on nitrogen is unleashed to participate in mediating solvent attack on the epoxide (Scheme 1, see arrows). The opening of this epoxide is a critical prophase in fostering the Bergman (enediyne →1,4-diyl) transformation. Jones, R. R.; Bergman, R. G. *J. Am. Chem. Soc.*, 1972, 94, 660. Bergman, R. G.; *Acc. Chem. Res.*, 1973, 6, 25. The cytotoxicity of enediyne antibiotics is thought to arise from the DNA cutting tendency of diyl 2 or its quinone counterpart. Sugiura, Y.; Shiraki, T.; Konishi, M.; Oki, T. *Proc. Nat. Acad. Sci. U.S.A.*, 1990, 87, 3831. The dihydroxy naphthaquinone sector presumably provides noncovalent intercalative contacts for directing the drug to its oligonucleotide target. Sugiura, Y.; Shiraki, T.; Konishi, M.; Oki, T. *Proc. Nat. Acad. Sci. U.S.A.*, 1990, 87, 3831; Arcamone, F. in *Doxorubicin Anticancer Antibiotics*, Academic, New York, 1981; Neidle, S.; Pearl, L. H.; Skelly, J. V. *Biochem. J.*, 1987, 243, 1–13; Wang, A.; Ughetto, G.; Quigley, G.; Rich, A. *Biochemistry*, 1987, 26, 1152. The present invention provides new analogues of enediyne antibiotics and methods of preparing and using them, and offers a potentially important advance for cancer chemotherapy.

SUMMARY OF THE INVENTION

The subject invention provides a compound having the structure:

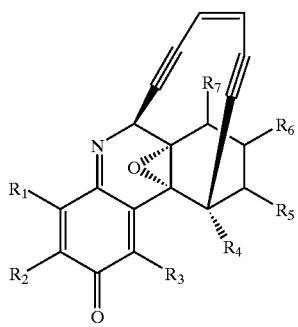

wherein $R_1$, $R_2$ and $R_3$ are independently the same or different and are H, Br, Cl, F, $NH_2$, $CO_2H$, or OH or a linear or branched alkyl, linear or branched acylamino, linear or branched acyloxy, linear or branched alkoxy-carbonyl, linear or branched alkoxy, aryloxy, linear or branched alkylaryl, linear or branched hydroxyalkyl, linear or branched aminoalkyl or aryl group; wherein $R_4$ is H, OH or a linear or branched alkoxy, linear or branched alkoxycarbonyl, linear or branched acyloxy or aryloxy group; wherein $R_5$ is H, Br, Cl, F, O=, OH or S—SR, or a linear or branched alkyl, aryl, linear or branched alkylaryl, linear or branched alkoxy, linear or branched acyloxy or linear or branched hydroxyalkyl group; wherein $R_6$ is H, Br, Cl, F, $CO_2H$, OH or S—SR', or a linear or branched alkyl, aryl, linear or branched alkylaryl, linear or branched alkoxycarbonyl, linear or branched alkoxy or linear or branched hydroxyalkyl group; wherein $R_7$ is H, OH or S—SR", or a linear or branched alkyl, linear or branched alkoxycarbonyl, linear or branched alkoxy or linear or branched hydroxyalkyl group; and wherein R, R' and R" are independently the same or different and are a linear or branched alkyl, linear or branched acyl or linear or branched alkoxyalkyl group.

The subject invention also provides a pharmaceutical composition comprising a therapeutically effective amount of the compound having the structure above dissolved or suspended in a pharmaceutically acceptable carrier.

The subject invention further provides a process of synthesizing a compound having the structure shown above.

The subject invention also provides a process of synthesizing an enediyne quinone imine having the structure:

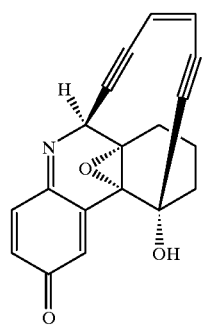

In addition, the subject invention provides a conjugate which comprises a compound and a monoclonal antibody, wherein the compound is covalently bonded to the monoclonal antibody, and the compound has the structure shown above; wherein the monoclonal antibody is immunoreactive with a determinant site of a cell surface antigen of human tumor cells; wherein the compound is covalently bonded via a cleavable linker connecting suitable functional groups, respectively, of the compound and the monoclonal antibody; and wherein the cleavable linker is selected from a group consisting of glutarate, N-hydroxysuccinic amide ester, a peptide, monosaccharide, oligosaccharide, thioether, disulfide, trisulfide, hydrazide and hydrazone moieties.

The subject invention further provides a conjugate which comprises a compound constituting an aglycone moiety and an oligosaccharide moiety, wherein the compound is covalently bonded to the oligosaccharide moiety, and the compound has the structure above; wherein the aglycone moiety is covalently bonded via a glycosidic linkage through one of $R_1$, $R_2$, $R_3$, $R_4$, $R_5$, $R_6$ and $R_7$ being a hydroxyl group or a linear hydroxyalkyl group; and wherein the oligosaccharide moiety comprising one or more sugar units selected from the group consisting of glucosyl, ribosyl, fucosyl, galactosyl, deoxyribosyl and an acylated aminosugar.

The subject invention also provides a conjugate for use as a prodrug in conjunction with a covalently bonded monoclonal antibody-enzyme complex which comprises a compound and a substrate for the enzyme, wherein the compound is covalently bonded to the substrate for the enzyme, and the compound has the structure above; wherein the monoclonal antibody is immunoreactive with a determinant site of a cell surface antigen of human tumor cells; wherein the substrate is a specific substrate of the enzyme, and is bonded to the compound via linking atoms; and wherein the linking atoms comprise side-chain functional groups of the compound.

The subject invention further provides a method of treating tumors in a subject which comprises administering to the subject a therapeutically effective amount of any one of the compounds disclosed hereinabove.

BREIF DESCRIPTION OF THE FIGURES

A more complete understanding of the invention will become apparent by reference to the detailed description which follows when considered in conjunction with the accompanying figures wherein.

Figure 4A:
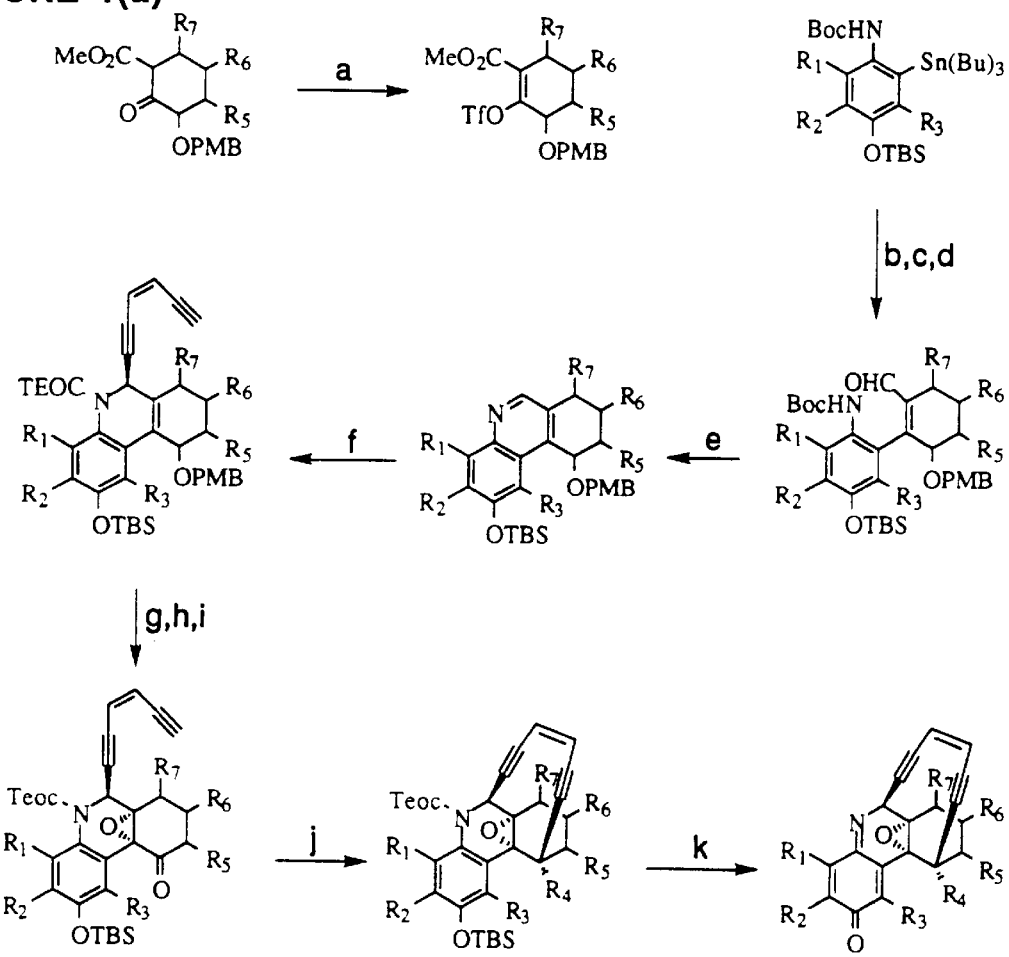
FIG. 4(a) illustrates the general preparation of quinone imine enediynes 6. a) $Tf_2O$, Pyridine, $CH_2Cl_2$; b) $Pd_2(dba)_3$, PhH; c) DibalH, $CH_2Cl_2$, $-78°$ C.; d) $MnO_2$, $CH_2Cl_2$; e) TFA, $CH_2Cl_2$; f) BrMgCCCHCHCCMgBr, TeocCl; g) mCPBA, $CH_2Cl_2$; h) DDQ, $H_2O$, $CH_2Cl_2$; i) PDC, $CH_2Cl_2$; j) LDA, THF, $-78°$ C.; k) TBAF, THF then PhI(OAc)$_2$.
Figure 4B:
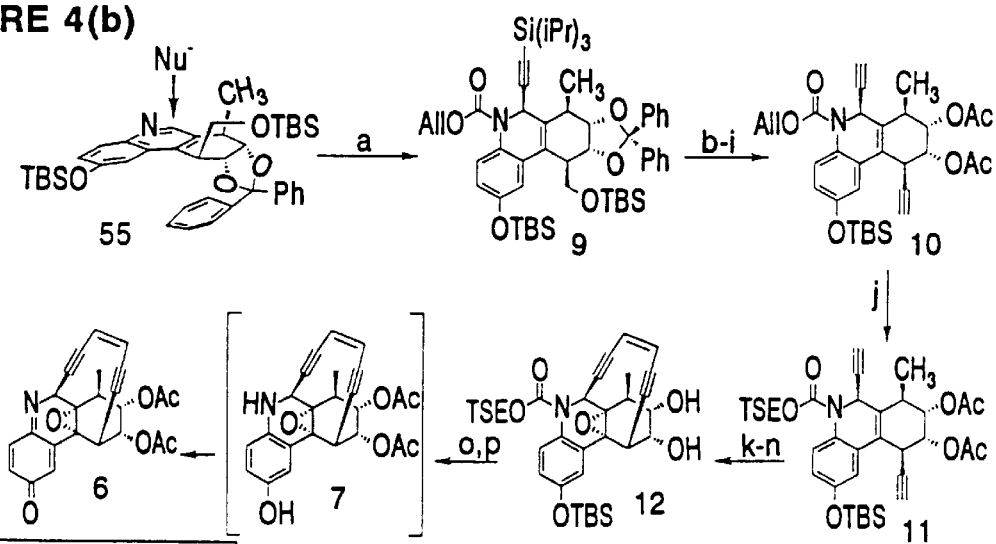

FIG. 4(b) illustrates the preparation of quinone imine enediyne 6. a) (TIPS)ethynylmagnesiumbromide, $ClCO_2All$, THF, $-20°$ C. (75%); b) conc. HCl, 1 eq., THF (90%); c) (COCl)$_2$, DMSO, Et$_3$N, $-78°$ C. (95%); d) Ph$_3$P, CBr$_4$, $CH_2Cl_2$ (90%); e) n-BuLi, toluene, $-78°$ C. (81%); f) TBAF, THF; g) conc. HCl, MeOH; h) NaH, TBSCl; i) Ac$_2$O, Pyr, DMAP, $CH_2Cl_2$ (60% overall); j) Pd(Ph$_3$P)$_4$, morpholine, THF, then NaH, TEOCl (90%); k) NH$_2$NH$_2$, THF-MeOH (100%); l) mCPBA, $CH_2Cl_2$ (80%); m) AgNO$_3$, NIS, THF (93%); n) 4, Pd(Ph$_3$P)$_4$, DMF, 70° C. (80%); o) Ac$_2$O, Pyr, DMAP, $CH_2Cl_2$ (96%); p) TBAF, THF, 0° C., 3 h, then PhI(OAc)2 (60%).

Figure 5:
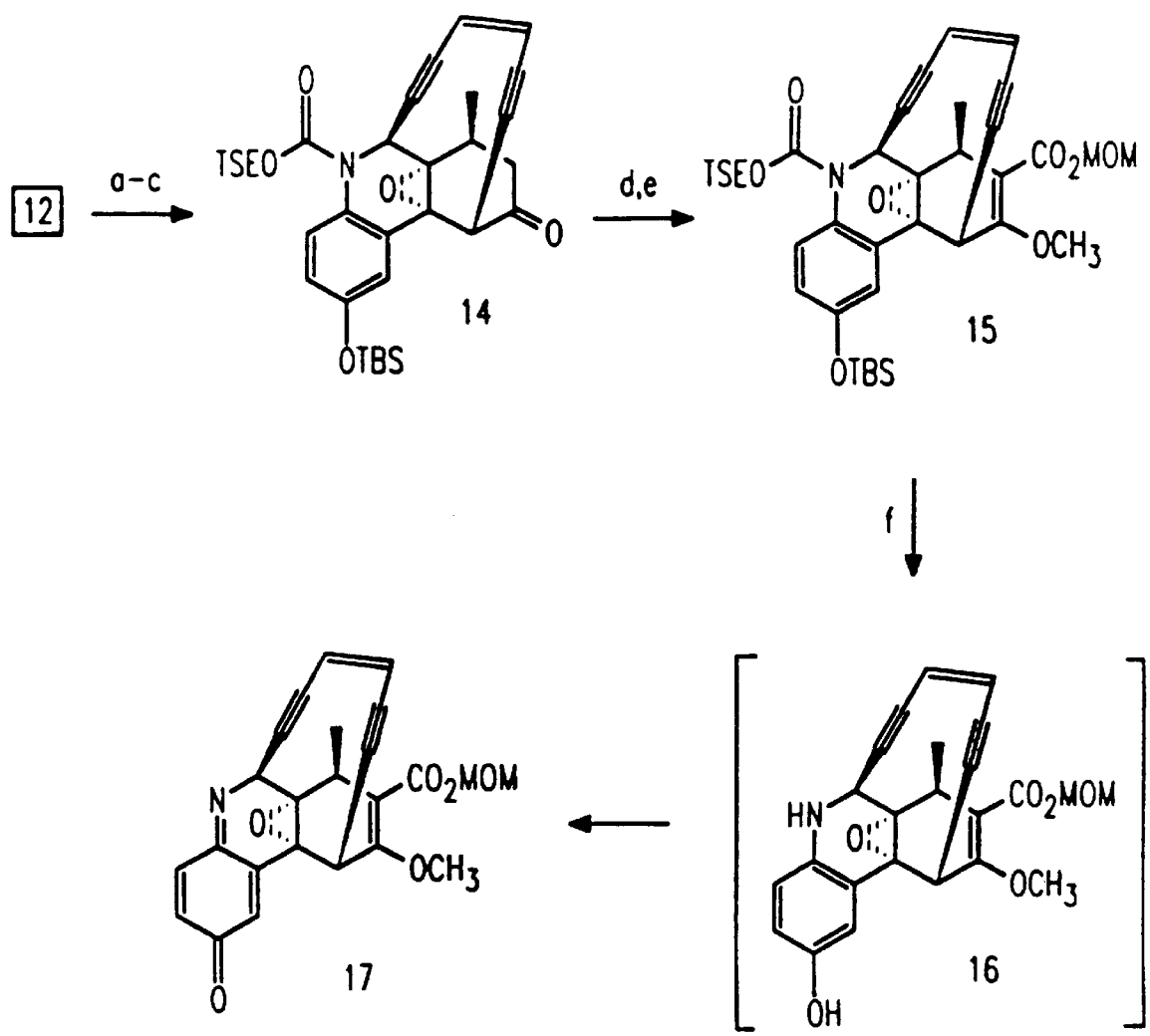

FIG. 5 illustrates the preparation of an elaborated quinone imine enediyne. a) $Tf_2O$, $CH_2Cl_2$, $-20°$ C. (94%); b) Dess-Martin periodinate, $CH_2Cl_2$, r.t. (93%); c) $CrCl_2$, THF, rt (89%); d) MgBr$_2$, CO$_2$, Et$_3$N, CH$_3$CN then MOMCl, iPr$_2$NEt (31%, 70% based on recovered 14); e) TMSCHN$_2$, MeOH (80%); f) TBAF, THF, 0° C. then PhI(OAc)$_2$ (58%).

Figure 6:
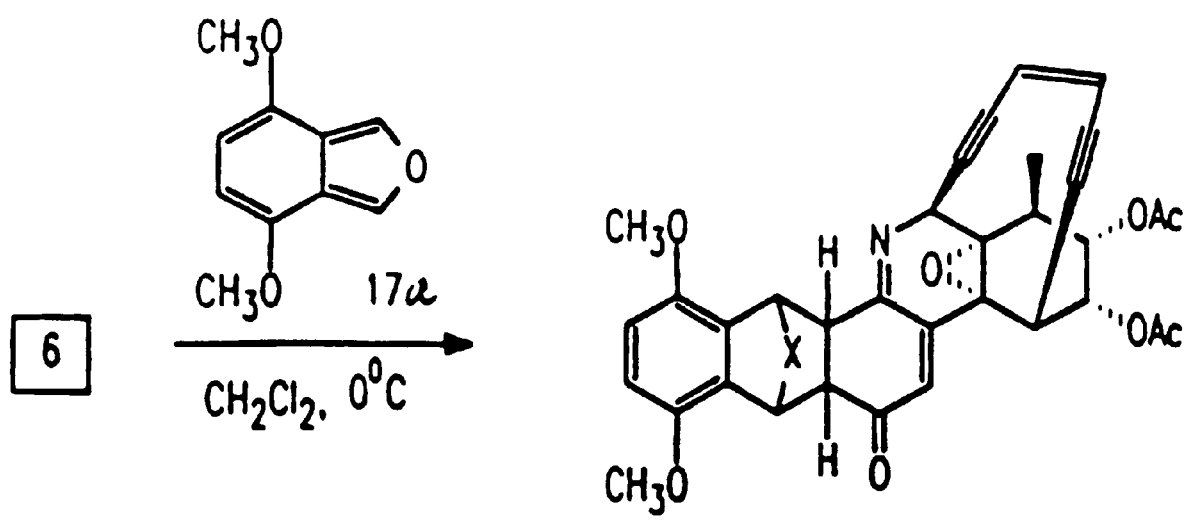

FIG. 6 illustrates the cycloaddition of quinone imine enediyne 6 with isobenzofuran 17a.

Figure 7:
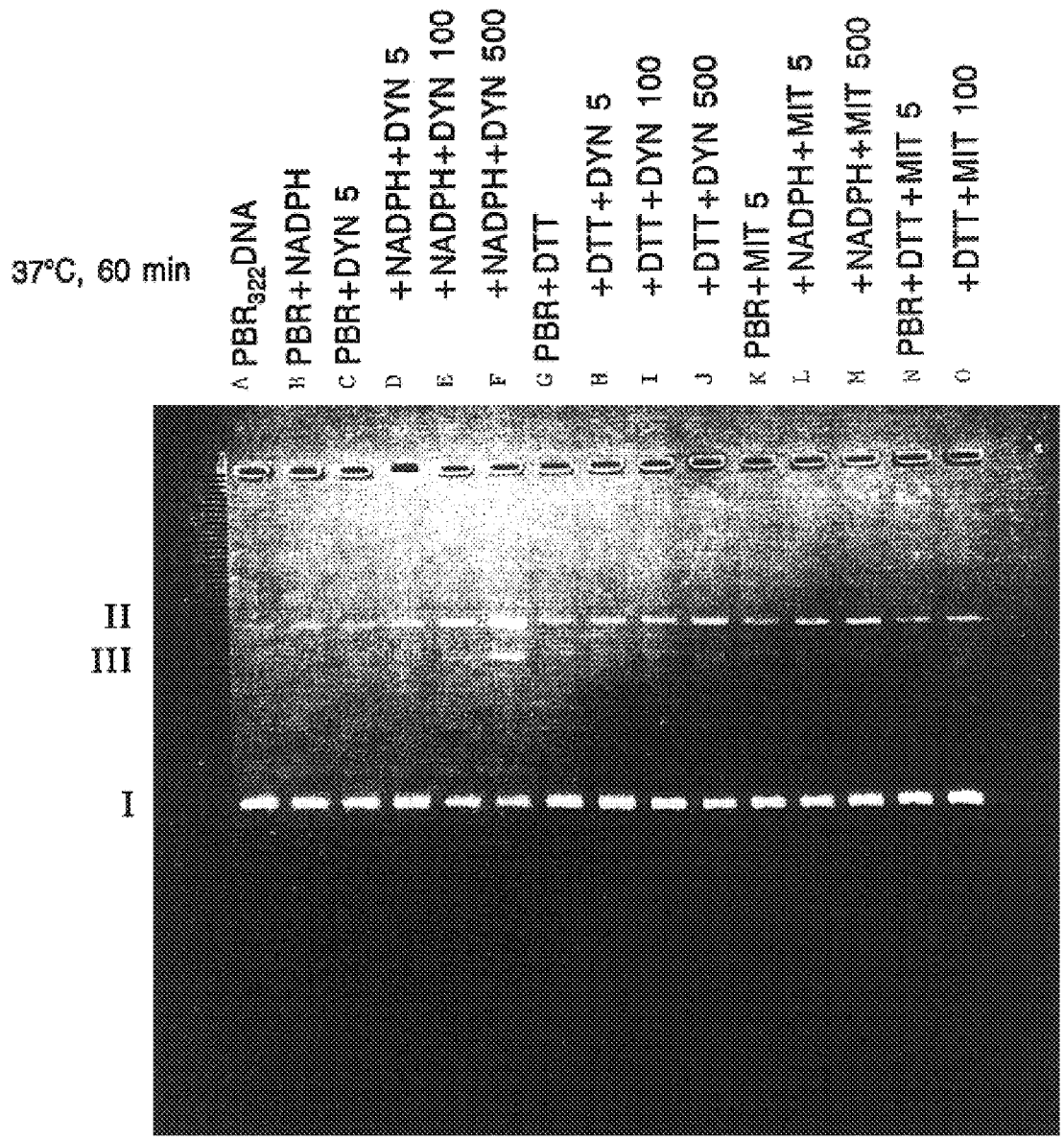

FIG. 7 illustrates interaction of supercoiled DNA with quinone imine 6 (DYN) and mitomycin C (MIT) at concentrations indicated ($\mu$M). Lane I=supercoiled DNA; Lane II=nicked DNA (single-stranded cleavage); Lane III=linear DNA (double-stranded cleavage). PBR$_{322}$ DNA was incubated in Tris-HCl buffer, pH 7.5 for 60 min at 37° C. in the presence and absence of 5 mM of reducing agent, NADPH or dithiothreitol (DTT). The reaction mixtures were analyzed by electrophoresis (1 percent agarose gel, ethidium bromide stain).

Figure 8:
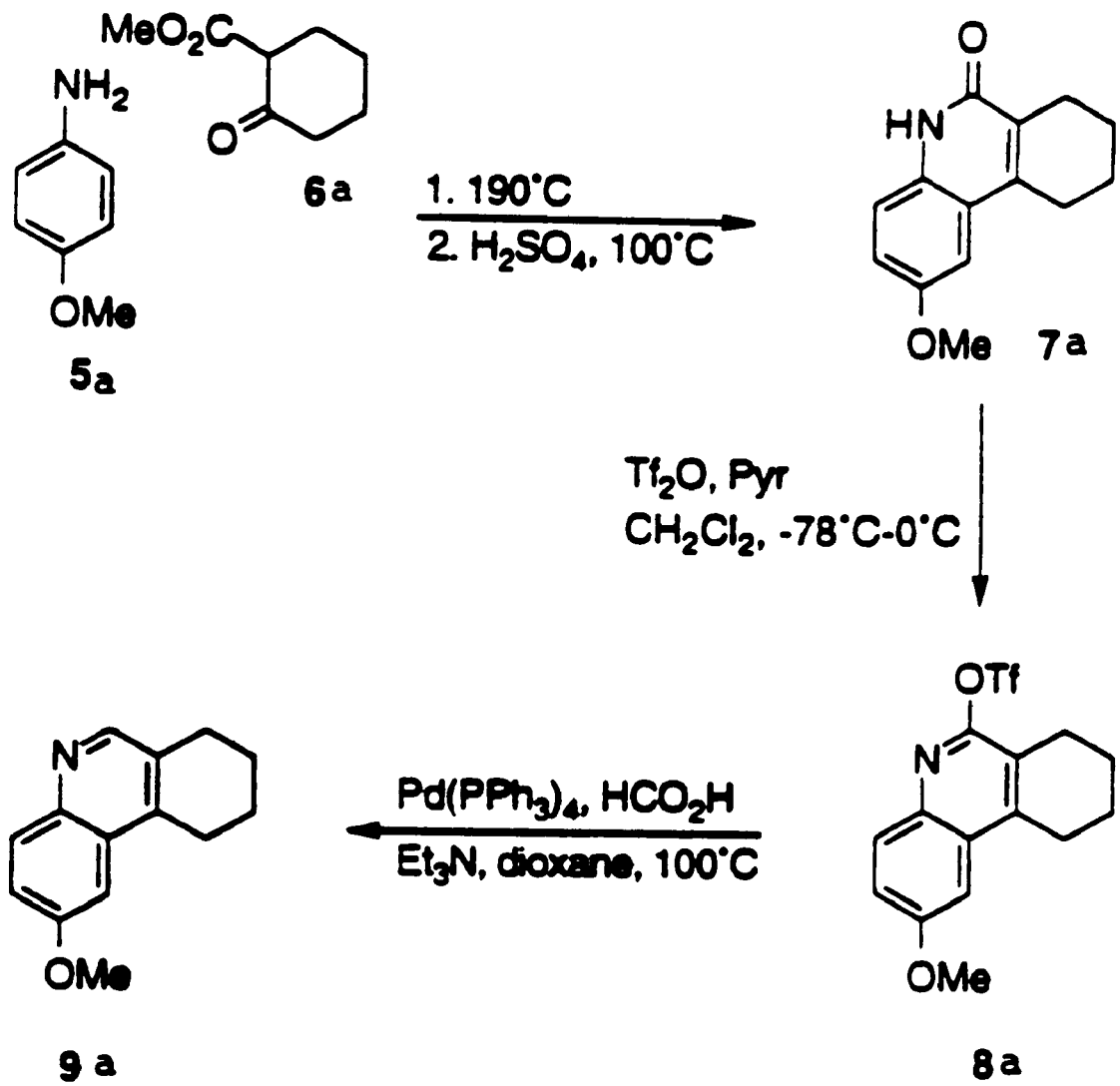
Figure 9:
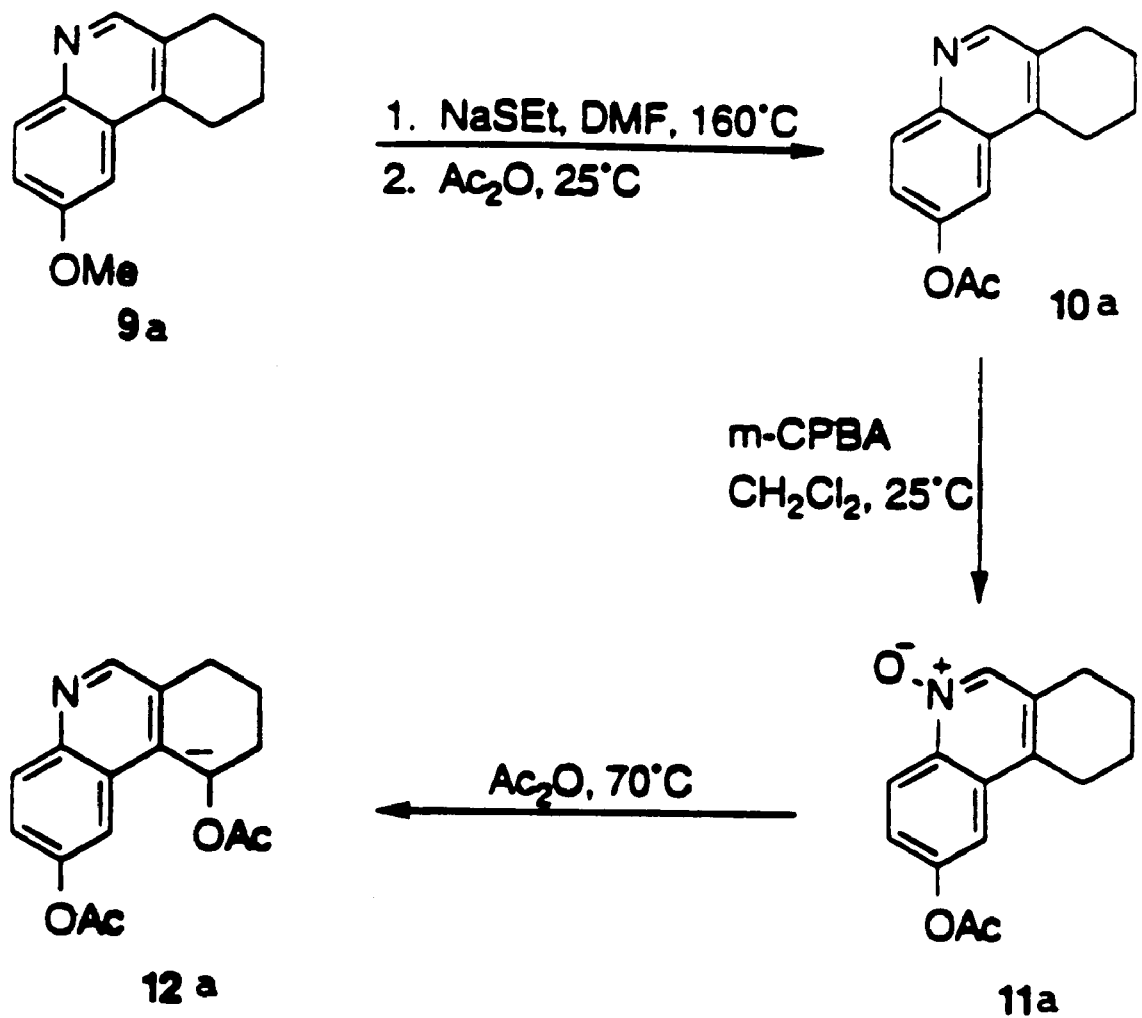
Figure 10:
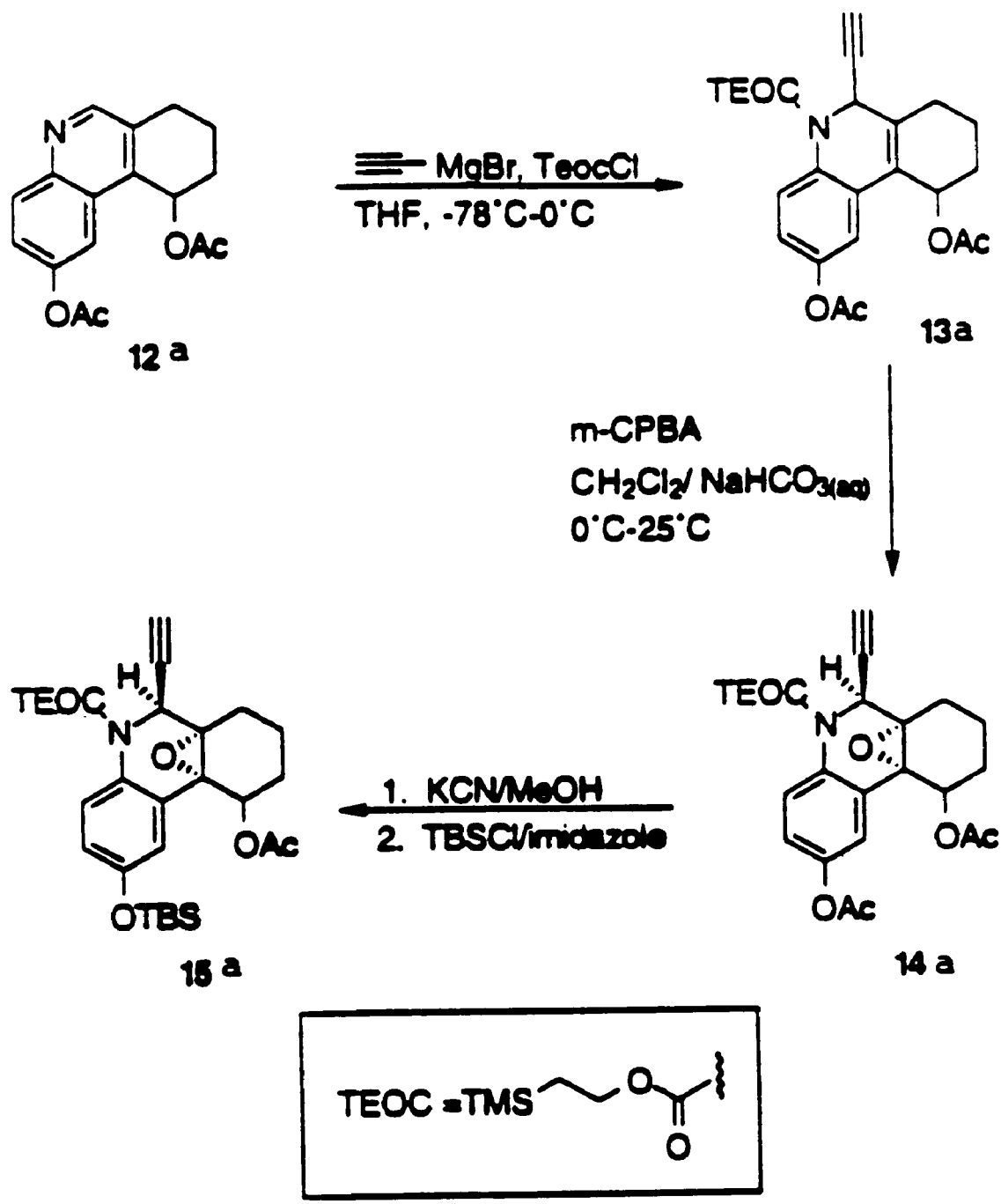
Figure 11:
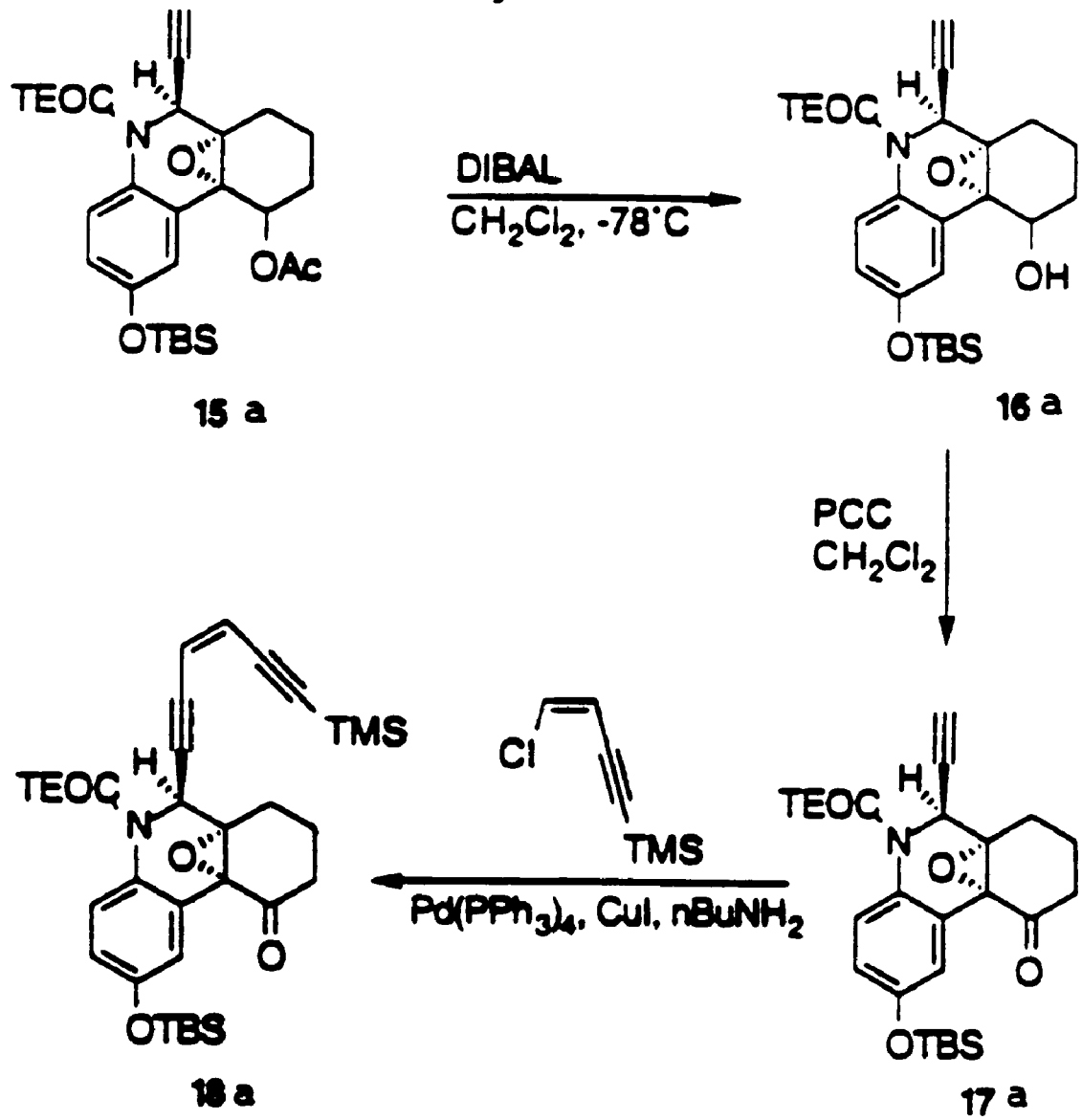
Figure 12:
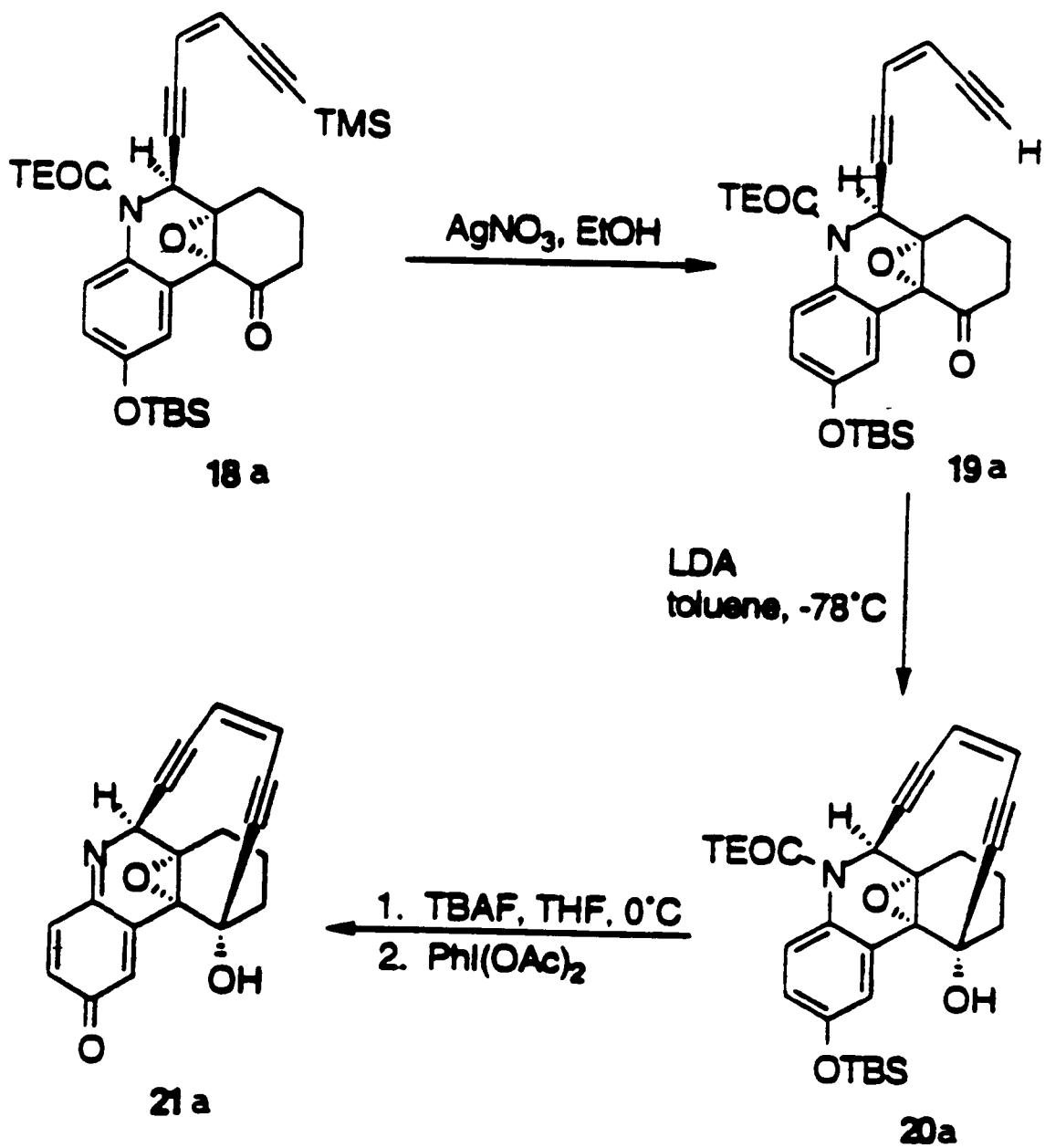

FIG. 8 illustrates the synthesis of intermediate 9a.
FIG. 9 illustrates the synthesis of intermediate 12a.
FIG. 10 illustrates the synthesis of intermediate 15a.
FIG. 11 illustrates the synthesis of intermediate 18a.
FIG. 12 illustrates the synthesis of intermediate 21a.

DETAILED DESCRIPTION OF THE INVENTION

The subject invention provides a compound having the structure:

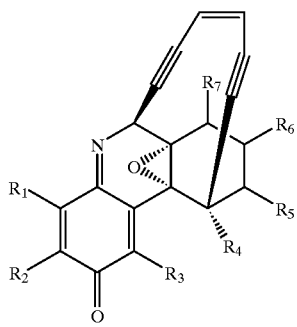

wherein $R_1$, $R_2$ and $R_3$ are independently the same or different and are H, Br, Cl, F, NH$_2$, CO$_2$H, OH, linear or branched alkyl, linear or branched acylamino, linear or branched acyloxy, linear or branched alkoxycarbonyl, linear or branched alkoxy, aryloxy, linear or branched alkylaryl, linear or branched hydroxyalkyl, linear or branched aminoalkyl or aryl; wherein $R_4$ is H, OH, linear or branched alkoxy, linear or branched alkoxycarbonyl, linear or branched acyloxy or aryloxy; wherein $R_5$ is H, Br, Cl, F, O=, OH, S—SR, linear or branched alkyl, aryl, linear or branched alkylaryl, linear or branched alkoxy, linear or branched acyloxy or linear or branched hydroxyalkyl; wherein $R_6$ is H, Br, Cl, F, CO$_2$H, OH, S—SR', or linear or branched alkyl, aryl, linear or branched alkylaryl, linear or branched alkoxycarbonyl, linear or branched alkoxy or linear or branched hydroxyalkyl; wherein $R_7$ is H, OH, S—SR", or linear or branched alkyl, linear or branched alkoxycarbonyl, linear or branched alkoxy or linear or branched hydroxyalkyl; and wherein R. R' and R" are independently the same or different and are linear or branched alkyl, linear or branched acyl or linear or branched alkoxyalkyl. In a certain embodiment, the subject invention provides the compound, wherein $R_2$, $R_3$ and $R_4$ are H. In another embodiment, the subject invention further provides the compound, wherein $R_2$, $R_3$ and $R_4$ are H, and $R_7$ is a linear alkyl group. In another embodiment, the invention provides the compound, wherein $R_2$, $R_3$ and $R_4$ are H, and $R_7$ is $CH_3$. In another embodiment, the invention further provides the compound, wherein $R_2$, $R_3$ and $R_4$ are H, $R_7$ is a linear alkyl group, and $R_5$ and $R_6$ are independently the same or different and are selected from the group consisting of a linear hydroxyalkyl group, a linear alkoxycarbonyl group and OH. In another embodiment, the invention also provides the compound, wherein $R_2$, $R_3$ and $R_4$ are H, $R_7$ is a $CH_3$, and $R_5$ and $R_6$ are independently the same or different and are selected from the group consisting of a linear hydroxyalkyl group, a linear alkoxycarbonyl group and OH. In another embodiment, the invention additionally provides the compound, wherein $R_2$, $R_3$ and $R_4$ are H, $R_7$ is a $CH_3$, and $R_5$ and $R_6$ are both OH. In another embodiment, the invention provides the compound, wherein R1 is selected from a group consisting of a linear acylamino group, a linear aminoalkyl group and $NH_2$, $R_2$, $R_3$ and $R_4$ are H, $R_7$ is a $CH_3$, and $R_5$ and $R_6$ are both OH. In another embodiment, the invention provides the compound, wherein R1 is $NH_2$, $R_2$, $R_3$ and $R_4$ are H, $R_7$ is a $CH_3$, and $R_5$ and $R_6$ are both OH. In a another embodiment, the invention provides the compound, wherein $R_2$, $R_3$ and $R_4$ are H, and R1 is $NH_2$. In a certain other embodiment, the invention provides a compound, wherein $R_2$, $R_3$ and $R_4$ are H, and wherein $R_6$ is H. In another embodiment, the invention provides a compound, wherein $R_2$, $R_3$ and $R_4$ are H, wherein $R_6$ is H, and wherein $R_7$ is a linear alkyl group. In another embodiment, the invention further provides a compound, wherein $R_2$, $R_3$ and $R_4$ are H, wherein $R_6$ is H, and wherein $R_7$ is $CH_3$. In another embodiment, the invention also provides a compound, wherein $R_2$, $R_3$ and $R_4$ are H, wherein $R_6$ is H, wherein $R_7$ is a linear alkyl group, and wherein $R_5$ is selected from the group consisting of a linear hydroxyalkyl group, a linear alkoxycarbonyl group and OH. In another embodiment, the invention additionally provides a compound, wherein $R_2$, $R_3$ and $R_4$ are H, wherein $R_6$ is H, wherein $R_7$ is a linear alkyl group, and wherein $R_5$ is OH. In another embodiment, the invention still further provides a compound, wherein $R_2$, $R_3$ and $R_4$ are H, wherein $R_6$ is H, wherein $R_5$ is OH, and wherein $R_7$ is $CH_3$. In another embodiment, the invention also provides a compound, wherein $R_2$, $R_3$ and $R_4$ are H, wherein $R_6$ is H, wherein $R_5$ is selected from the group consisting of a linear hydroxyalkyl group, a linear alkoxycarbonyl group and OH, wherein $R_7$ is $CH_3$, and wherein $R_1$ is selected from a group consisting of a linear acylamino group, a linear aminoalkyl group and $NH_2$. In another embodiment, the invention further provides a compound, wherein $R_2$, $R_3$ and $R_4$ are H, wherein $R_6$ is H, wherein $R_7$ is $CH_3$, wherein $R_5$ is OH, and wherein $R_1$ is selected from a group consisting of a linear acylamino group, a linear aminoalkyl group and $NH_2$. In another embodiment, the invention further provides a compound, wherein $R_2$, $R_3$ and $R_4$ are H, wherein $R_6$ is H, wherein $R_7$ is $CH_3$, wherein $R_5$ is OH, and wherein $R_1$ is $NH_2$.

In a certain embodiment, the invention provides a compound, wherein the compound has the structure:

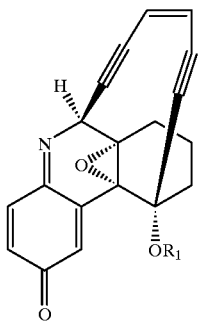

wherein $R_1$ is H, $C_1$–$C_7$ linear or branched chain alkyl, $C_1$–$C_7$ linear or branched chain alkoxyalkyl, $C_1$–$C_7$ linear or branched chain (aryl)alkyl, $C_1$–$C_7$ linear or branched chain (hydroxy)alkyl, $C_1$–$C_7$ linear or branched chain (acyloxy) alkyl, $C_1$–$C_7$ linear or branched chain alkoxycarbonyl, $C_1$–C7 linear or branched chain (aryloxy)alkyl, $C_1$–$C_7$ linear or branched chain acyl, aryl or $(CH_2)_j P(=O) (OH)_2$ where j is an integer from 0 to about 9. In another embodiment, the present invention provides the compound wherein $R_1$ is H.

As used herein, the term "linear or branched alkyl group" describes possible substituents for variable groups $R_1$–$R_7$, and encompasses, but is not limited to, a methyl, ethyl, propyl, isopropyl, t-butyl, sec-butyl, cyclopentyl or cyclohexanyl group.

As used herein, the terms "linear or branched alkoxycarbonyl," "hydroxy alkoxyalkyl," "acyl," "alkylaryl," and "alkoxy group" encompass, but are not limited to, a similar range of alkyl groups bonded to the functional group or moiety denoted by each respective term. Examples of alkoxy groups include methoxy, ethoxy, propoxy, n-butoxy, sec-butoxy, and cyclopentyloxy.

As used herein, an "aryl group" encompasses, but is not limited to, a phenyl, pyridyl, pyrryl, indolyl, naphthyl, thiophenyl or furanyl group. Examples of aryloxy groups include a phenoxy, 2-methylphenoxy, 3-methylphenoxy and 2-naphthyloxy. Examples of alkoxycarbonyl groups include a methoxycarbonyl, ethoxycarbonyl, propyloxycarbonyl, benzyloxycarbonyl, hydroxypropyloxy carbonyl and aminoethoxycarbonyl. Examples of acyloxy groups include acetoxy, propanoxy, butyryloxy, pentanoyloxy and hexanoyloxy. Examples of acyl groups include acetyl, propanoyl, butanoyl, pentanoyl and hexanoyl.

The subject invention provides a pharmaceutical composition comprising a therapeutically effective amount of the compound having the structure shown below dissolved or suspended in a pharmaceutically acceptable carrier

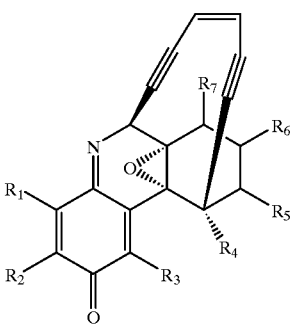

wherein $R_1$, $R_2$ and $R_3$ are independently the same or different and are H, Br, Cl, F, $NH_2$, $CO_2H$, or OH or a linear or branched alkyl, linear or branched acylamino, linear or branched acyloxy, linear or branched alkoxy-carbonyl, linear or branched alkoxy, aryloxy, linear or branched alkylaryl, linear or branched hydroxyalkyl, linear or branched aminoalkyl or aryl group; wherein $R_4$ is H, OH or a linear or branched alkoxy, linear or branched alkoxycarbonyl, linear or branched acyloxy or aryloxy group; wherein $R_5$ is H, Br, Cl, F, O=, OH or S—SR, or a linear or branched alkyl, aryl, linear or branched alkylaryl, linear or branched alkoxy, linear or branched acyloxy or linear or branched hydroxyalkyl group; wherein $R_6$ is H, Br, Cl, F, $CO_2H$, OH or S—SR', or a linear or branched alkyl, aryl, linear or branched alkylaryl, linear or branched alkoxycarbonyl, linear or branched alkoxy or linear or branched hydroxyalkyl group; wherein $R_7$ is H, OH or S—SR'', or a linear or branched alkyl, linear or branched alkoxycarbonyl, linear or branched alkoxy or linear or branched hydroxyalkyl group; and wherein R, R' and R'' are independently the same or different and are a linear or branched alkyl, linear or branched acyl or linear or branched alkoxyalkyl group.

In one embodiment, the invention provides the pharmaceutical composition, wherein $R_2$, $R_3$ and $R_4$ are H.

In another embodiment, the invention provides the pharmaceutical composition, wherein $R_2$, $R_3$ and $R_4$ are H, and wherein $R_7$ is a linear alkyl group. In another embodiment, the invention provides the pharmaceutical composition, wherein $R_2$, $R_3$ and $R_4$ are H, and wherein $R_7$ is $CH_3$.

In another embodiment, the invention provides the pharmaceutical composition, wherein $R_2$, $R_3$ and $R_4$ are H, and wherein $R_5$ and $R_6$ are independently the same or different and are selected from the group consisting of a linear hydroxyalkyl group, a linear alkoxycarbonyl group and OH. In another embodiment, the invention provides the pharmaceutical composition, wherein R2, $R_3$ and $R_4$ are H, wherein $R_5$ and $R_6$ are OH, and wherein $R_7$ is a linear alkyl group. In another embodiment, the invention provides the pharmaceutical composition, wherein $R_2$, $R_3$ and $R_4$ are H, wherein $R_5$ and $R_6$ are OH, and wherein $R_7$ is $CH_3$.

In another embodiment, the invention provides the pharmaceutical composition, wherein $R_2$, $R_3$ and $R_4$ are H, wherein $R_5$ and $R_6$ are OH, wherein $R_7$ is a linear alkyl group, and wherein $R_1$ is selected from a group consisting of a linear acylamino group, a linear aminoalkyl group and $NH_2$. In another embodiment, the invention provides the pharmaceutical composition, wherein $R_2$, $R_3$ and $R_4$ are H, wherein $R_5$ and $R_6$ are OH, wherein $R_7$ is $CH_3$, and wherein $R_1$ is selected from a group consisting of a linear acylamino group, a linear aminoalkyl group and $NH_2$. In another embodiment, the invention provides the pharmaceutical composition, wherein $R_2$, $R_3$ and $R_4$ are H, wherein $R_5$ and $R_6$ are OH, wherein $R_7$ is $CH_3$, and wherein $R_1$ is $NH_2$ In another embodiment, the invention provides the pharmaceutical composition, wherein $R_2$, $R_3$ and $R_4$ are H, and wherein $R_6$ is H. In another embodiment, the invention provides the pharmaceutical composition, wherein $R_2$, $R_3$ and $R_4$ are H, wherein $R_6$ is H. and wherein $R_7$ is a linear alkyl group. In another embodiment, the invention provides the pharmaceutical composition, wherein $R_2$, $R_3$ and $R_4$ are H, wherein $R_6$ is H, and wherein $R_7$ is $CH_3$. In another embodiment, the invention provides the pharmaceutical composition, wherein $R_2$, $R_3$ and $R_4$ are H, wherein $R_6$ is H, wherein $R_7$ is a linear alkyl group, and wherein $R_5$ is selected from the group consisting of a linear hydroxyalkyl group, a linear alkoxycarbonyl group and OH. In another embodiment, the invention provides the pharmaceutical composition, wherein $R_2$, $R_3$ and $R_4$ are H, wherein $R_6$ is H, wherein $R_7$ is a linear alkyl group, and wherein $R_5$ is OH. In another embodiment, the invention provides the pharmaceutical composition, wherein $R_2$, $R_3$ and $R_4$ are H, wherein $R_6$ is H, wherein $R_5$ is OH, and wherein $R_7$ is $CH_3$. In another embodiment, the invention provides the pharmaceutical composition, wherein $R_2$, $R_3$ and $R_4$ are H, wherein $R_6$ is H, wherein $R_5$ is selected from the group consisting of a linear hydroxyalkyl group, a linear alkoxycarbonyl group and OH, wherein $R_7$ is a linear alkyl group, and wherein $R_1$ is selected from a group consisting of a linear acylamino group, a linear aminoalkyl group and $NH_2$. In another embodiment, the invention provides the pharmaceutical composition, wherein $R_2$, $R_3$ and $R_4$ are H, wherein $R_6$ is H, wherein R5 is OH, wherein $R_7$ is a linear alkyl group, and wherein RE is selected from a group consisting of a linear acylamino group, a linear aminoalkyl group and $NH_2$.

In another embodiment, the invention provides the pharmaceutical composition, wherein $R_2$, $R_3$ and $R_4$ are H, wherein $R_6$ is H, wherein $R_5$ is OH, wherein $R_1$ is selected from a group consisting of a linear acylamino group, a linear aminoalkyl group and $NH_2$. and wherein $R_7$ is $CH_3$. In another embodiment, the invention provides the pharmaceutical composition, wherein $R_2$, $R_3$ and $R_4$ are H, wherein $R_6$ is H, wherein $R_5$ is OH, wherein $R_1$ is $NH_2$. and wherein $R_7$ is $CH_3$.

The subject invention also provides a pharmaceutical composition having the structure above wherein the carrier is a solid and the composition is a tablet. In one embodiment, the invention provides the pharmaceutical composition wherein the therapeutically effective amount is an amount from about 0.002 to about 200 mg.

In a certain embodiment, the invention provides a pharmaceutical composition wherein the compound has the structure:

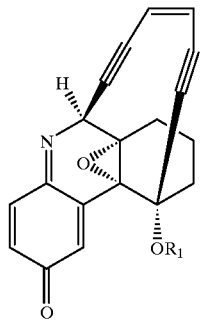

wherein $R_1$ is H, $C_1$–$C_7$ linear or branched chain alkyl, $C_1$–$C_7$ linear or branched chain alkoxyalkyl, $C_1$–$C_7$ linear or branched chain (aryl)alkyl, $C_1$–$C_7$ linear or branched chain (hydroxy)alkyl, $C_1$–$C_7$ linear or branched chain (acyloxy) alkyl, $C_1$–$C_7$ linear or branched chain alkoxycarbonyl, $C_1$–$C_7$ linear or branched chain (aryloxy)alkyl, $C_1$–$C_7$ linear or branched chain acyl, aryl or $(CH_2)_jP(O=)(OH)_2$ where j is an integer from 0 to about 9. In another embodiment, the invention provides the pharmaceutical composition wherein $R_1$ is H.

The subject invention further provides a pharmaceutical composition having the structure above wherein the carrier is a liquid and the composition is a solution. In one embodiment, the invention provides the pharmaceutical composition wherein the therapeutically effective amount is an amount from about 0.002 to about 100 mg per mL of solution.

The subject invention provides a process of synthesizing a compound having the structure:

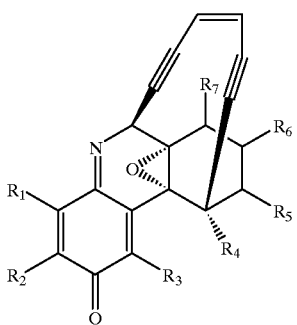

wherein $R_1$, $R_2$ and $R_3$ are independently the same or different and are H, Br, Cl, F, $NH_2$, $CO_2H$, or OH or a linear or branched alkyl, linear or branched acylamino, linear or branched acyloxy, linear or branched alkoxycarbonyl, linear or branched alkoxy, aryloxy, linear or branched alkylaryl, linear or branched hydroxyalkyl, linear or branched aminoalkyl or aryl group; wherein $R_4$ is H, OH or a linear or branched alkoxy, linear or branched alkoxycarbonyl, linear or branched acyloxy or aryloxy group; wherein $R_5$ is H, Br, Cl, F, O=, OH or S—SR, or a linear or branched alkyl, aryl, linear or branched alkylaryl, linear or branched alkoxy, linear or branched acyloxy or linear or branched hydroxyalkyl group; wherein $R_6$ is H, Br, Cl, F, $CO_2H$, OH or S—SR', or a linear or branched alkyl, aryl, linear or branched alkylaryl, linear or branched alkoxycarbonyl, linear or branched alkoxy or linear or branched hydroxyalkyl group; wherein $R_7$ is H, OH or S—SR", or a linear or branched alkyl, linear or branched alkoxycarbonyl, linear or branched alkoxy or linear or branched hydroxyalkyl group; and wherein R, R' and R' are independently the same or different and are a linear or branched alkyl, linear or branched acyl or linear or branched alkoxyalkyl group, which comprises:

(a) preparing a compound having the structure:

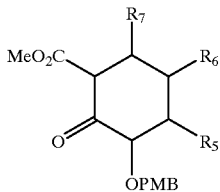

wherein $R_5$ is H, Br, Cl, F, O=, OH or S—SR, or a linear or branched alkyl, aryl, linear or branched alkylaryl, linear or branched alkoxy, linear or branched acyloxy or linear or branched hydroxyalkyl group; wherein $R_6$ is H, Br, Cl, F, $CO_2H$, OH or S—SR', or a linear or branched alkyl, aryl, linear or branched alkylaryl, linear or branched alkoxycarbonyl, linear or branched alkoxy or linear or branched hydroxyalkyl group; wherein $R_7$ is H, OH or S—SR", or a linear or branched alkyl, linear or branched alkoxycarbonyl, linear or branched alkoxy or linear or branched hydroxyalkyl group; and wherein R, R' and R" are independently the same or different and are a linear or branched alkyl, linear or branched acyl or linear or branched alkoxyalkyl group;

(b) treating the compound formed in step (a) with trifluoroacetic anhydride under suitable conditions to form a compound having the structure:

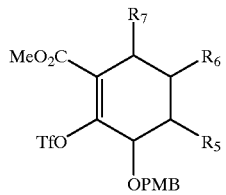

wherein $R_5$ is H, Br, Cl, F, O=, OH or S—SR, or a linear or branched alkyl, aryl, linear or branched alkylaryl, linear or branched alkoxy, linear or branched acyloxy or linear or branched hydroxyalkyl group; wherein $R_6$ is H, Br, Cl, F, $CO_2H$, OH or S—SR', or a linear or branched alkyl, aryl, linear or branched alkylaryl, linear or branched alkoxycarbonyl, linear or branched alkoxy or linear or branched hydroxyalkyl group; wherein $R_7$ is H, OH or S—SR", or a linear or branched alkyl, linear or branched alkoxycarbonyl, linear or branched alkoxy or linear or branched hydroxyalkyl group; and wherein R, R' and R" are independently the same or different and are a linear or branched alkyl, linear or branched acyl or linear or branched alkoxyalkyl group;

(c) (i) coupling the compound formed in step (b) with a compound having the structure:

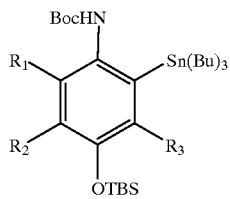

wherein $R_1$, $R_2$ and $R_3$ are independently the same or different and are H, Br, Cl, F, $NH_2$, $CO_2H$, or OH or a linear or branched alkyl, linear or branched acylamino, linear or branched acyloxy, linear or branched alkoxy-carbonyl, linear or branched alkoxy, aryloxy, linear or branched alkylaryl, linear or branched hydroxyalkyl, linear or branched aminoalkyl or aryl group; using an organometallic reagent under suitable conditions; (ii) reducing under suitable conditions; and (iii) oxidizing under suitable conditions to form a compound having the structure:

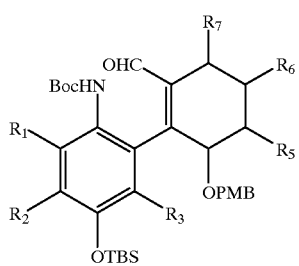

(d) treating the compound formed in step (c) with an acid catalyst under suitable conditions to form a compound having the structure:

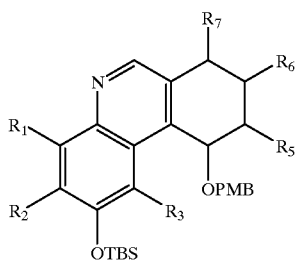

(e) (i) reacting the compound formed in step (d) with MC≡CCH=CHC≡CM under suitable conditions and (ii) treating with TEOC—Cl under suitable conditions to form a compound having the structure:

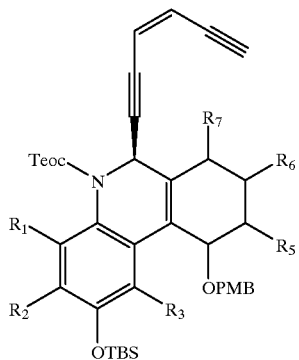

wherein M is selected from the group consisting of MgBr, MgCl, MgI, Li, Na, K and Cs;

(f) (i) epoxidizing the compound formed in step (e) with a peroxidant under suitable conditions, (ii) deprotecting under suitable conditions, and (iii) oxidizing with an oxidant under suitable conditions to form a compound having the structure:

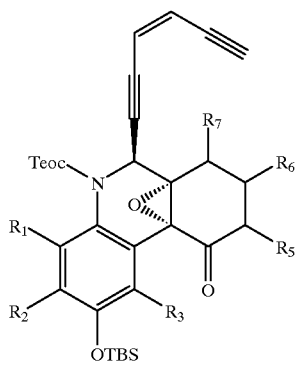

(g) cyclizing the compound formed in step (f) with a base under suitable conditions to form a compound having the structure:

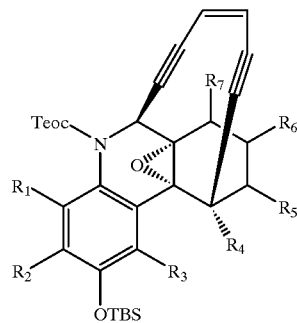

(h) de-silylating the compound formed in step (g) under suitable conditions and subsequently oxidizing under suitable conditions to form a compound having the structure:

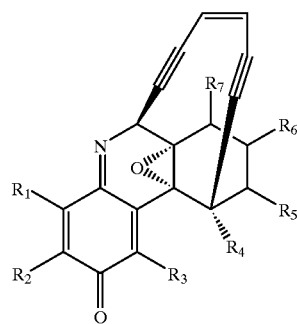

wherein $R_1$, $R_2$ and $R_3$ are independently the same or different and are H, Br, Cl, F, $NH_2$, $CO_2H$, or OH or a linear or branched alkyl, linear or branched acylamino, linear or branched acyloxy, linear or branched alkoxy-carbonyl, linear or branched alkoxy, aryloxy, linear or branched alkylaryl, linear or branched hydroxyalkyl, linear or branched aminoalkyl or aryl group; wherein $R_4$ is H, OH or a linear or branched alkoxy, linear or branched alkoxycarbonyl, linear or branched acyloxy or aryloxy group; wherein $R_5$ is H, Br, Cl, F, O=, OH or S—SR, or a linear or branched alkyl, aryl, linear or branched alkylaryl, linear or branched alkoxy, linear or branched acyloxy or linear or branched hydroxyalkyl group; wherein $R_6$ is H, Br, Cl, F, $CO_2H$, OH or S—SR', or a linear or branched alkyl, aryl, linear or branched alkylaryl, linear or branched alkoxycarbonyl, linear or branched alkoxy or linear or branched hydroxyalkyl group; wherein $R_7$ is H, OH or S—SR", or a linear or branched alkyl, linear or branched alkoxycarbonyl, linear or branched alkoxy or linear or branched hydroxyalkyl group; and wherein R, R' and R" are independently the same or different and are a linear or branched alkyl, linear or branched acyl or linear or branched alkoxyalkyl group.

As used herein, the compound having the structure:

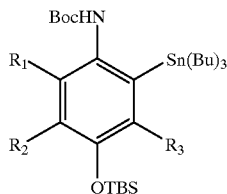

herein $R_1$, $R_2$ and $R_3$ are defined as set forth above, is prepared according to procedures known to one of ordinary skill in the art. See, for example, Isobe, T., and Nishikawa, T., *Tetrahedron*, 50, 5621 (1994). Step (b) is carried out using trifluoroacetic anhydride in the presence of an organic base, such as pyridine or triethylamine, in an organic solvent such as dichloromethane. Step (c) (i) is performed using an organometallic catalyst, such as $Pd_2(dba)_3$ in the presence of a non-interacting solvent, such as benzene or toluene. Step (c) (ii) is effected using any of several satisfactory reducing agents, including DibalH or another hindered aluminum hydride, at low temperatures (−78° C.) in an organic solvent, such as dichloromethane. Step (c) (iii) is performed using a mild oxidant, such as manganese dioxide, in an organic solvent, such as dichloromethane. Intramolecular condensation step (d) is carried out using an acid catalyst, such as dilute trifluoroacetic acid, in a non-interacting solvent, such as dichloromethane.

Addition step (e) is performed using a bis-organometallic enediyne reagent, which may be an organolithium, organosodium, or Grignard reagent, followed by treatment with carbamyl halide, such as TEOC—Cl, which quenches the anion formed at nitrogen during the 1,2-addition reaction. The reagent is most preferably a Grignard reagent wherein M is MgBr.

Epoxidizing step (f) (i) is carried out using a variety of epoxidizing reagents, such as peracetic acid, perbenzoic acid, and m-chloroperbenzoic acid, in an inert organic solvent, such as dichloromethane. Deprotection step (f) (ii) is performed under mild conditions using an oxidant such as 2,3-dichloro-5,6-dicyanobenzoquinone (DDQ) in a heterogeneous or homogeneous reaction mixture. Oxidation step (f) (iii) is carried out using a mild oxidant such as pyridinium dichromate in an inert organic solvent such as dichloromethane.

Ring forming step (g) is effected using a strong non-nucleophilic base, such as LDA, at low tempertures (−78° C.) in inert polar solvent, such as tetrahydrofuran (THF), diethyl ether, etc. Finally, de-silylating step (h) is performed using a tetraalkylammonium fluoride salt, preferably tetrabutylammonium fluoride, in a polar organic solvent, such as tetrahydrofuran, followed by treatment with a mild oxidant, such as $PhI(OAc)_2$.

In one embodiment, the invention provides a process of forming the compound in step (a) above having the structure:

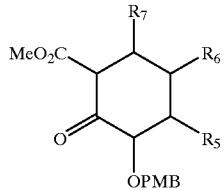

wherein $R_5$ is H, Br, Cl, F, O=, OH or S—SR, or a linear or branched alkyl, aryl, linear or branched alkylaryl, linear or branched alkoxy, linear or branched acyloxy or linear or branched hydroxyalkyl group; wherein $R_6$ is H, Br, Cl, F, $CO_2H$, OH or S—SR', or a linear or branched alkyl, aryl, linear or branched alkylaryl, linear or branched alkoxycarbonyl, linear or branched alkoxy or linear or branched hydroxyalkyl group; wherein $R_7$ is H, OH or S—SR", or a linear or branched alkyl, linear or branched alkoxycarbonyl, linear or branched alkoxy or linear or branched hydroxyalkyl group; and wherein R, R' and R" are independently the same or different and are a linear or branched alkyl, linear or branched acyl or linear or branched alkoxyalkyl group; which comprises:

(a) treating 2-hydroxycyclohexanone with a base and p-methoxybenzyl chloride under suitable conditions; and (b) reacting the product of step (a) with a base and $CNCO_2R$, wherein R is a linear or branched chain alkyl group, under suitable conditions to form the compound.

The invention also provides a process, wherein the base of step (a) above is sodium hydride and the base of step (b) is lithium diisopropylamide (LDA). In one embodiment, the invention provides a process, wherein R in step (b) is $CH_3$. Step (a) is carried out in the presence of a non-nucleophilic base, such as sodium hydride, potassium t-butoxide or LDA, at temperatures ranging from −78° C. to about 50° C., in a non-interacting organic solvent such as diethyl ether. Step (b) is performed using a strong non-nucleophilic base, such as sodium hydride, LDA or lithium diethylamide, at temperatures ranging from −78° C. to about 50° C., in a non-interacting organic solvent or solvent mixture, such as tetrahydrofuran, hexane and/or diethyl ether.

In another embodiment, the invention provides a process of synthesizing an enediyne quinone imine having the structure:

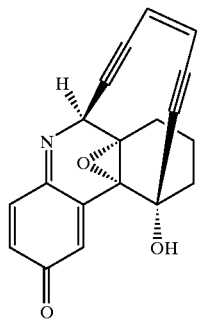

which comprises:

(a) condensing an aryl amine having the structure:

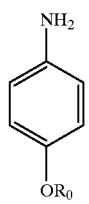

wherein $R_0$ is a $C_1$–$C_7$ linear or branched chain alkyl, $C_1$–$C_7$ linear or branched chain (aryl)alkyl, $C_1$–$C_7$ linear or branched chain alkoxyalkyl aryl, $C_1$–$C_7$ linear or branched chain alkylaryl group, with a keto ester having the structure:

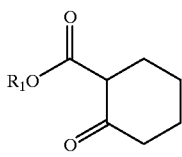

wherein $R_1$ is a $C_1$–$C_7$ linear or branched chain alkyl, $C_1$–$C_7$ linear or branched chain alkoxyalkyl, $C_1$–$C_7$ linear or branched chain (aryl)alkyl, aryl, $C_1$–$C_7$ linear or branched chain alkylaryl or haloaryl group, to form an unsaturated lactam having the structure:

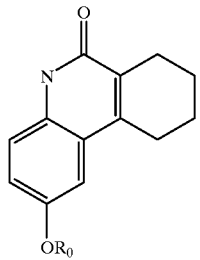

(b) triflating the unsaturated lactam formed in step (a) to form a triflate having the structure:

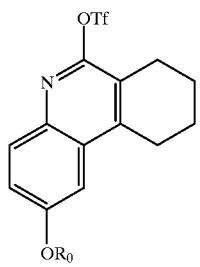

(c) reducing the triflate formed in step (b) to form a tricylic compound having the structure:

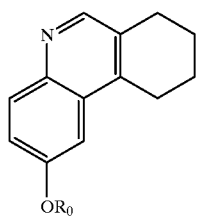

(d) cleaving and acylating the tricyclic compound formed in step (c) to form an O-acyl tricyclic compound having the structure:

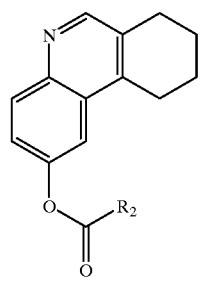

wherein $R_2$ is a $C_1$–C7 linear or branched chain alkyl, $C_1$–$C_7$ linear or branched chain alkoxyalkyl, $C_1$–$C_7$ linear or branched chain (aryl)alkyl, aryl, $C_1$–$C_7$ linear or branched chain alkylaryl or haloaryl group;

(e) oxidizing the O-acyl tricyclic compound formed in step (d) to form an N-oxide having the structure:

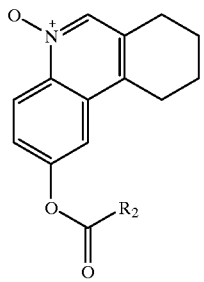

(f) acylating the N-oxide formed in step (d) to form a diacyl compound having the structure:

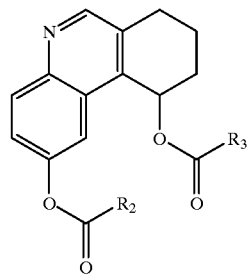

wherein $R_3$ is a $C_1$–$C_7$ linear or branched chain alkyl, $C_1$–$C_7$ linear or branched chain alkoxyalkyl, $C_1$–$C_7$ linear or branched chain (aryl)alkyl, aryl, $C_1$–$C_7$ linear or branched chain alkylaryl or haloaryl group;

(g) adding an acetylide having the formula H—C≡C—M wherein M is MgBr, MgCl, MgF, MgI, Na, K, Li or Cs to the diacyl compound formed in step (f) and quenching with TEOC—X wherein X is F, Cl, Br or I to form an acetylene adduct having the structure:

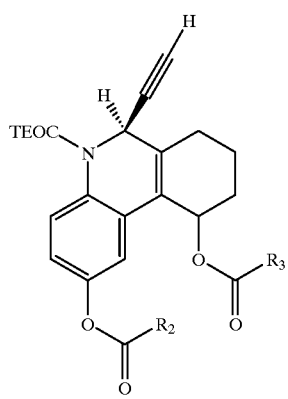

(h) epoxidizing the acetylene adduct formed in step (g) to form a diacyl epoxide having the structure:

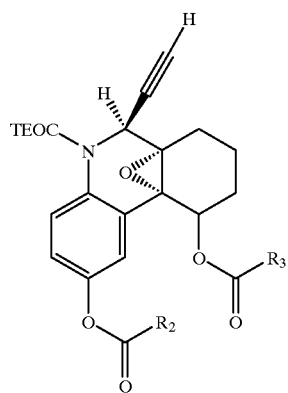

(i) de-acylating and silylating the diacyl epoxide formed in step (h) to form a monosilyl acyl epoxide having the structure:

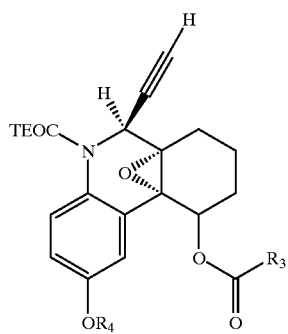

wherein $R_4$ is a trimethylsilyl, triethylsilyl, triisopropylsilyl, dimethylsilyl-t-butyl, methyldibenzyl-silyl, dimethylbenzylsilyl, methyldiphenylsilyl, di-methylphenylsilyl or triphenylsilyl group;

(j) reducing the monosilyl acyl epoxide formed in step (i) to form a epoxyalcohol having the structure:

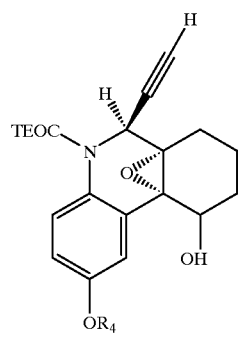

(k) oxidizing the epoxyalcohol formed in step (j) to form an epoxy ketone having the structure:

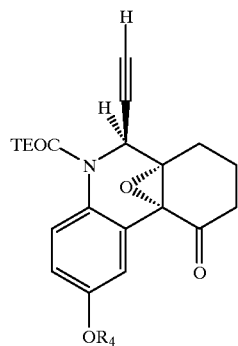

(l) coupling the epoxy ketone formed in step (k) with a silyl eneyne having the structure:

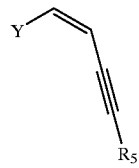

wherein Y is Cl, Br, I or F and wherein $R_5$ is a trimethylsilyl, triethylsilyl, triisopropylsilyl, dimethylsilyl-t-butyl, methyldibenzylsilyl, dimethyl-benzylsilyl, methyldiphenylsilyl, dimethylphenylsilyl or triphenylsilyl group, to form a silyl enediyne ketone having the structure:

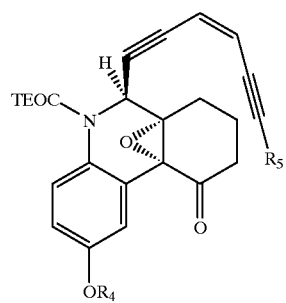

(m) de-silylating the silyl enediyne ketone formed in step (l) to form an enediyne ketone having the structure:

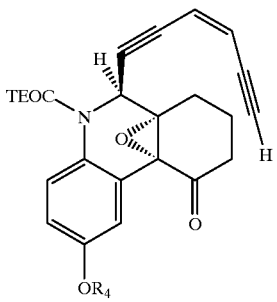

(n) cyclizing the enediyne ketone formed in step (m) to form a enediyne alcohol having the structure:

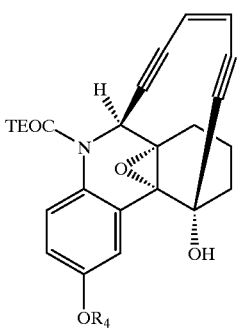

(o) deprotecting and oxidizing the enediyne alcohol formed in step (n) to form the enediyne quinone imine.

Condensing step (a) is performed at elevated temperatures ranging from 110° C. to 200° C., preferably between 170° C. and 195° C., and most preferably at 190° C., followed by treatment with a strong acid such as sulfuric acid at elevated temperatures, ranging from 80° C. to 125° C., preferably between 90° C. and 110° C., and most preferably at 100° C.

Triflation step (b) is carried out using triflic anhydride in an inert organic solvent such as dichloromethane at low temperatures, ranging from −100° C. to −50° C., preferably between −90° C. and −60° C., and most preferably at −78° C., and warming to temperatures ranging between −20° C. and 15° C., and preferably to 0° C.

Reduction step (c) is effected using an organometallic catalyst, such as $Pd(PPh_3)_4$ in the presence of a proton donor such as formic acid, a base such as triethylamine and a non-interacting solvent, such as dioxane, at elevated temperatures, ranging from 75° C. to 150° C., preferably between 90° C. and 115° C., and most preferably at 100° C.

Cleavage and acylation step (d) is achieved using a mild nucleophilic reagent such as sodium ethyl mercaptide in a non-aqueous, dipolar solvent such as N,N-dimethyl formamide at elevated temperatures, ranging from 140° C. to 190° C., preferably between 155° C. and 170° C., and most preferably at 160° C., followed by treatment with an acylating reagent such as acetyl chloride or acetic anhydride at temperatures, ranging from 0° C. to 35° C., preferably at 25° C.

Oxidation step (e) is carried out using an oxidant such as peracetic acid, perbenzoic acid, but preferably m-chloroperbenzoic acid, at temperatures, ranging from 10° C. to 30° C., preferably at 25° C., in an inert organic solvent such as dichloromethane.

Reductive acylation (f) is effected using a variety of reagents, such as acetic anhydride, at elevated temperatures ranging from 50° C. to 100° C., preferably between 60° C. and 80° C., but most preferably at 70° C.

Addition step (g) is performed using an metallo-acetylide, ide in which the metal may be lithium, sodium, or Mg halide, preferably MgBr or MgCl, followed by treatment with carbamyl halide, such as TEOC—Cl, in an inert organic solvent such as tetrahydrofuran, initially at low temperatures, ranging from −90° C. to −60° C., preferably between −85° C. and −70° C., and most preferably at −78° C., and warming to temperatures ranging between −25° C. and 20° C., and preferably to 0° C.

Epoxidizing step (h) is carried out using a variety of epoxidizing reagents, such as peracetic acid, perbenzoic acid, and m-chloroperbenzoic acid, preferably the latter, in either an inert organic solvent, such as dichloro-methane, or more preferably, under phase transfer conditions, for example, in aqeuous sodium bicarbonate/di-chloromethane, at temperatures ranging from −20 to 60° C., preferably at ambient temperature.

Selective deacylation/silylation step (i) is performed using a mild nucleophilic cleaving agent such as potassium cyanide in a polar solvent such as methanol, ethanol, or isopropanol, followed by treatment with a silyl halide, preferably t-butyldimethylsilyl chloride in the presence of a mild base such as imidizole.

Step (j) is effected using any of several satisfactory reducing agents, including DIBAL or another hindered aluminum hydride, at low temperatures, preferably at −78° C., in an organic solvent, such as dichloromethane.

Oxidation step (k) is carried out using a mild oxidant such as pyridinium chlorochromate or dichromate in an inert organic solvent such as dichloromethane.

Coupling step (l) is effected using an organometallic catalyst under a range of conditions, most preferably using $Pd(PPh_3)_4$ in the presence of CuI and a base such as n-butylamine.

De-silylation step (m) is carried out using a variety of mild oxidative deprotecting agents, preferably silver nitrate, in the presence of a protic solvent such as ethanol or methanol.

Ring forming step (n) is effected using a strong non-nucleophilic base, such as sodium hydride, potassium t-butoxide or LDA, at temperatures ranging from −78° C. to about −25° C., preferably at −78° C. in a non-interacting organic solvent such as toluene or xylenes.

De-silylating step (o) is performed using an ammonium fluoride salt, such as tetraalkylammonium fluoride salt, preferably tetra-n-butylammonium fluoride, in a polar organic solvent, such as tetrahydrofuran, followed by treatment with a mild oxidant, such as $PhI(OAc)_2$.

The methods of preparation set forth herein provide the disclosed compounds in either racemic or enantiomerically pure form. The racemic forms were used in assays of biological activity. Accordingly, the disclosed compounds encompass either (+) or (−) enantiomer as well as the racemate thereof.

The subject invention provides a conjugate which comprises a compound covalently bonded to a monoclonal antibody, wherein the compound has the structure:

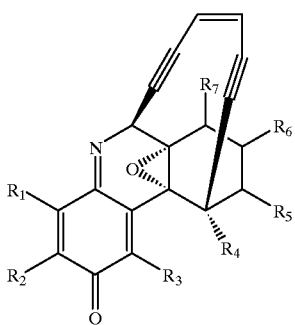

antibody, wherein the compound has the structure:

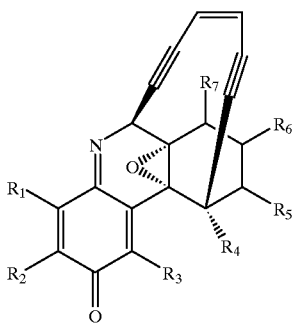

wherein $R_1$, $R_2$ and $R_3$ are independently the same or different and are H, Br, Cl, F, $NH_2$, $CO_2H$, OH, linear or branched alkyl, linear or branched acylamino, linear or branched acyloxy, linear or branched alkoxycarbonyl, linear or branched alkoxy, aryloxy, linear or branched alkylaryl, linear or branched hydroxyalkyl, linear or branched aminoalkyl or aryl; wherein $R_4$ is H, OH, linear or branched alkoxy, linear or branched alkoxycarbonyl, linear or branched acyloxy or aryloxy; wherein $R_5$ is H, Br, Cl, F, O=, OH, S—SR, linear or branched alkyl, aryl, linear or branched alkylaryl, linear or branched alkoxy, linear or branched acyloxy or linear or branched hydroxyalkyl; wherein $R_6$ is H, Br, Cl, F, $CO_2H$, OH, S—SR', linear or branched alkyl, aryl, linear or branched alkylaryl, linear or branched alkoxycarbonyl, linear or branched alkoxy or linear or branched hydroxyalkyl; wherein $R_7$ is H, OH, S—SR", linear or branched alkyl, linear or branched alkoxycarbonyl, linear or branched alkoxy or linear or branched hydroxyalkyl; wherein R, R' and R" are independently the same or different and are linear or branched alkyl, linear or branched acyl or linear or branched alkoxyalkyl; wherein the monoclonal antibody is immunoreactive with a determinant site of a cell surface antigen of human tumor cells; wherein the compound is covalently bonded to the monoclonal antibody via a cleavable linker connecting suitable functional groups, respectively, of the compound and the monoclonal antibody; and wherein the cleavable linker is selected from a group consisting of glutarate, N-hydroxysuccinic amide ester, a peptide, monosaccharide, oligosaccharide, thioether, disulfide, trisulfide, hydrazide and hydrazone moieties.

In one embodiment, the invention provides a conjugate, wherein the monoclonal antibody (MAb) is selected from the group consisting of HT29/15, MH55, ME195, L101, B5, CLT85, 19.9, T43, F36/22, GA-17 (Kondo, S., et al., *Eur. J. Cancer*, 29A, 420 (1993)), L6 (Goodman, G. E., et al., *Cancer Immunol. Immunother.*, 36, 267 (1993)), B72.3 (A.T.C.C. No. HB 8108), 425 (Adair, J. R., et al., WO 91/09967 (1991)), L72 (Irie, R. F., et al., *Proc. Natl. Acad. Sci. USA*, 83, 8694 (1986)), A7 (Kaitamura, K., et al., *Tohoku J. Exn. Med.* 161. 199 (1990)), A33 (Adair, J. R., *Immun. Rev.*, 130, 5 (1992)), BW431/26P67.6 (Adair, J. R., Ibid.) and A5B7 (Adair, J. R., Ibid.).

As used herein, the monoclonal antibodies immunoreact specifically with the surface of tumor cells, and serve to transport the covalently bonded enediyne prodrug directly to the tumor cell surface. Preferably, the monoclonal antibodies are humanized in order to reduce immunogenic rejection. Kaitamura, K., et al., *Tohoku J. Exi. Med.*, 161, 199 (1990).

As used herein, the cleavable linker connecting suitable functional groups, respectively, of the compound and the monoclonal antibody serves as a temporary connector between the compound and the MAb. Under physiological conditions, the covalent bond between the compound and the cleavable linker is broken, thereby releasing the cytotoxic compound in the vicinity of the tumor cell surface. Standard methods of modifying MAbs are utilized to introduce the covalent bonds among the compound, cleavable linker and MAb. Hinman, L. M., and Yarranton, G., *Ann. Repts. Med. Chem.*, 28, 237 (1993). Amino acid side chains present on the MAb (e.g., lysine, cysteine, serine, etc.) react with either a carboxylic, mercapto, amino, or alcohol moiety in either the cleavable linker, or on the compound itself to form a covalent bond. Thus, the ∈-amino group of a lysine may react with a carboxylic moiety of either the linker or the compound to provide an amide bond.

In addition, in accordance with the subject invention, a mercapto moiety of cysteine may react with a mercapto moiety of a cleavable linker to form a disulfide. Procedures are well known in the art to convert alcohol groups (ROH) to thioacetates (RSAc), which can then be converted to disulfide linkages (RSSR'). For example, see Volante, R. P., *Tetrahedron Lett.*, 22, 3119 (1981). Trisulfides can be formed by reduction of the thioacetate with diisobutylaluminum hydride (DiBalH) at low temperatures (–78° C.), followed by treatment with N-(methyldithio)phthalimide in an organic solvent at ambient temperatures. See, for example, Hitchckock, S. A., et al., *Angew. Chem. Int. Ed. Engl.*, 33, 858 (1994).

The invention also provides a conjugate as above with a trisulfide linker, wherein the compound has the structure:

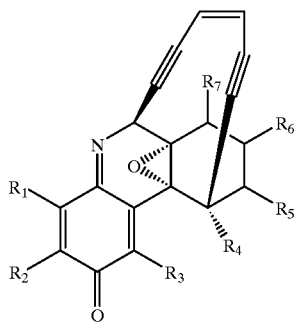

wherein one of $R_1$, $R_2$, $R_3$, $R_4$, $R_5$, $R_6$ and $R_7$ is an alkyltrisulfide moiety $(CH2)_nS$—S—S—MAb, where S—MAb represents the monoclonal antibody and a thiol group of a cysteine residue of the monoclonal antibody and n is 1 to about 5.

In one embodiment, the invention provides a conjugate which comprises a compound covalently bonded to a monoclonal antibody wherein the compound has the structure:

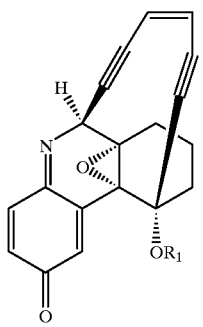

wherein $R_1$ is H, $C_1$–$C_7$ linear or branched chain alkyl, $C_1$–$C_7$ linear or branched chain alkoxyalkyl, $C_1$–$C_7$ linear or branched chain (aryl)alkyl, $C_1$–$C_7$ linear or branched chain (hydroxy)alkyl, $C_1$–$C_7$ linear or branched chain (acyloxy) alkyl, $C_1$–$C_7$ linear or branched chain alkoxycarbonyl, $C_1$–$C_7$ linear or branched chain (aryloxy)alkyl, $C_1$–$C_7$ linear or branched chain acyl, aryl or $(CH_2)_j P(=O)(OH)_2$, where j is an integer from 0 to about 9. In another embodiment, the invention provides the method wherein $R_1$ is H.

In a certain embodiment, the invention provides a conjugate as above, wherein MAb is a monoclonal antibody immunoreactive with an antigen on the surface of human astrocytomas, and wherein n is 2. In another embodiment, the invention provides a conjugate, wherein the MAb is GA-17. In another embodiment, the invention provides a conjugate, wherein MAb is an internalizing murine monoclonal antibody against human colon cancer, and wherein n is 2. In another embodiment, the invention provides a conjugate, wherein MAb is A7. In another embodiment, the invention provides a conjugate, wherein MAb is a humanized version of A7.

The invention also provides a conjugate as above, wherein the cleavable linker is a peptide and the peptide is a dipeptide moiety. The invention provides a conjugate, wherein the cleavable linker is a disulfide moiety. The invention provides a conjugate, wherein the cleavable linker is a trisulfide moiety.

Examples of monoclonal antibodies appropriate for practicing the subject invention include HT29/15 (A.T.C.C. No. HE 8246, anti-colon adenocarcinoma, cited in U.S. Pat. No. 4,579,827)), MH55 (A.T.C.C. No. HE 8412, anti-ovarian carcinoma, cited in U.S. Pat. No. 4,666,845), ME195 (A.T.C.C. No. HP 8431, anti-ovarian carcinoma, cited in U.S. Pat. No. 4,666,845), L101 (A.T.C.C. No. HB 8447, anti-human melanoma, cited in U.S. Pat. No. 4,806,628), B5 (A.T.C.C. No. HE 8453, anti-human melanoma, cited in U.S. Pat. No. 4,806,628), CLT85 (A.T.C.C. No. HB 8240, anti-colon cancer, cited in U.S. Pat. No. 4,579,827)), 19.9 (A.T.C.C. No. CRL 8019, CEA, cited in U.S. Pat. No. 4,349,528)), T43 (A.T.C.C. No. 8275, anti-human bladder tumor, cited in European Patent Application No. 84102517.4, publication No. 0 118 891, published Sep. 19, 1984)), and F36/22 (A.T.C.C. No. 8215, anti-human breast carcinoma, cited in European Patent Application No. 84400420.0, publication No. 0 118 365, published Sep. 12, 1984)).

In a preferred embodiment, a quinone imine enediyne substituted by a carbonyl group, as in an alkyl acyl compound, is reacted with a succinimidylcaproylhydrazide, formed by reacting a surface cysteine SH group of a MAb with maleimidocaproic acid, or a N-hydroxysuccinimide ester thereof (Fujiwara, K., et al., *J. Immunol. Meth.*, 45, 195 (1981)), followed by reaction with hydrazine, to generate the thioether caproylhydrazone conjugate. See Trail, P. A., et al., *Science*, 261, 212 (1993). The thiolinker to the MAb is acceptably stable in plasma (Thorpe, P. E., et al., *Cancer Res.*, 47, 5924 (1987)); the hydrazone bond is acid-labile in the acidic milieu of the lysozome where the cytotoxic compound is released. Trail, P. A., et al., *Cancer Res.*, 52, 5693 (1992); Braslawsky, G. R., et al., Ibid., 50, 6608 (1990).

The subject invention provides a conjugate which comprises an aglycone moiety covalently bonded to an oligosaccharide moiety, wherein the aglycone moiety has the structure:

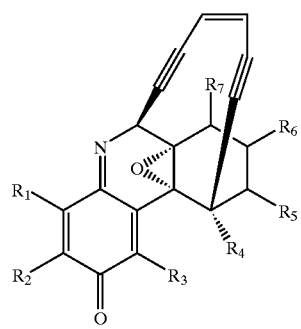

wherein $R_1$, $R_2$ and $R_3$, are independently the same or different and are H, Br, Cl, F, $NH_2$, $CO_2H$, OH, linear or branched alkyl, linear or branched acylamino, linear or branched acyloxy, linear or branched alkoxycarbonyl, linear or branched alkoxy, aryloxy, linear or branched alkylaryl, linear or branched hydroxyalkyl, linear or branched aminoalkyl or aryl; wherein $R_4$ is H, OH, linear or branched alkoxy, linear or branched alkoxycarbonyl, linear or branched acyloxy or aryloxy; wherein R5 is H, Br, Cl, F, O=, OH, S—SR, linear or branched alkyl, aryl, linear or branched alkylaryl, linear or branched alkoxy, linear or branched acyloxy or linear or branched hydroxyalkyl; wherein $R_6$ is H, Br, Cl, F, $CO_2H$, OH, S—SR', linear or branched alkyl, aryl, linear or branched alkylaryl, linear or branched alkoxycarbonyl, linear or branched alkoxy or linear or branched hydroxyalkyl; wherein $R_7$ is H, OH, S—SR", linear or branched alkyl, linear or branched alkoxycarbonyl, linear or branched alkoxy or linear or branched hydroxyalkyl; wherein R, R' and R" are independently the same or different and are linear or branched alkyl, linear or branched acyl or linear or branched alkoxyalkyl; wherein the aglycone moiety is covalently bonded via a glycosidic linkage through one of $R_1$, $R_2$, $R_3$, $R_4$, $R_5$, $R_6$ and $R_7$ being a hydroxyl or linear hydroxyalkyl; and wherein the oligosaccharide moiety comprises one or more sugar units selected from the group consisting of glucosyl, ribosyl, fucosyl, galactosyl, deoxyribosyl and an acylated aminosugar.

The invention also provides a conjugate which comprises an aglycone moiety covalently bonded to an oligosaccharide moiety, wherein the aglycone moiety has the structure:

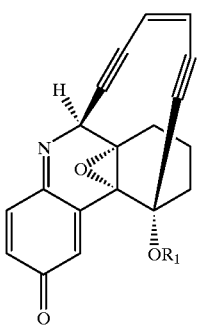

wherein $R_1$ is H, $C_1$–$C_7$ linear or branched chain alkyl, $C_1$–$C_7$ linear or branched chain alkoxyalkyl, $C_1$–$C_7$ linear or branched chain (aryl)alkyl, $C_1$–$C_7$ linear or branched chain (hydroxy)alkyl, $C_1$–$C_7$ linear or branched chain (acyloxy) alkyl, $C_1$–$C_7$ linear or branched chain alkoxycarbonyl, $C_1$–$C_7$ linear or branched chain (aryloxy)alkyl, $C_1$–$C_7$ linear or branched chain acyl, aryl or $(CH_2)_jP(=O)(OH)_2$, where j is an integer from 0 to about 9; and wherein the oligosaccharide moiety comprises one or more sugar units selected from the group consisting of glucosyl, ribosyl, fucosyl, galactosyl, deoxyribosyl and an acylated aminosugar. In one embodiment, the invention provides a conjugate wherein $R_1$ is H.

The invention further provides a conjugate which comprises a compound covalently bonded to an enzyme substrate by linking atoms wherein the compound has the structure:

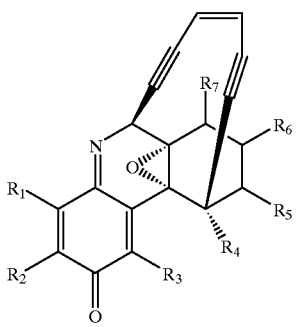

wherein $R_1$, $R_2$ and $R_3$ are independently the same or different and are H, Br, Cl, F, $NH_2$, $CO_2H$, OH, linear or branched alkyl, linear or branched acylamino, linear or branched acyloxy, linear or branched alkoxycarbonyl, linear or branched alkoxy, aryloxy, linear or branched alkylaryl, linear or branched hydroxyalkyl, linear or branched aminoalkyl or aryl; wherein $R_4$ is H, OH, linear or branched alkoxy, linear or branched alkoxycarbonyl, linear or branched acyloxy or aryloxy; wherein $R_5$ is H, Br, Cl, F, O=, OH, S—SR, linear or branched alkyl, aryl, linear or branched alkylaryl, linear or branched alkoxy, linear or branched acyloxy or linear or branched hydroxyalkyl; wherein $R_6$ is H, Br, Cl, F, $CO_2H$, OH, S—SR', linear or branched alkyl, aryl, linear or branched alkylaryl, linear or branched alkoxycarbonyl, linear or branched alkoxy or linear or branched hydroxyalkyl;

wherein $R_7$ is H, OH, S—SR", or linear or branched alkyl, linear or branched alkoxycarbonyl, linear or branched alkoxy or linear or branched hydroxyalkyl; wherein R, R' and R" are independently the same or different and are linear or branched alkyl, linear or branched acyl or linear or branched alkoxyalkyl; wherein the enzyme substrate is bonded to the compound via the linking atoms; wherein the compound and enzyme substrate respectively have at least one side-chain functional group; and the linking atoms are formed from the side-chain functional groups of the compound and enzyme substrate.

The invention also provides a conjugate which comprises a compound covalently bonded to an enzyme substrate by linking atoms wherein the compound has the structure:

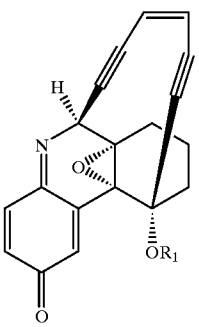

wherein $R_1$ is H, $C_1$–$C_7$ linear or branched chain alkyl, $C_1$–$C_7$ linear or branched chain alkoxyalkyl, $C_1$–$C_7$ linear or branched chain (aryl)alkyl, $C_1$–$C_7$ linear or branched chain (hydroxy)alkyl, $C_1$–$C_7$ linear or branched chain (acyloxy) alkyl, $C_1$–$C_7$ linear or branched chain alkoxycarbonyl, $C_1$–$C_7$ linear or branched chain (aryloxy)alkyl, $C_1$–$C_7$ linear or branched chain acyl, aryl or $(CH_2)_jP(=O)(OH)2$ where j is an integer from 0 to about 9; wherein the enzyme substrate is bonded to the compound via the linking atoms; wherein the compound and enzyme substrate respectively have at least one side-chain functional group; and the linking atoms are formed from the side-chain functional groups of the compound and enzyme substrate. In one embodiment, the invention provides a conjugate wherein $R_1$ is H. In another embodiment, the invention provides a conjugate wherein the enzyme substrate is a peptide, and the linking atoms comprise an amide, ester, hydrazone, disulfide or trisulfide moiety. In another embodiment, the invention provides a conjugate wherein the side chain functional group of the peptide substrate is an amino or carboxyl. In another embodiment, the invention provides a conjugate wherein the side chain functional group of the peptide substrate is an N-terminal amine and the linking atoms are NH(C=O). In another embodiment, the invention provides a conjugate wherein the side chain functional group of the peptide substrate is a C-terminal carboxylic acid and the linking atoms are NH(C=O) or O(C=O).

In one embodiment, the invention provides a conjugate wherein the enzyme is a peptidase and the peptide substrate is a dipeptide. Jungheim, L. N. and Shepherd, *Chem. Rev.*, 94, 1553 (1994).

In another embodiment, the invention provides a conjugate wherein the peptidase is carboxypeptidase A, and the dipeptide is selected from the group consisting of L-Glu-α-L-Phe and L-Glu-α-L-Ala. (See Kuefner, U., et al., *Biochemistry*, 29, 10540 (1990) for a previous use as a substrate.) In another embodiment, the invention provides a conjugate wherein the enzyme is a penicillin V/G amidase, wherein the substrate is an amide formed from an amino side group of the compound above and p-hydroxyphenoxyacetic acid and wherein the linking atoms are NH(C=O). (See Kerr, D. E., et al., *Cancer Immunol. Immunother.*, 31, 202 (1990).)

The subject invention therefore provides conjugates of highly cytotoxic analogues of dynemicin covalently bonded to linkers, which are used in conjunction with conjugates of enzymes and MAbs specifically immunoreactive with tumor cell surfaces. The linker serves to mask the functionally most active region of the compound, thereby tempering the usual toxicity of the compound for normal cells. The antibody-bound enzyme is localized near the tumor cell, and by locally unmasking the linker, the enzyme produces a high local concentration of cytotoxic drug.

Linkers may additionally be cleaved by reduction under physiological conditions, or by acid catalysis. An example of a linker which is acid-cleavable is one which incorporates a cis-aconitate moiety. A linker comprised of the tripeptide —Ala$_3$—, which may be connected via a carboxyl or amino group on the enediyne moiety, is cleavable by treatment with intracellular proteolytic enzymes. Reisfeld, et al. *Human Cancer Immunol.* II, 11, 341 (1991).

Peptide linkers are standard in the art, and are synthesized by known methods. Bodanszky, *Principles of Peltide Synthesis*, Springer-Verlag, Berlin (1984). Typically, a carboxylic acid moiety of the compound, for example, is activated by reaction with a coupling agent, such as dicylohexylaminocarbodiimide (DCC) or a water-soluble equivalent, and condensed with an alcohol or amino moiety of the linker or MAb to form a covalent bond.

In certain embodiments of the invention, linkers connecting the monoclonal antibody (MAb) or oligo-saccharide and enediyne include, but are not limited to, diaminoalkanes, such as 1,2-ethylene diamine, 1,3-prop-ylene diamine, and 1,4-butylene diamine, and dicarboxylic acids such as succinic, malonic, glutaric, maleic acid and adipic acid, and hydroxycarboxylic acids, such as 2-hydroxyacetic acid, 3-hydroxypropionic acid and 4-hydroxycyclopentylcarboxylic acid.

Another cleavable linker is a hydrazone, which may be formed from the subject quinone imine enediyne wherein any one of $R_1$–$R_7$ is either a linear or branched alkyl aldehyde or ketone or amino group.

An oligosaccharide linker is coupled via any one of its hydroxyl groups, though typically at the anomeric site, wherein the hydroxylic enediyne compound serves as an aglycone moiety; an aminosugar such as glucosamine is coupled via a hydroxyl group or an amino group using methods standard in the carbohydrate field. Thus, while protecting hydroxyl groups not intended to be coupled using trialkylsilyl groups or other suitable protecting groups, the glycosyl hydroxyl is reacted with an activating agent such as diethylaminosulfur trifluoride in a polar ethereal solvent such as THF at low temperatures to form the corresponding fluorosugar.

Treatment of an enediyne having the structure disclosed herein with the fluorosugar in the presence of a silver salt such as silver perchlorate provides the protected coupled oligosaccharide-compound conjugate. The protecting groups are cleaved using methods standard in the carbohydrate art.

The subject invention provides a method of treating tumors in a subject which comprises administering to the subject a therapeutically effective amount of any one of the compounds disclosed hereinabove. In another embodiment, the invention provides a conjugate wherein the enzyme is a penicillin V/G amidase, wherein the substrate is an amide formed from an amino side group of the compound and p-hydroxyphenoxyacetic acid, and wherein the linking atoms are NH(C=O).

The invention also provides a method of treating a tumor in a subject which comprises administering to the subject a therapeutically effective amount of the compound having the structure:

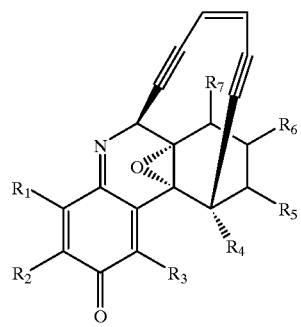

wherein $R_1$, $R_2$ and $R_3$ are independently the same or different and are H, Br, Cl, F, $NH_2$, $CO_2H$, OH, linear or branched alkyl, linear or branched acylamino, linear or branched acyloxy, linear or branched alkoxycarbonyl, linear or branched alkoxy, aryloxy, linear or branched alkylaryl, linear or branched hydroxyalkyl, linear or branched aminoalkyl or aryl; wherein $R_4$ is H, OH, linear or branched alkoxy, linear or branched alkoxycarbonyl, linear or branched acyloxy or aryloxy; wherein $R_5$ is H, Br, Cl, F, O=, OH, S—SR, linear or branched alkyl, aryl, linear or branched alkylaryl, linear or branched alkoxy, linear or branched acyloxy or linear or branched hydroxyalkyl; wherein $R_6$ is H, Br, Cl, F, $CO_2H$, OH, S—SR', or linear or branched alkyl, aryl, linear or branched alkylaryl, linear or branched alkoxycarbonyl, linear or branched alkoxy or linear or branched hydroxyalkyl; wherein $R_7$ is H, OH, S—SR'', or linear or branched alkyl, linear or branched alkoxycarbonyl, linear or branched alkoxy or linear or branched hydroxyalkyl; and wherein R, R' and R'' are independently the same or different and are linear or branched alkyl, linear or branched acyl or linear or branched alkoxyalkyl.

The invention also provides a method of treating a tumor in a subject which comprises administering to the subject a therapeutically effective amount of the compound having the structure:

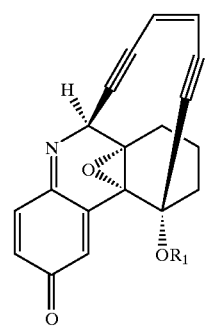

wherein $R_1$ is H, $C_1$–$C_7$ linear or branched chain alkyl, $C_1$–$C_7$ linear or branched chain alkoxyalkyl, $C_1$–$C_7$ linear or branched chain (aryl)alkyl, $C_1$–$C_7$ linear or branched chain (hydroxy)alkyl, $C_1$–$C_7$ linear or branched chain (acyloxy) alkyl, $C_1$–$C_7$ linear or branched chain alkoxycarbonyl, $C_1$–$C_7$ linear or branched chain (aryloxy)alkyl, $C_1$–$C_7$ linear or branched chain acyl, aryl or $(CH_2)_jP(=O)(OH)_2$, where j is an integer from 0 to about 9. In another embodiment, the invention provides the method wherein $R_1$ is H.

In one embodiment, the invention provides a method of treating a tumor wherein the tumor is a solid tumor. In another embodiment, the invention provides a method wherein the of of treating a tumor tumor is multi-drug resistant. In another embodiment, the invention provides a method wherein the therapeutically effective amount is an amount from about 0.002 to about 10 mg/kg of body weight.

The invention provides a method of inhibiting growth of tumor cells in a host which comprises administering to the host a therapeutically effective amount of the compound having the structure:

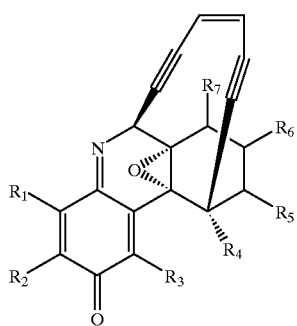

wherein $R_1$, $R_2$ and $R_3$ are independently the same or different and are H, Br, Cl, F, $NH_2$, $CO_2H$, OH, linear or branched alkyl, linear or branched acylamino, linear or branched acyloxy, linear or branched alkoxycarbonyl, linear or branched alkoxy, aryloxy, linear or branched alkylaryl, linear or branched hydroxyalkyl, linear or branched aminoalkyl or aryl; wherein $R_4$ is H, OH, linear or branched alkoxy, linear or branched alkoxycarbonyl, linear or branched acyloxy or aryloxy; wherein $R_5$ is H, Br, Cl, F, O=, OH, S—SR, linear or branched alkyl, aryl, linear or branched alkylaryl, linear or branched alkoxy, linear or branched acyloxy or linear or branched hydroxyalkyl; wherein $R_6$ is H, Br, Cl, F, $CO_2H$, OH, S—SR', linear or branched alkyl, aryl, linear or branched alkylaryl, linear or branched alkoxycarbonyl, linear or branched alkoxy or linear or branched hydroxyalkyl; wherein $R_7$ is H, OH, S—SR", or linear or branched alkyl, linear or branched alkoxycarbonyl, linear or branched alkoxy or linear or branched hydroxyalkyl; wherein R, R' and R" are independently the same or different and are linear or branched alkyl, linear or branched acyl or linear or branched alkoxyalkyl; wherein the enzyme substrate is bonded to the compound via the linking atoms; wherein the compound and enzyme substrate respectively have at least one side-chain functional group; and the linking atoms are formed from the side-chain functional groups of the compound and enzyme substrate.

The invention also provides a method of inhibiting growth of tumor cells in a host which comprises administering to the host a therapeutically effective amount of the compound having the structure:

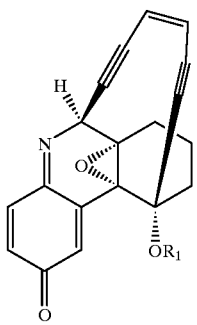

wherein $R_1$ is H, $C_1$–$C_7$ linear or branched chain alkyl, $C_1$–$C_7$ linear or branched chain alkoxyalkyl, $C_1$–$C_7$ linear or branched chain (aryl)alkyl, $C_1$–$C_7$ linear or branched chain (hydroxy)alkyl, $C_1$–$C_7$ linear or branched chain (acyloxy)alkyl, $C_1$–$C_7$ linear or branched chain alkoxycarbonyl, $C_1$–$C_7$ linear or branched chain (aryloxy)alkyl, $C_1$–$C_7$ linear or branched chain acyl, aryl or $(CH_2)_jP(=O)(OH)_2$, where j is an integer from 0 to about 9. In another embodiment, the invention provides the method wherein $R_1$ is H.

In one embodiment, the invention provides a method wherein the therapeutically effective amount is an amount from about 0.002 to about 10 mg/kg of body weight.

The invention further provides a method of treating a tumor in a subject which comprises administering to the subject a therapeutically effective amount of the compound having the structure:

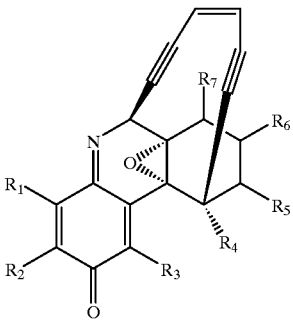

wherein $R_1$, $R_2$ and $R_3$ are independently the same or different and are H, Br, Cl, F, $NH_2$, $CO_2H$, OH, linear or branched alkyl, linear or branched acylamino, linear or branched acyloxy, linear or branched alkoxycarbonyl, linear or branched alkoxy, aryloxy, linear or branched alkylaryl, linear or branched hydroxyalkyl, linear or branched aminoalkyl or aryl; wherein $R_4$ is H, OH, linear or branched alkoxy, linear or branched alkoxycarbonyl, linear or branched acyloxy or aryloxy; wherein $R_5$ is H, Br, Cl, F, O=, OH, S—SR, linear or branched alkyl, aryl, linear or branched alkylaryl, linear or branched alkoxy, linear or branched acyloxy or linear or branched hydroxyalkyl; wherein $R_6$ is H, Br, Cl, F, $CO_2H$, OH, S—SR', linear or branched alkyl, aryl, linear or branched alkylaryl, linear or branched alkoxycarbonyl, linear or branched alkoxy or linear or branched hydroxyalkyl; wherein $R_7$ is H, OH, S—SR", or linear or branched alkyl, linear or branched alkoxycarbonyl, linear or branched alkoxy or linear or branched hydroxyalkyl; wherein R, R' and R" are independently the same or different and are linear or branched alkyl, linear or branched acyl or linear or branched alkoxyalkyl; wherein the compound is conjugated to a monoclonal antibody immunoreactive with a determinant site of a cell surface antigen of human tumor cells; wherein the compound is covalently bonded by a cleavable or non-cleavable linker connecting suitable functional groups, respectively, of the compound and the monoclonal antibody; and wherein the linker is selected from a group consisting of glutarate, N-hydroxysuccinic amide ester, a peptide, monosaccharide, oligosaccharide, thioether, disulfide, trisulfide, hydrazide and hydrazone moieties.

The invention also provides a method of treating a tumor in a subject which comprises administering to the subject a therapeutically effective amount of the compound having the structure:

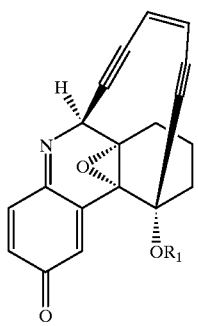

wherein $R_1$ is H, $C_1$–$C_7$ linear or branched chain alkyl, $C_1$–$C_7$ linear or branched chain alkoxyalkyl, $C_1$–$C_7$ linear or branched chain (aryl)alkyl, $C_1$–$C_7$ linear or branched chain (hydroxy)alkyl, $C_1$–$C_7$ linear or branched chain (acyloxy) alkyl, $C_1$–$C_7$ linear or branched chain alkoxycarbonyl, $C_1$–$C_7$ linear or branched chain (aryloxy)alkyl, $C_1$–$C_7$ linear or branched chain acyl, aryl or $(CH_2)_jP(=O)(OH)_2$, where j is an integer from 0 to about 9; wherein the compound is conjugated to a monoclonal antibody immunoreactive with a determinant site of a cell surface antigen of human tumor cells; wherein the compound is covalently bonded by a cleavable or non-cleavable linker connecting suitable functional groups, respectively, of the compound and the monoclonal antibody; and wherein the linker is selected from a group consisting of glutarate, N-hydroxysuccinic amide ester, a peptide, monosaccharide, oligosaccharide, thioether, disulfide, trisulfide, hydrazide and hydrazone moieties. In one embodiment, the invention provides a method wherein $R_1$ is H.

The invention also provides a method wherein the tumor is a solid tumor, and the conjugate is administered by direct injection.

The present invention therefore provides a method of treating cancer, which comprises administering an anticancer-effective quantity of any of the analogues of quinone imine enediyne disclosed herein. The drug may be administered to a patient afflicted with cancer by any conventional route of administration, including, but not limited to, intravenous, intramuscular, oral, subcutaneous, intratumoral, intradermal, and parenteral. The anticancer-effective quantity is between 0.002 mg and 10.0 mg per kg of subject body weight.

Pharmaceutical compositions may be constituted into any form suitable for the mode of administration selected. suitable for oral administration include solid forms, such as pills, capsules, granules, tablets, and powders, and liquid forms, such as solutions, syrups, elixers, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectible medium. Carriers are intended to include necessary and inert binders, suspending agents, lubricants, flavorants, sweeteners, preservatives, dyes, and coatings.

Optimal dosages to be administered may be determined by those skilled in the art, and will vary with the particular enediyne quinone imine analogue in use, the strength of the preparation, the mode of administration, and the advancement of the disease condition. Additional factors depending on the particular patient being treated will result in a need to adjust dosages, including patient age, weight, gender, diet, and time of administration.

The following Experimental Details are set forth to aid in an understanding of the invention, and are not intended, and should not be construed, to limit in any way the invention set forth in the claims which follow thereafter.

EXPERIMENTAL DETAILS

General

All air and moisture sensitive reactions were performed in a flame-dried apparatus under a nitrogen atmosphere unless otherwise noted. Air-sensitive liquids and solutions were transferred via syringe or cannula. Unless otherwise noted, all solvents and reagents were commercial grade and were used as sold. The following are exceptions, and are all distilled under nitrogen using the drying methods listed in parentheses: dichloromethane (calcium hydride), benzene (calcium hydride), tetrahydrofuran (sodium/benzophenone ketyl), diethyl ether (sodium/benzophenone ketyl), diisopropylamine (calcium hydride).

Melting points (mp) were uncorrected and performed in soft glass capillary tubes using an Electrothermal series IA9100 digital melting point apparatus. Infrared (IR) spectra were obtained with a Perkin-Elmer 1600 Series Fourier Transform Spectrometer. Samples were prepared as neat films on NaCl plates unless otherwise noted. Proton nuclear magnetic resonance (1H NMR) spectra were determined using a Bruker AMX-400 spectrometer operating at 400 MHz. Carbon nuclear magnetic resonance (13C NMR) spectra were obtained on a Bruker AMX-400 spectrometer operating at 100 MHz with composite pulse decoupling.

High resolution mass spectra (HRMS) were determined by electron impact ionization (EI) on a JEOL JMS-DX 303HF mass spectrometer with perfluorokerosene (PFK) as an internal standard.

Flash chromatography was carried out on silica gel according to the protocol of Still (W. C. Still, et al., *J. Org. Chem.*, 43, 2923 (1978)).

| Abbreviations | |
|---|---|
| All | allyl |
| CI | chemical ionization |
| DMAP | 2-(N,N-dimethylamino)pyridine |
| DDQ | 2,3-dichloro-5,6-dicyanobenzoquinone |
| LDA | lithium diisopropylamide |
| NIS | N-iodosuccinimide |
| PDC | pyridinium dichromate |
| PMB | p-methoxybenzene |
| r.t. | room temperature |
| Tf | trifluoro |
| THF | tetrahydrofuran |
| TSEO | trimethylsilylethyloxy |
| TEOC | trimethylsilylethyloxycarbonyl (also Teoc) |
| TBAF | tetra-n-butylammonium fluoride |
| TBS | t-butyldimethylsilyl |
| TSE | trimethylsilylethyl |

EXAMPLE 1

2-(2,4-Hexadienoxy)-5-methoxybenzaldehyde (44)

To a solution of 5-methoxysalicyl aldehyde 43 (28 g, 0.18 mol) in 300 mL acetone was added 100 g (0.72 mol) of finely ground $K_2CO_3$. To the yellow suspension was added crude sorbyl bromide (prepared from sorbol (37 mL; 0.33 mol) and $PBr_3$ (15 mL; 0.16 mol) on ice-cold ether) and the mixture was refluxed for 30 min when the fluorescent yellow color disappeared. The mixture was allowed to cool to room temperature, filtered, and the filtrate was concentrated and redissolved in ether. The ethereal solution was washed twice with 1 N NaOH and once with saturated brine, dried ($Na_2SO_4$), and concentrated to a small volume. Treatment with hexane gave rise to formation of white crystalline solid which was filtered and dried to give 29 g of 44. The mother liquor was concentrated and chromatographed on silica to give additional 12 g of the product (96%, combined): m.p. 74–75° C. ($Et_2O$-hexane); ir(neat) $v_{max}$2900, 1679, 1669, 1494, 1275, 1158 cm$^{-1}$; $^1$H nmr (300 MHz, CDCl$_3$) δ 10.47 (x, 1 H, CHO), 7.32 (d, J=3.2 Hz, 1 H, H6), 7.10 (dd, J=9.0, 3.2 Hz, 1 H, H4), 6.93 (d, J=9.0 Hz, 1 H, H3), 6.32 (dd, J=15.3, 10.4 Hz, 1 H, diene), 6.08 (dd, J=15.3, 10.4 Hz, 1 H, diene), 5.8–5.7 (m, 2 H, diene), 4.63 (d, J=6.0 Hz, 2 H, CH$_2$OAr), 3.79 (s, 3 H, OCH$_3$), 1.77 (d, J=6.6 Hz, 3 H, methyl); $^{13}$C nmr (75 MHz, DCDl$_3$) δ 189.7, 156.0, 153.8, 134.3, 131.4, 130.4, 125.5, 124.2, 123.6, 115.2, 110.2, 69.9, 55.9, 18.2; MS (20 eV EI). m/e (rel intens) 232 (M$^+$, 3), 152 (100), 137 (9), 81 (83), HRMS (FAB) for $C_{14}H_{16}O_3$, calcd 232.1100, found 232.1098. Anal. Calcd for $C_{14}H_{16}O_3$: C, 72.39; H, 6.95. Found: C, 72.34; H, 6.94.

2-(2,4-Hexadienoxy)-5-methoxycinnamaldehyde (45)

To a flame-dried 500 mL flask was placed NaH (60% in mineral oil, 4 g; 0.10 mol). The mineral oil was removed by washing with pentane and decanting under $N_2$ atmosphere. Charged with 150 mL of anhydrous THF, to the stirred suspension at 0° C. was added triethyl phosphonoacetate (18.2 mL; 0.092 mol) slowly dropwise. After the addition was complete, the mixture was further stirred at room temperature for 30 min to give clear solution, to which was added a solution of 44 (19.5 g; 0.084 mol) in 70 mL THF via a dropping funnel slowly dropwise over a 30 min period. Further stirred at room temperature for another 30 min, THF was removed by rotary evaporation. The residue was diluted by saturated NaHCO$_3$ and extracted 3 time with Et$_2$O. Combined ether layer was washed with saturated brine, dried (MgSO$_4$), and concentrated to give crude cinnamate as a yellowish oil which was pure enough and used directly: ir (neat): $v_{max}$ 2936, 1710, 1632, 1496, 1215, 1171, 1042 cm$^{-1}$, $^1$H nmr (300 MHz, CDCl$_3$) δ 8.00 (d, J=16.2 Hz, 1 H, H2), 7.03 (d, J=2.7 Hz, 1 H, H6$^1$), 6.84 (AB of ABX, Δv=4.3 Hz, $J_{AB}$=9.0 Hz, $J_{BX}$=2.7 Hz, 2 H, H3$^1$ and 4$^1$), 6.48 (d, 16.2 Hz, 1 H, H1), 6.30 (dd, J=15.2, 10.4 Hz, 1 H, diene), 6.08 (dd, J=16.2, 10.4 Hz, 1 H, diene), 5.8–5.7 (m, 2 H, diene), 4.55 (d, J=5.9 Hz, 2 H, CH$_2$OAr), 4.25 (q, J=7.1 Hz, OCH$_2$CH$_3$), 3.77 (s, 3 H, OCH$_3$), 1.76 (d, J=6.6 Hz, 3 H, methyl), 1.33 (t, J=7.1 Hz, 3 H, OCH$_2$CH$_3$).

To a solution of the crude cinnamate from above in 300 mL anhydrous CH$_2$Cl$_2$ at −78° C. was added 1.5 M DiBal (in toluene, 144 mL; 0.22 mol). Stirred at −78° C. for 1 h, the reaction was quenched by cautious addition of 5 mL MeOH before allowed to warm to room temperature. The mixture was poured into 300 mL of ice-water and acidified by conc. HCl with vigorous stirring with external cooling. Organic layer separated, aqueous phase was extracted again with CH$_2$Cl$_2$ and combined organic was dried (MgSO$_4$) and concentrated to ca. 75 mL, which was then diluted with equal volume of hexane and resulting slurry was filtered to collect 13.5 g of the alcohol as a white crystalline solid. Silica gel column chromatography of the concentrated mother liquor gave additional 7 g of the product (94%, combined): m.p. 82–84° C. (toluene-hexane); ir (CDCl$_3$) $v_{max}$ 3610, 2938, 1493, 1212, 1042 cm$^{-1}$; $^1$H nmr (300 MHz, CDCl3) δ 7.00 (d, J=2.9 Hz, 1 H, H6$^1$), 6.93 (d, J=16.0 Hz, 1 H, H3), 6.78 (AB of ABX, Δv=9.7 Hz, $J_{AB}$=8.9 Hz, $J_{BX}$=2.9 Hz, 2 H, H3$^1$ and 4$^1$), 6.37 (dt, J=16.0, 5.9 Hz, 1 H, H2), 6.3–6.0 (m, 2 H, diene), 5.8–5.7 (m, 2 H, diene), 4.51 (d, J=6.0 Hz, 2 H, CH$_2$OAr), 4.33 (d, J=5.9 Hz, 2 H, H1), 3.78 (s, 3H, OCH$_3$), 1.77 (d, J=6.7 Hz, 3H, methyl).

To a stirred solution of oxalyl chloride (5.0 mL; 58 mmol) in 200 mL anhydrous CH$_2$Cl$_2$ at −78° C. was slowly added DMSO (9.4 mL; 130 mmol). As soon as gas evolution subsided, a solution of the above alcohol (12.5 g; 48 mmol) in 30 mL CH$_2$Cl$_2$ was added via a dropping funnel slowly dropwise over a 30 min period. Further stirred for 30 min at −78° C., triethylamine (33 mL; 240 mmol) was added and the mixture was allowed to warm to ambient temperature over 15 min before quenched by 300 mL of HCl. Organic phase separated, aqueous phase was extracted twice with CH$_2$Cl$_2$ and combined organic was washed with saturated aqueous NaHCO$_3$, dried (MgSO$_4$), and concentrated to ca. 50 mL by rotary evaporation. Resulting suspension was diluted by equal volume of hexane to precipitate out the product which was collected and dried to give 9.4 g of 45 as a yellow crystalline solid. The mother liquour was concentrated and chromatographed on silica to give additional 2 g of 45 (926%, combined): m.p. 82–84° C. (CH$_2$Cl$_2$-hexane); ir (CDCl$_3$) $v_{max}$2915, 2836, 1672, 1620, 1494, 1285, 1210, 1131 cm$^{-1}$; $^1$H nmr (300 MHz, CDCl$_3$) δ 9.69 (d, J=7.8 Hz, 1 H, CHO), 7.85 (d, J=16.1 H, H3), 7.06 (d, J=2.9 Hz, 1 H, H6$^1$), 7.10 (dd, J=9.0, 2.9 Hz, 1 H, H4$^1$), 6.87 (d, J=9.0 Hz, 1 H, H3$^1$), 6.73 (dd, J=16.1, 7.8 Hz, 1 H, H2), 6.31 (dd, J=15.2, 10.5 Hz, 1 H, diene), 6.10 (dd, J=15.2, 10.5 Hz, 1 H, diene), 5.8–5.7 (m, 2 H, diene), 4.58 (d, J=4.1 Hz, 2 H, CH$_2$OAr), 3.79 (s, 3 H, OCH$_3$), 1.77 (d, J=6.7 Hz, 3 H, methyl); 13C nmr (75 MHz, CDCl$_3$) δ 194.5, 153.6, 151.9, 147.9, 134.3, 131.4, 130.5, 129.0, 124.5, 123.9, 118.6, 114.3, 112.6, 69.8, 55.8, 18.2 ; Anal. Calcd for $C_{16}H_{18}O_3$: C, 74.40; H, 7.02. Found: C, 74.14; H, 7.05.

6-Methoxy-3-methyl-3,4,4a,9,10,10a-hexahydro-9-oxaphenanthrene-4-carbaldehyde (A) Thermal Reaction: A solution of 45 (10.0 g; 38.7 mmol) in 250 mL anhydrous toluene was heated to 80° C. for 5 days. Cooled to room temperature, solvent was rotary-evaporated, and the residue was chromatographed on silica to give 9.3 g of 46 (inseparable mixture of endo:exo=ca. 3:1 by nmr) as a yellowish oil (93%). (B) ZnCl$_2$— Catalyzed Reaction: To a solution of 45 (150 mg; 0.58 mmol) in 3 mL anh. CH$_2$Cl$_2$ was added 1 M ZnCl$_2$ (in either, 0.60 mL; 0.60 mmol). The mixture was stirred at room temperature for 3 days, diluted by aqueous NH$_4$Cl, and extracted twice with CH$_2$Cl$_2$. Combined organic was dried (Na$_2$SO$_4$), concentrated, and chromatographed on silica to give 88 mg of 46a (endo:exo=ca. 20:1 by $^1$H nmr) as a yellowish oil (59%): ir (neat) $v_{max}$ 2963, 2721, 1720, 1495, 1210, 1048 cm$^{-1}$; $^1$H nmr (300 MHz, CDCl$_3$ ) δ 10.01 (d, J=4.3 Hz, 1 H, CHO), 6.72 (AB of ABX, Δv=13.3 Hz, $J_{AB}$=8.8 Hz, $J_{BX}$=2.7 Hz, 2 H, H12,13), 6.42 (d, J=2.7 Hz, 1 H, H10), 5.85 (ddd, J=9.8, 4.3, 2.7 Hz, 1 H, H4 or 5), 5.59 (dt, J=9.8, 1.8 Hz, 1 H, H4 or 5), 4.41 (dd, J=10.1, 5.0 Hz, 1 H, H2), 3.96 (dd, J=12.2, 10.1 Hz, 1 H, H2), 3.70 (s, 3 H, OCH$_3$), 3.12 (app t, J=10.9 Hz, 1 H, H8), 2.91 (ddd, J=10.9, 6.7, 4.3 Hz, 1 H, H7), 2.78 (m, 1 H, H3), 2.44 (m, 1 H, H6), 1.14 (d, J=7.2 Hz, 3 H, 6—CH$_3$); $^{13}$C nmr (75 MHz, CDCl$_3$) δ 206.2, 153.4, 148.7, 134.0, 126.9, 124.5, 117.2, 113.1, 111.4, 71.1, 55.8, 52.2, 36.9, 34.3, 32.2, 16.9; HRMS (FAB) for $C_{16}H_{18}O_3$, calcd 258.1256, found 258.1238. Anal. Calcd for $C_{16}H_{18}O_3$: C, 74.40; H, 7.02. Found: C, 74.60; H, 6.89.

9- (1,4-Benzoquinonyl)-2-hydroxy-8-methyl-3-oxabicyclo [3.3.1]non-6-ene (49a)

To a solution of 46 (11.0 g; 42.6 mmol, ca. 3:1 diastereomeric mixture) in 100 mL MeCN at 0° C. was added aqueous solution of ammonium cerium nitrate (60 g; 109 mmol) in 200 mL H$_2$O rapidly dropwise. The initially black solution became orange as yellow solid precipitated at the end of the addition. Stirred at 0° C. for 30 min, the solid was collected by filtration and air-dried to give 6.9 g of 49a as a yellow solid (62%): m.p.>176° C. (dec); ir (CDCl$_3$) $v_{max}$ 3601, 2964, 1657, 1602, 1287, 1080 cm$^{-1}$; $^1$H nmr (300 MHz, CDCl$_3$) δ 6.80 (s, 1 H, H3), 6.73 (AB of ABX, Δv=18.6 Hz, J$_{AB}$=10.1 Hz, J$_{BX}$=2.2 Hz, 2 H, H5, 6), 5.73 (AB of ABX, Δv=30.3 Hz, J$_{AB}$=10.1 Hz, J$_{AX}$32 5.3 Hz, 2 H, H4$^1$, 5$^1$), 5.39 (s, 1 H, acetal), 4.22 (dd, J=10.6, 1.3 Hz, 1 H, —CH$_2$O—), 3.73 (s, 1 H, H1$^1$), 3.45 (dd, J=10.6, 1.5 Hz, 1 H, —CH$_2$O—), 2.74 (br s, 1 H, —OH), 2.25–2.10 (m, 3 H, H2$^1$, 3$^1$, 6$^1$), 1.08 (d, J=7.2 Hz, 3 H, 3$^1$—CH$_3$); 13C nmr (75 MHz, CDCl$_3$) δ 187.9, 187.3, 148.9, 137.4, 135.9, 134.4, 132.6, 123.6, 91.9, 63.8, 41.1, 33.6, 32.8, 30.2, 17.2. Anal. Calcd for C$_{15}$H$_{16}$O$_4$: C, 69.22; H, 6.20. Found: C, 68.84; H, 6.05.

2- (t-Butyldimethylsilyl)oxy-10-[(t-butyldimethylsil-yl)oxy]methyl-7-methyl-7-10-dihydrophenanthridine To a suspension of 49a (5.8 g; 22.3 mmol) in 20 mL AcOH was added a solution of NH$_4$OAc (12 g; 156 mmol) in 20 mL water. The mixture was heated to 100° C. with stirring under N$_2$ atmosphere for 1 h. Resulting dark solution was cooled to 0° C. and neutralized by NH$_4$OH until basic under continuous stream of nitrogen. After further stirred for 1 h at 0° C. with N$_2$ stream maintained, the precipitate was filtered, washed 3 times with water, and air-dried to give 5 g of greenish tan powder, which was dissolved in 10 mL DMF, cooled to 0° C., and 7.1 g of imidazole (91 mmol) and 7.8 g of TBSCl (49 mmol) was added. Stirred for 2 h, diluted by water, extracted 3 times with Et$_2$O, the ether layer was washed with saturated brine, dried (Na$_2$SO$_4$), concentrated, and chromatographed to give 9.0 g of 50 as a slightly tan viscous oil (86%): ir (neat) $v_{max}$ 2950, 1617, 1503, 1254, 1101, 837 cm$^{-1}$; $^1$H nmr (300 MHz, CDCl$_3$) δ 8.60 (s, 1 H, H2), 7.96 (d, J=8.9 Hz, 1 H, H13), 7.38 (d, J=2.5 Hz, 1 H, H10), 7.23 (dd, J=8.9, 2.5 Hz, 1 H, H12), 6.18 (dd, J=9.8, 4.4 Hz, 1 H, H6), 6.08 (dd, J=9.8, 4.5 Hz, 1 H, H5), 4.2–4.0 (m, 2 H, H7, one of CH$_2$O TBS), 3.7–3.5 (m, 2 H, H4, one of CH$_2$OTBS), 1.41 (d, J=7.2 Hz, 3 H, 4-CH$_3$), 1.03 (s, 9 H), 0.85 (s, 9 H), 0.27 (s, 6 H), –0.1 (s, 3 H), –0.3 (s, 3 H), $^{13}$C nmr (75 MHz, CDCl$_3$) δ 154.0, 149.2, 142.8, 137.8, 133.8, 131.4, 131.1, 127.5, 127.1, 123.9, 110.8, 69.4, 39.2, 33.5, 26.0, 25.8, 25.2, 18.5, 18.3, –4.2, –5.3; HRMS (FAB) for C$_{27}$H$_{44}$NO$_2$Si$_2$ (M+H), calcd 470.2911, found 470.2913. Anal. Calcd for C$_{27}$H$_{43}$NO$_2$Si$_2$: C, 69.03; H, 9.23; N, 2.98. Found: C, 68.08; H, 9.49; N, 3.00.

2-(t-Butyldimethylsilyl)oxy-10-[(t-butyldimethylsil-yl)oxy] methyl-8, 9-dihydroxy-7-methyl-7,8,9,10-tetrahydrophenanthridine 50a To a solution of 50 (9.0 g; 19 mmol) in 30 mL of THF and 12 mL of t-BuOH was added 0.2 M OsO$_4$ (in THF, 0.5 mL; 0.1 mmol) and 60% aq NMO (5 mL; 48 mmol). The mixture was stirred at room temperature for 4 h, concentrated to a small volume (ca. 5 mL), and diluted by 5 mL of 10% NaHSO$_3$ and 50 mL of satd NaHCO$_3$. Resulting precipitate was collected, washed thoroughly with water, air-dried, and finally washed with hexane to give 8.93 g of slightly tan powder (50a; 90%) which was pure enough to be used in subsequent reactions. Analytical sample was prepared by recrystallization from hexane-ethyl acetate: m.p. 206–209° C. (hexan-EtOAc); ir (neat) $v_{max}$ 3600, 2931, 1617, 1505, 1260, 1238, 1110 cm$^{-1}$; $^1$H nmr (300 MHz, CDCl$_3$) δ 8.63 (s, 1 H, H2), 7.94 (d, J=8.9 Hz, 1 H, H13), 7.28 (d, J=2.5 Hz, 1 H, H10), 7.21 (dd, J=9.0, 2.4 Hz, 1 H, H12), 4.49 (app t, J=2.8 Hz, 1 H, H6), 4.13 (dd, J=8.9, 2.5 Hz, 1 H, CH$_2$OTBS), 3.99 (dd, J=7.2, 2.5 Hz, 1 H, H5), 3.72 (app dt, J=8.9, 2.8 Hz, 1 H, H7), 3.65 (app t, J=8.9 Hz, 1 H, CH$_2$OTBS), 3.10 (app quint, J=7.2 Hz, 1 H, H4), 1.55 (d, J=7.2 Hz, 3 H, 4-CH$_3$), 1.02 (s, 9 H), 0.83 (s, 9 H), 0.25 (s, 6 H), –0.02 (s, 3 H), –0.07 (s, 3 H); $^{13}$C nmr (75 MHz, CDCl$_3$) δ 154.2, 148.5, 142.7, 136.2, 132.6, 131.4, 127.9, 127.1, 124.1, 110.5, 72.4, 70.9, 65.3, 45.6, 36.0, 25.9, 25.8, 18.5, 18.3, –4.2, –5.4; MS (20 eV EI) m/e (rel intens) 446 (40, M-$^t$Bu), 428 (39), 336 (23), 324 (25), 312 (100); HRMS (FAB) for C$_{27}$H$_{46}$NO$_4$Si$_2$ (M+H), calcd 504.2965, found 504.2979. Anal. Calcd for C$_{27}$H$_{45}$NO$_4$Si$_2$: C, 64.37; H, 9.00; N, 2.78. Found: C, 64.18; H, 9.01; N, 2.64.

Compound 55

To a solution of 6g (12.52 mmol) of diol 50a from the previous step in 70 ml of dichloromethane was added 11.42g (50 mmol) of dimethoxydiphenylmethane followed by 3.1 g (16.28 mmol) of p-toluenesulfonic acid. The resulting solution was refluxed for three hours, cooled to r.t., and extracted with sat. sodium bicarbonate. The aqueous layer was back extracted with ethyl acetate. The combined organic layers were dried over magnesium sulphate, filtered and concentrated to yield a crude mixture of products.

The crude material was taken up in dichloromethane and 1.5 equivalent of imidazole and 1.1 equivalent of t-butyldimethylsilyl chloride were added. The resulting solution was stirred for one hour at r.t. The work-up described above was repeated and the crude product was flash chromatographed on silica gel. Elution with 4/1 hexane-ethyl acetate afforded the desired ketal 55 in 65% yield. See Yoon, T., et al., J. Org. Chem., 59, 3752 (1994).

Compound 9

To a solution of 55 (6.4 mmol) in THF (60 ml) at –78° C. was added (12.8 mmol) of triisopropyl silyl acetylene magnesium bromide. Then was added allyl chloroformate (19 mmol) dropwise. The reaction was then warmed to –30° C. overnight. After which time, the reaction was quenched with saturated ammonium chloride and diluted with ether. The reaction was then extracted with ether and washed with brine. The organic layer was then dried with magnesium sulfate and filtered and concentrated in vacuo. The crude product 9 was then used in the next reaction without purification.

Compound 9a

To a solution of 9 in THF (40ml) at room temperature was added concentrated HCl (1 ml). After one hour, the reaction was neutralized by the addition of saturated NaHCO$_3$ and extracted with ether. The organic layer was then dried with magnesium sulfate and filtered and concentrated in vacuo. The crude product 9a was then purified by silica gel chromatography. The overall yield from 55 to 9a was 4.345 g (82%).

Compound 9b

To a solution of oxalyl chloride (8 mmol) in CH$_2$Cl$_2$ (60 ml) at –78° C. was added DMSO (1.7 mmol). After ten minutes, the alcohol 9a was added as a solution in CH$_2$Cl2 dropwise. After an additional 15 minutes, triethylamine (26.5 mmol) was added and stirred for an additional 15 minutes. After which time, water was added to the reaction at –78° C. and then allowed to warm to room temperature. The reaction was then extracted with CH$_2$Cl$_2$ and dried over magnesium sulfate, filtered and then concentrated in vacuo. To a solution of CH$_2$Cl$_2$ (30 ml) at 0° C. was added triphenyl phosphine (7 g) then carbon tetrabromide (4.4 g) after ten minutes a solution of the crude aldehyde from above was added to the ylide dropwise via syringe over a period of ten minutes. After ten minutes, a solution of saturated NaHCO$_3$ was added. The reaction was then extracted with methylene chloride and dried over Na$_2$SO$_4$. The organic layer was then filtered and concentrated in vacuo and exposed to silica gel chromatography. This yielded (3.84 g) of the dibromide 9b (75%).

$^1$H NMR (400 MHz, CDCl$_3$): δ 7.55 (m, 3H), 7.38 (m, 3H), 7.08 (m, 4H), 6.75 (dd, 1H), 6.55 (d, 1H), 6.28 (d, 1H), 5.97 (m, 1H), 5.35 (d, 1H), 5.21 (d, 1H), 4.70 (m, 2H), 4.20 (dd, 1H), 3.91 (d, 1H), 2.90 (m, 1H), 1.45 (d, 3H), 0.95 (s, 9H), 0.82 (s, 18H), 0.31 (s, 6H).

Compound 9c

To a solution of 9b in toluene (60 ml) at −78° C. was added n-butyllithium (8.3 mmol) dropwise via syringe pump. After six hours at −78° C., the reaction was warmed to −65° C. for one hour. After which time, the reaction was quenched by the addition of acetic acid and diluted with ether. The organic layer was then extracted with ether and dried over magnesium sulfate, filtered, and concentrated in vacuo. The crude product was then exposed to silica gel chromatography. This yielded (2.72 g) of the acetylene 9c (85%).

$^1$H NMR (400 MHz, CDCl$_3$): δ 7.52 (m, 3H), 7.39 (m, 3H), 7.01–7.18 (m, 4H), 6.93 (d, 1H), 6.72 (dd, 1H), 5.93 (m, 1H), 5.68 (brs, 1H), 5.33 (dT, 1H), 5.20 (d, 1H), 4.71 (d, brs, 2H), 4.31 (d, 1H), 3.90 (s, 1H), 2.92 (brs, 1H), 2.13 (d, 1H), 1.49 (d, 3H), 0.99 (s, 6H), 0.87 (m, 18H), 0.22 (d, 6H).

Compound 9d

To a solution of 9c (3.34 mmol) in THF (20 ml) at 0° C. was added 1M TBAF (8.4 mmol). After two hours at 0° C., saturated ammonium chloride and ether was added and the reaction was extracted with ether. The organic layer was dried over magnesium sulfate, filtered, and concentrated in vacuo. The crude alcohol was then dissolved in methanol (25 ml) and concentrated HCl (5 ml) was added. The reaction was then refluxed for two hours. After which time, the reaction was allowed to cool and water was added, followed by CH$_2$Cl$_2$. The reaction was extracted with CH$_2$Cl$_2$, dried over magnesium sulfate, filtered, and concentrated in vacuo. The crude product was then exposed to silica gel chromatography to yield (1.14 g) of triol 9d (90%).

Compound 9e

To a solution of 9d (1.14 g) in THF (20 ml) at room temperature was added NaH (240 mg, 60%). After ten minutes tertButyldimethylsilylchloride (680 mg) was added. After 30 minutes, the reaction was diluted with ether and water was added. The reaction was extracted with ether and washed with brine and the organic layer was dried with magnesium sulfate, filtered, and concentrated in vacuo. The product was then exposed to silica gel chromatography to yield (1.16 g) of 9e (78%).

$^1$H NMR (400 MHz, CDC$_{13}$): δ 7.43 (brs, 1H), 7.24 (d, 1H), 6.76 (dd, 1H), 5.93 (m, 1H), 5.71 (brs, 1H), 5.31 (d, 1H), 5.24 (d, 1H), 4.74 (dd, 1H), 4.70 (brs, 1H), 4.21 (s, 1H), 3.92 (dd, 1H), 3.52 (s, 1H), 2.52 (m, 1H), 2.36 (d, 1H), 2.12 (d, 1H), 1.42 (d, 3H), 0.95 (s, 9H), 0.22 (s, 6H).

Compound 11

To a solution of 9e (670 mg) in CH$_2$Cl$_2$ (30 ml) at room temperature was added (1.1 eq.) acetic anhydride. After 12 hours, the reaction was diluted with CH$_2$Cl$_2$ and water and NaHCO$_3$. The reaction was extracted with CH$_2$Cl$_2$, dried over magnesium sulfate, filtered, concentrated in vacuo. The crude diacetate was then dissolved in THF (14 ml) at 0° C. and morpholine (2.5 mmol) was added. Then Pd(PPh$_3$)$_4$ (30 mg) was then added. After a period of 2.5 hours, the reaction was warmed to room temperature for 30 minutes. Then the reaction was cooled to 0° C. and NaH (170 mg) was added followed by the addition of trimethylsilylethoxycarbonylchloride (760 mg). After six hours, the reaction was diluted with water and ether, extracted with ether and dried over magnesium sulfate, filtered, and concentrated in vacuo. Following silica gel chromatography (823 mg) of 11 was obtained (85%).

$^1$H NMR (400 MHz, CDCl$_3$): δ 7.45 (brs, 1H), 7.22 (d, 1H), 6.78 (dd, 1H), 5.50 (brs, 1H), 5.49 (t, 1H), 5.31 (dd, 1H), 4.36 (m, 1H), 4.29 (m, 1H), 2.79 (m, 1H), 2.45 (d, 1H), 2.13 (d, 1H), 2.13 (s, 3H), 2.05 (s, 3H), 1.34 (d, 3H), 1.08 (t, 3H), 0.90 (s, 9H), 0.22 (s, 6H), 0.03 (s, 3H).

Compound 11a

To a solution of 11 (810 mg) in a THF-MeOH (10:1; 11 ml) solution at 0° C. was added N$_2$H$_4$ (200 µl). After two hours at 0° C. and three hours at room temperature, an additional (300 µl) of N$_2$H$_4$ was added. After an additional three hours, the reaction was diluted with water and ether and extracted with ether. The organic layer was dried over magnesium sulfate, filtered, and concentrated in vacuo to yield after silica gel chromatography (750 mg) of the diol 11a (90%).

$^1$H NMR (400 MHz, CDCl$_3$): δ 7.46 (brs, 1H), 7.21 (d, 1H), 6.74 (dd, 1H), 5.64 (brs, 1H), 4.33 (m, 2H), 4.22 (s, 1H), 3.92 (d, 1H), 3.53 (s, 1H), 2.51 (m, 1H), 2.33 (d, 1H), 2.11 (d, 1H), 1.45 (d, 3H), 1.07 (t, 2H), 0.97 (s, 9H), 0.23 (s, 6H), 0.01 (s, 3H).

Compound 11b

To a solution of 11a (626 mg) in CH$_2$Cl$_2$ (20 ml) at room temperature was added m-chloroperbenzoic acid (800 mg). After nine hours, the reaction was diluted with EtOAc and NaHCO$_3$ was added. Then enough dimethylsulfide was added to reduce the remaining m-chloroperbenzoic acid. After ten minutes, the reaction was extracted with EtOAc and dried over magnesium sulfate, filtered, and concentrated in vacuo. Following silica gel chromatography (470 mg) of 11b (73%) was obtained.

$^1$H NMR (400 MHz, CDCl$_3$): δ 7.38 (d, 1H), 7.20 (brs, 1H), 6.83 (dd, 1H), 5.58 (brs, 1H), 4.28 (m, 2H), 4.18 (brs, 1H), 4.07 (dt, 1H), 3.84 (t, 1H), 3.78 (dt, 1H), 3.42 (d, 2H), 2.36 (d, 1H), 2.35 (m, 1H), 2.20 (d, 1H), 2.12 (brs, 1H), 1.59 (d, 3H), 0.70 (9H), 0.21 (d, 6H), 0.00 (s, 3H).

Compound 11c

To a solution of 11b (102 mg) in THF at room temperature was added silver (I) nitrate (3.1 mg) followed by N-iodosuccinamide (111 mg). After three hours, water was added and the reaction was diluted with EtOAc. The reaction was extracted with EtOAc and washed with brine. The organic layer was then dried over magnesium sulfate, filtered, and concentrated in vacuo to yield after silica gel chromatography, 11c (128 mg, (86%)).

$^1$H NMR (400 MHz, CDCl$_3$): δ 7.19 (brs, 1H), 7.18 (d, 1H), 6.84 (dd, 1H), 5.7.5 (brs, 1H), 4.24 (m, 1H), 4.07 (dt, 1H), 3.97 (d, 1H), 3.79 (m, 1H), 3.42 (d, 1H), 2.37 (m, 1H), 2.22 (d, 1H), 1.58 (d, 3H), 1.00 (s, 12H), 0.27 (d, 6H), 0.01 (s, 3H).

Compound 12

To a solution of 11c (128 mg) in dimethylformamide (15 ml) at 70° C. was added Pd(PPh$_3$)$_4$ (9 mg). Then a (0.023 M) solution of cis-1,2-bistrimethylstannylethylene in DMF was added dropwise via syringe pump over one hour. After which time, the reaction was allowed to cool to room temperature, diluted with ether and extracted with water (5×). The organic layer was then washed with brine, dried over magnesium sulfate, filtered, and concentrated in vacuo. Following silica gel chromatography (65 mg) of the enediyne 12 (81%) was obtained.

$^1$H NMR (400 MHz, CDCl$_3$): δ 7.20 (brs, 1H), 6.97 (d, 1H), 6.78 (dd, 1H), 5.75 (brs, 1H), 5.74 (dd, 1H), 5.70 (dd, 1H), 4.30 (m, 1H), 4.24 (brs, 1H), 4.11 (dt, 1H), 4.04 (dd, 1H), 3.79 (ddd, 1H), 3.33 (d, 1H), 2.48 (m, 1H), 2.33 (d, 1H), 1.51 (d, 3H), 1.05 (m, 2H), 0.09 (s, 9H), 0.20 (d, 6H), 0.00 (s 3H).

Compound 7

To a solution of 12 (150 mg) in CH$_2$Cl$_2$ at room temperature was added pyridine (478 µl), acetic anhydride (200 µl), dimethylaminopyridine (5 mg). After a period of 24 hours, the reaction was diluted with EtOAc and saturated NaHCO$_3$ was added. The reaction was extracted with EtOAc, washed with brine, dried over magnesium sulfate, filtered, and concentrated in vacuo. Following silica gel chromatography (162 mg) of 7 (93%) was obtained.

$^1$H NMR (400 MHz, CDCl$_3$): δ 7.18 (brs, 1H), 6.92(d, 1H), 6.70 (dd, 1H), 5.80 (brs, 1H) 5.75 (d, 1H), 5.68 (d, 1H), 5.48 (t, 1H), 5.30 (dd, 1H), 4.32 (m, 1H), 4.20 (brs, 1H), 3.96 (d, 1H), 2.80 (m, 1H), 2.05 (s, 3H), 2.11 (s, 3H), 1.42 (d, 3H), 1.05 (m, 2H), 1.01 (s, 9H), 0.22 (d, 6H), 0.02 (s, 3H).

Compound 6

To a solution of 7 (107 mg) in THF (5 ml) at 0° C. was added TBAF (430 μl, 1M). After 4 h, iodobenzenediacetate (255 mg) was added and the reaction allowed to stir for an addition 30 m. After which time the reaction was diluted with EtOAc and water. The reaction was extracted with EtOAc, dried over magnesium sulfate, filtered, concentrated in vacuo, and subjected to silica gel chromatography to yield (36 mg) of 6 (55%).

$^1$H NMR (400 MHz, CDCl$_3$): δ 7.15 (d, 1H), 6.60 (d, 1H), 6.51 (dd, 1H), 5.91 (dd, 1H), 5.87 (dd, 1H), 5.50 (t, 1H), 5.40 (s, 1H), 5.27 (dd, 1H), 3.79 (d, 1H), 2.80 (m, 1H), 2.10 (s, 3H), 2.04 (s, 3H), 1.38 (d, 3H). LRMS [CI, NH$_4$] m/z 409 ([M+H]) 100%)

Compound 12a

To a solution of 12 (220 mg) in CH$_2$Cl$_2$ at −78° C. was added pyridine (1.2 ml) followed by the addition of trifluoromethanesulfonic anhydride (113 μl). After 5m, the reaction was warmed to −20° C. and stirred for 1.3 h. After which time, water and CH$_2$Cl$_2$ were added. The organic layer was washed with 1N HCl, followed by saturated NaHCO$_3$. The organic layer was then dried over Na$_2$SO$_4$ followed by filtration and concentration in vacuo. The crude product was then chromatographed to yield (248 mg) of 12a (93%).

Compound 12b

To a solution of 12a (248 mg) in CH$_2$Cl$_2$ at room temperature was added the Dess-Martin periodinate (440 mg). After a period of 1.5 h, the reaction was diluted with CH$_2$C$_{12}$ and saturated NaHCO$_3$. The organic layer was extracted with CH$_2$Cl$_2$ and dried over magnesium sulfate, filtered and concentrated in vacuo. Following silica gel chromatography, (235 mg) of 12b (95%).

$^1$H NMR (400 MHz, C$_6$D$_6$): δ 7.28 (brs, 1H), 6.75 (m, 2H), 6.00 (brs, 1H), 5.61 (d, 1H), 4.89 (d, 1H), 4.95 (d, 1H), 4.25 (m, 2H), 4.12 (s, 1H), 2.57 (m, 1H), 1.21 (d, 3H), 0.87 (t, 2H), 0.90 (s, 9H), 0.11 (d, 6H), −0.14 (s, 3H).

Compound 14

To a solution of CrCl$_2$ (853 mg) in THF (12 ml) was added a solution of 12b in THF (12 ml). After 1.2 h, the reaction was diluted with CH$_2$Cl$_2$ and saturated NaHCO$_3$. The reaction was extracted with CH$_2$Cl$_2$ and washed with water and brine and then the organic layer was dried over magnesium sulfate, filtered, and concentrated in vacuo to yield after silica gel chromatography (173 mg) of 14 (87%) which was stored frozen in benzene.

$^1$H NMR (400 MHz, C$_6$D$_6$): δ 7.26 (brs, 1H), 6.81 (m, 2H), 6.01 (brs, 1H), 4.90 (d, 1H), 4.87 (d, 1H), 4.21 (m, 2H), 4.11 (s, 1H), 2.51 (brs, 1H), 2.4–2.37 (m, 2H), 1.20 (d, 3H), 1.01 (s, 9H), 0.85 (t, 2H), 0.15 (d, 6H), −0.21 (s, 3H).

Compound 15

To a solution of MgBr$_2$ (277 mg) in acetonitrile (5 ml) was added triethylamine (343 μl) and was bubbled CO$_2$ for 10 m. Then a solution of 14 in acetonitrile (3 ml) was added dropwise to the reaction. After a period of 5 h, the reaction was diluted with ether, washed with NaHCO$_3$ and dried over Na$_2$SO4, filtered and concentrated in vacuo. The crude acid was then diluted with THF (5 ml) and then diisopropylethylamine (214 μl) was added followed by chloromethyl methylether (25 μl) at room temperature. After 10 m, the reaction was diluted with EtOAc, washed with NaHCO$_3$, dried over magnesium sulfate, filtered and concentrated in vacuo to yield after silica gel chromatography (10 mg) of 15 (30%).

$^1$H NMR (400 MHz, CDCl$_3$): δ 12.95 (s, 1H), 7.34 (brs, 1H), 7.10 (d, 1H), 6.87 (dd, 1H), 6.21 (brs, 1H), 5.10–5.29 (m, 3H), 4.81 (d, 1H), 4.20–4.40 (m, 4H), 3.96 (brs, 1H), 2.92 (s, 3H), 1.41 (d, 3H), 1.02 (s, 9H), 0.87 (t, 2H), 0.17 (d, 6H), −0.10 (s, 3H).

Compound 15a

To a solution of 15 (20 mg) in anhydrous methanol (3 ml) was added (trimethylsilyl) diazomethane (10 eq., 2M in hexane). After a period of 3 h, the reaction was concentrated in vacuo and exposed to silica gel chromatography to yield (15 mg) of 15a (70%).

$^1$H NMR (400 MHz, CDCl$_3$): δ 7.20 (brs, 1H), 6.95 (d, 1H), 6.78 (dd, 1H), 5.75 (d, 1H), 5.69 (brs, 1H), 5.68 (d, 1H1), 5.40 (d, 1H), 5.32 (d, 1H), 4.24, (m, 2H), 4.18 (s, 1H), 3.90 (s, 3H), 3.80 (9, 1H), 3.51 (s, 3H), 1.43 (d, 3H), 1.00 (s, 11H), 0.20 (d, 6H), 0.15 (s, 3H).

Compound 17

To a solution of 15a (10 mg) in THF was placed TBAF (75 μl) at 0° C. After a period of 3 h, iodobenzene(diacetate) (24 mg) was added. After an additional 30 m, the reaction was diluted with water and EtOAc, extracted with EtOAc, dried over magnesium sulfate, and concentrated in vacuo. Following silica gel chromatography (3.3 mg) of 17 was obtained (55%).

$^1$H NMR (400 MHz, CDCl$_3$): δ 7.20 (d, 1H), 6.63 (d, 1H), 6.55 (dd, 1H), 5.90 (q, 2H), 5.42 (d, 1H), 5.37 (s, 1H), 5.30 (m, 1H), 4.02 (s, 1H), 3.89 (s, 3H), 3.78 (q, 1H), 3.51 (s, 3H), 1.42 (d, 3H).

Diacetate 12a

A 100 ml recovery flask was charged with the acetate 10a (4.36 mmol, 1.0 g) in CH$_2$Cl$_2$ (20 ml). The solution was cooled to 0° C. and mCPBA (42%) (6.1 mmol, 2.51 g) was added. The solution was stirred for 3 h under Ar and was slowly warmed to room temperature. Upon completion of the reaction (CH3)2S (0.4 ml) was added and the resulting solution was stirred for 30 minutes. NaHCO$_3$ (100 ml) was then added and the organic layer was extracted with CH$_2$Cl$_2$ (100 ml). The organic layer was separated, dried (MgSO$_4$), filtered and concentrated. The N-oxide 11a was obtained as a crude oil.

The N-oxide 11a was then immediately subjected to the action of Ac$_2$O (5 ml) and this solution was stirred at 70° C. for 1 h. The reaction was cooled to room temperature and was redissolved in CH$_2$Cl$_2$ (100 ml). Saturated NaHCO$_3$ (100 ml) was added and the organic layer was separated. The solution was washed with brine, dried (MgSO$_4$), filtered and concentrated. Purification by column chromatography (SiO2, 1:1 EtOAc/Hexanes) provided the diacetate 12a as a yellow solid (1.32 g, 84% over 2 steps), mp 95.4° C. $^1$H NMR (400 MHz, CDCl$_3$) d 8.71 (s, 1H), 8.09 (d, 1H, J=9.0 Hz), 7.46 (d, 1H, J=2.4 Hz), 7.39 (dd, 1H, J=2.4 Hz, 9.0 Hz), 6.48 (t, 1H, J=3.5 Hz), 2.8–3.2 (m, 2H), 2.0–2.3 (m, 4H), 2.36 (s, 3H), 2.08 (s, 3H). FTIR (CDCl$_3$)n 2951 (m), 1760 (s), 1730 (s), 1507 (s), 1370 (s) 1014 (s) cm$^{-1}$. HRFABMS calcd. for C$_{17}$H$_{17}$NO$_4$ 299.1157.

Epoxide 14a

A 100 ml recovery flask was charged with a solution of the diacetate 12a (6.5 mmol, 2.0 g) in THF (30 ml). The solution was cooled to −78° C. and was treated with ethynylmagnesium bromide (0.5 M in THF, 6.5 mmol, 13.0 ml). The solution was stirred for 30 min. after which time TEOC—Cl (7.8 mmol, 1.38 ml) was added at −78° C. and the solution was gradually warmed to 0° C. An additional 5 equivalents of ethynylmagnesium bromide and an additional 2 equivalents of TEOC—Cl were added over the course of 5 hr until the reaction was completed. H$_2$O (200 ml) and saturated NaHCO$_3$ (200 ml) were then added and the organic layer was extracted with EtOAc (200 ml), separated, dried (Na$_2$SO$_4$), filtered and concentrated to yield the crude acetylide 13a as a yellow-brown oil.

This crude acetylide 13a was redissolved immediately in CH$_2$C$_{12}$ (15 ml) and was treated with mCPBA (95%, 18.5 mmol, 3.36 g) and was stirred for 2–3 days at room temperature, monitoring the reaction periodically by $^1$H NMR. Upon completion, (CH$_3$)$_2$S (0.8 ml) was added and the solution was stirred for 30 min. Sat. NaHCO$_3$ (100 ml) was added and the organic layer was extracted with CH$_2$C$_{12}$ (100 ml), dried, filtered and concentrated in vacuo. Purification by column chromatography (SiO$_2$, 5:1 Hexanes/

EtOAc) yielded the amber colored epoxide 14a as an oil (1.24 g, 42% over two steps).

$^1$H NMR (400 MHz, CDCl$_3$) d 7.35 (br s, 1H), 7.05 (buried dd, 1H), 7.05 (buried d, 1H), 5.75 (dd, 1H, J=6.1 Hz, 9.0 Hz), 5.55 (br s, 1H), 4.25 (m, 2H), 2.2 (buried s, 1H), 2.19 (s, 3H), 2.17 (s, 3H), 1.4–2.1 (m, 6H), 0.85 (buried t, 2H), 0.0 (br s, 9H). FTIR (CH$_2$Cl$_2$)n 3450 (m), 2955 (s), 1738 (s), 1508 (s), 1426 (s), 1398 (s), 1315 (s), 1287 (s), 1234 (s), 1188 (s), 934 (s), 861 (s), 839 (s) cm$^{-1}$ HRFABMS calcd. for C$_{25}$H$_{31}$NO$_7$Si Acetate 15a To a solution of the epoxide 14a (14.0 mmol, 6.8 g) in freshly distilled MeOH (100 ml) at −78° C. was added dry KCN (14.0 mmol, 0.91 g). The solution was stirred initially at −78° C. and was then gradually warmed to 0° C. continuing to stir for 2 h. H$_2$O (500 ml) was then added and the product was extracted with EtOAc (500 ml), separated, dried (Na$_2$SO$_4$), filtered, concentrated and azeotroped (3×) from benzene. Column chromatography (SiO$_2$, 10:1 Hexanes/EtOAc) yielded the phenolic alcohol as an oily residue.

The phenolic alcohol was immediately redissolved in dry CH$_2$Cl$_2$ (100 ml) and TBSCl (70 mmol, 10.5 g) and imidazole (70 mmol, 4.76 g) were added and the reaction was stirred at room temperature for 1 h. Upon completion of the reaction H$_2$O (500 ml) and EtOAc (500 ml) were added, the organic layer was separated, dried (Na$_2$SO$_4$), filtered and concentrated. The resulting oil was azeotroped (3×) from benzene and was subsequently chromatographed (SiO$_2$, 10:1 Hexanes/EtOAc) to yield the acetate 15a as a yellow foam (5.2 g, 69% over 2 steps).

$^1$H NMR (400 MHz, CDCl$_3$) d 7.18 (br s, 1H), 6.78 (d, 1H, J=8.8 Hz), 6.75 (d, 1H, J=2.5 Hz), 5.76 (dd, 1H, J=6.01 Hz, 8.6 Hz), 5.56 (br s, 1H), 4.26 (t, 2H, 8.3 Hz), 2.2 (buried d, 1H), 2.10 (s, 3H), 1.6–2.35 (m, 6H), 1.0 (s, 9H), 0.85 (buried t, 2H), 0.18 (s, 3H), 0.17 (s, 3H), 0.0 (s, 9H). FTIR (CH$_2$Cl$_2$)n 3299 (w), 2955 (s), 1732 (s), 1658 (sh), 1500 (s), 1372 (s), 1315 (s), 1287 (s), 1234 (s), 1180 (s), 1064 (s), 1045 (s), 934 (s), 861 (s) cm$^{-1}$. HRFABMS calcd. for C$_{29}$H$_{43}$NO$_6$Si$_2$ 557.2848.

Ketone 17a

To a solution of the acetate 15a (7.7 mmol, 4.3 g) in CH$_2$Cl$_2$ (100 ml) at −78° C. was added a solution of DIBAL-H (15.4 mmol, 15.4 ml). The solution was stirred at −78° C. for 2 h and MeOH was then added dropwise at −78° C. until the bubbling had stopped. The solution was then warmed to 25° C. and ether (200 ml) and Rochelle salt (200 ml) were added. The solution was stirred for 30 min until the layers became clear. The organic layer was separated, washed with brine (2×), dried (Na$_2$SO$_4$), filtered, concentrated and azeotroped (3×) from benzene to yield the alcohol 16a as a yellow oil. The crude alcohol 16a was redissolved immediately in CH$_2$Cl$_2$ (100 ml) and 4Å dry molecular sieves (3.4 g) and pyridinium chlorochromate (20.4 mmol, 4.4 g) were added. The solution was then stirred under Ar at 25° C. for 3 h, after which time the solution was diluted with ether (100 ml) and filtered through Celite and SiO$_2$, flushing with generous amounts of ether. The solution was concentrated to a dark oil and chromatographed (SiO$_2$ 10:1 Hexanes/EtOAc) to yield the yellow ketone 17a as a foam (1.78 g, 46% over 2 steps).

$^1$H NMR (400 MHz, CDCl$_3$) d 7.86 (d, 1H, J=2.5 Hz), 7.16 (br s, 1H), 6.81 (d, 1H, J=2.5 Hz, 8.6 Hz), 5.65 (br s, 1H), 4.24 (t, 2H, J=8.3 Hz), 2.6–2.7 (m, 1H), 2.51–2.58 (m, 1H), 2.21–2.29 (m, 2H), 2.2 (buried d, 1H), 1.88–2.04 (m, 2H), 1.0 (buried t, 2H), 1.0 (s, 9H)I, 0.24 (s, 3H), 0.18 (s, 3H), 0.0 (s, 9H). FTIR (CH$_2$Cl$_2$)n 3300 (m), 2956 (s), 2931 (m), 2879 (m), 2858 (m), 1715 (s) 1494 (s), 1313 (s), 1288 (s), 1247 (s) cm$^{-1}$. HRFABMS calcd. for C$_{27}$H$_{39}$NO$_5$Si$_2$ 513.2476.

Enediyne 18a

In a 25 ml recovery flask was placed Pd(PPh$_3$)$_4$ (0.0095 mmol, 0.010 g) in dry degassed (3 h) benzene (1 ml). $^n$BuNH$_2$ (0.76 mmol, 0.076 ml) was then added followed by the chloroenyne (0.62 mmol, 0.098 ml). A solution of the ketone 17a (0.19 mmol, 0.10 g) in benzene (3 ml) was then added to the solution followed by freshly purified CuI (0.038 mmol, 0.0072 g) and the solution was stirred at 25° C. overnight. The solution was then poured into saturated NaHCO$_3$ (50 ml) and was extracted with CH$_2$Cl$_2$ (50 ml). The organic layer was separated, dried (Na$_2$SO$_4$) and concentrated. Column chromatography (Sio$_2$, 100% Hexanes, 20:1 Hexanes/EtOAc, 15:1 Hexanes/EtOAc) yielded 18a as a foamy yellow solid (0.090 g, 75%)

$^1$H NMR (400 MHz, CDCl$_3$) d 7.85 (d, 1H, J=2.74 Hz), 7.15 (br s, 1H), 6.80 (d, 1H, J=6.14 Hz), 5.90 (br s, 1H), 5.78 (d, 1H, J=11.1 Hz), 5.63 (d, 1H, J=11.1 Hz), 4.24 (t, 2H, J=8.3 Hz), 2.6–2.7 (m, 2H), 2.2–2.3 (m, 2H), 1.8–2.0 (m, 2H), 1.02 (s, 9H), 1.0 (buried t, 2H), 0.24 (s, 3H), 0.23 (s, 3H), 0.21 (s, 9H), 0.0 (s, 9H). FTIR (CH$_2$Cl$_2$)n 2957 (s), 2931 (s), 2897 (s), 2144 (w), 1696 (s), 1609 (m), 1578 (m), 1495 (s), 1391 (s), 1117 (s), 938 (s), 860 (s) cm$^{-1}$. HRFABMS calcd. for C$_{34}$H$_{49}$NO$_5$Si$_3$ 636.0298.

Closed Enedivne 20a

In a 100 ml recovery flask was placed 18a (2.2 mmol, 1.4 g) in 1:1:1 THF/EtOH/H$_2$O (50 ml). AgNO$_3$ (1.1 mmol, 0.19 g) was then added and the reaction was stirred for 2 h at 25° C. H$_2$O (100 ml) was then added and the solution was extracted with ether (100 ml). The organic layer was dried (Na$_2$SO$_4$), filtered, concentrated and chromatographed to yield the deprotected enediyne 19a (1.24 g, 90%).

The deprotected enediyne 19a (1.96 mmol, 1.11 g) was then dissolved immediately in freshly distilled toluene (200 ml) and the solution was cooled to −78° C. Freshly prepared LDA (2.9 mmol, 4.99 ml) was then added slowly dropwise. The reaction was stirred under Ar at −78° C. for 1 h. NH$_4$Cl (100 ml) was then added and the solution was warmed to room temperature and H$_2$O (100 ml) was added.

The solution was extracted with EtOAc (100 ml) and the organic layer was separated, dried and concentrated. Column chromatography (Sio$_2$, 10:1 Hexanes/EtOAc) yielded the closed enediyne 20a as a yellow oil (0.78 g, 71%). $^1$H NMR (400 MHz, CDCl$_3$) d 8.10 (d, 1H, J=2.7 Hz), 7.15 (br s, 1H), 6.75 (dd, 1H, J=2.7 Hz, 8.7 Hz), 5.80 (d, 1H, J=10 Hz), 5.65 (dd, 1H, J=1.6 Hz, 10 Hz), 5.4 (br s, 1H), 4.25 (t, 2H, J=8.1 Hz), 2.27 (m 1H), 2.15 (m, 3H), 1.88 (m, 1H), 1.73 (m, 1H), 1.0 (buried t, 2H), 0.96 (s, 9H), 0.20 (s, 3H) 0.19 (s, 3H), 0.0 (s, 9H). FTIR (CH$_2$Cl$_2$)n 3574 (w), 2957 (m), 2927 (m), 2872 (w), 1798 (m), 1650 (s), 1271 (s), 1106 (m) cm$^{-1}$. HRFABMS calcd. for C$_{31}$H$_{41}$NO$_5$Si$_2$ 563.8471.

Quinone Imine 21a

To a solution of the closed enediyne 20a (0.35 mmol, 0.20 g) in THF (10 ml) cooled to 0° C. was added TBAF (1.0 M, 1.76 mmol, 1.76 ml). Immediately the color of the solution changed from light yellow to bright red. The solution was then stirred at 0° C. for 2 h. After removal of the TEOC and TBS groups had been completed as monitored by thin layer chromatography, PhI(OAc)$_2$ (2.47 mmol, 0.79 g) was added and the solution was stirred at 0° C. for 1 h. A solution of saturated NaHCO$_3$ (100 ml) was then added and the solution was extracted with EtOAc (100 ml). The organic layer was dried (Na$_2$SO$_4$) and concentrated. Column chromatography (SiO$_2$ 4:1 Hexanes/EtOAc, 3:2 EtOAc/Hexanes) yielded the quinone imine 21a as a yellow oil. Recrystallization from ether/hexanes yielded the quinone imine 21a as a powdery yellow solid (0.49 g, 49%), mp >125° C.

$^1$H NMR (400 MHz, CDCl$_3$) d 7.69 (d, 1H, J=2.0 Hz), 7.12 (d, 1H, J=10.0 Hz), 6.51 (dd, 1H, J=2.0 Hz, 10.0 Hz), 5.94 (d, 1H, J=10.0 Hz), 5.88 (d, 1H, J=10.0 Hz) 5.13 (s, 1H), 2.05–2.15 (m, 4H), 1.85–1.95 (m, 1H), 1.7–1.8 (m, 1H). FTIR (CH$_2$Cl$_2$)n 3577 (w), 2966 (m), 2930 (m), 2858 (w), 1698 (s), 1496 (s), 1471 (m), 1392 (s), 1314 (s), 1289 (s), 1249 (s) 1199 (s) cm$^{-1}$. HRFABMS calcd. for C$_{19}$H$_{13}$NO$_2$ 287.3209.

Acetoxy Enediyne 22a

To a solution of 20a (0.044 mmol, 0.025 g) in pyridine (5 ml) was added Ac$_2$O (0.22 mmol, 0.021 ml) and a catalytic amount of DMAP. The solution was then stirred for 36 h at 25° C. Upon completion, 1N HCl (10 ml) was then added and the solution was diluted with EtOAc (50 ml), washed with saturated NaHCO$_3$ (50 ml) (2×), brine (50 ml) (1×), dried (Na$_2$SO$_4$) and concentrated. Column chromatography (SiO$_2$, 7:1 Hexanes/EtOAc) yielded 22a as a yellow oil (16.3 mg, 62%).

$^1$H NMR (400 MHz, CDCl$_3$) d 7.37 (d, 1H, J=2.6 Hz), 7.15 (br s, 1H), 6.75 (dd, 1H, J=2.6 Hz, 8.7 Hz), 5.84 (d, 1H, J=10.0 Hz), 5.66 (d, 1H, J=10.0 Hz), 5.4 (br s, 1H), 4.26 (t, 2H, J=8.0 Hz), 2.17 (s, 3H), 1.95–2.45 (m, 6H), 1.0 (buried t, 2H), 0.95 (s, 9H), 0.15 (s, 3H), 0.14 (s, 3H), 0.0 (s, 9H)

Acetoxy Puinone Imine 23a

To a solution of the acetoxy enediyne 22a (0.027 mmol, 16.3 mg) in THF (1 ml) cooled to 0° C. was added TBAF (1.0 M in THF, 0.136 mmol, 0.136 ml). The solution was stirred at 0° C. until the TBS and TMS groups were removed as monitored by thin layer chromatography. PhI(OAc)$_2$ (0.189 mmol, 0.061 g) was then added and the reaction was stirred at 0° C. for 30 min. The solution was diluted with EtOAc (50 ml), washed with NaHCO$_3$ (50 ml) (2×), dried (Na$_2$SO$_4$) and reduced in vacuo. Column chromatography (SiO$_2$ 4:1 Hexanes/EtOAc, 3:2 EtOAc/Hexanes) yielded the acetoxy quinone imine 23a as a yellow oil. Re-crystallization from Et$_2$O and hexanes yielded 23a as a powdery yellow solid (2.4 mg, 27%)

$^1$H NMR (400 MHz, CDCl$_3$) d 7.15 (d, 1H, J=10.0 Hz), 7.02 (d, 1H, J=2.0 Hz), 6.53 (dd, 1H, J=2.0 Hz, 10.0 Hz), 5.99 (d, 1H, J=10.0 Hz), 5.89 (d, 1H, J=10.0 Hz), 5.13 (d, 1H, J=2.0 Hz), 1.7–2.6 (m, 6H), 2.2 (s, 3H).

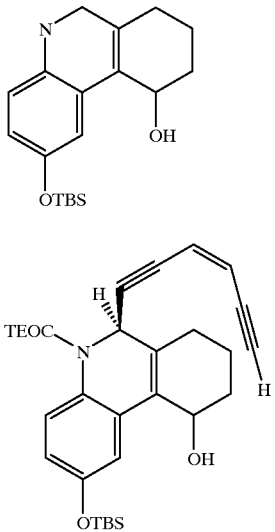

A

B

Enediyne B

To a solution of diTMS enediyne (1.51 mmol, 0.335 g) in THF (7 ml) was added LiOH.H$_2$O (7.9 mmol, 0.33 g) and H$_2$O (1 ml). The solution was stirred for 3 h at room temperature to effect the deprotection. Any residual solid was then dissolved with H$_2$O (5 ml), pentane (2 ml) was added and the solution was washed with brine (5 ml). The organic layer was separated, dried (MgSO$_4$) and was filtered through a small silica plug washing sparingly with pentane.

To this solution was added THF (10 ml), phenanthroline and a stirbar. The solution was cooled to −78° C., and BuLi was added until the indicator turned and then the designated amount of BuLi (2.7 mmol, 1.08 ml) was then added. After stirring for 30 min., a freshly prepared solution of MgBr$_2$ (7.25 mmol, 1.34 g) in THF (20 ml) and benzene (5 ml) was added and the reaction was stirred at −78° C. for 30 min. To the siloxy alcohol A (shown above; 0.091 mmol, 0.030 g) was added THF (3 ml) and to this solution was added dropwise the previously prepared solution of enediyne as described above. After stirring for 30 min., TEOC—Cl (0.45 mmol, 0.081 ml) was then added and the solution was stirred at −78° C. for 2 h. The reaction was quenched with sat. NH$_4$Cl (50 ml) and was extracted with Et$_2$O (50 ml). The ether extracts were dried over Na$_2$SO$_4$, decanted and the solvents were removed in vacuo. Column chromatography (SiO$_2$ 5:1 Hexanes/EtOAc) yielded the enediyne B as a yellow oil (6.4 mg, 13%).

$^1$H NMR (CDCl$_3$) d 7.4 (br s, 1H), 7.08 (d, 1H, J=2.7 Hz), 6.66 (dd, 1H, J=2.7 Hz, 8.7 Hz), 5.92 (d, 1H, J=11.0 Hz), 5.80 (d, 1H, J=11.0 Hz), 5.29 (s, 1H), 4.25 (m, 1H), 4.1 (m, 2H), 3.3 (s, 1H), 1.6–2.2 (m, 6H), 1.0 (buried t, 2H), 0.98 (s, 9H), 0.20 (s, 3H), 0.19 (s, 3H), 0.0 (s, 9H).

Biological Results

The enediyne quinone imine 6 has been synthesized by oxidation of an intermediate hydroisoquinoline. The quinone imine shows dienophilicity with respect to an isobenzofuran. In addition, the quinone imine exhibits potent cytotoxicity against human cancer cell lines as well as the ability to cleave DNA in a single- and double-stranded fashion in the presence of reducing agents.

Discussion

The enediyne quinone imine 6 was synthesized by oxidation of an intermediate hydroisoquinoline, and is dienophilic with respect to an isobenzofuran. In addition, the quinone imine exhibits potent cytotoxicity against human cancer cell lines as well as the ability to cleave DNA in a single and double stranded fashion in the presence of reducing agents.

Figure 1:
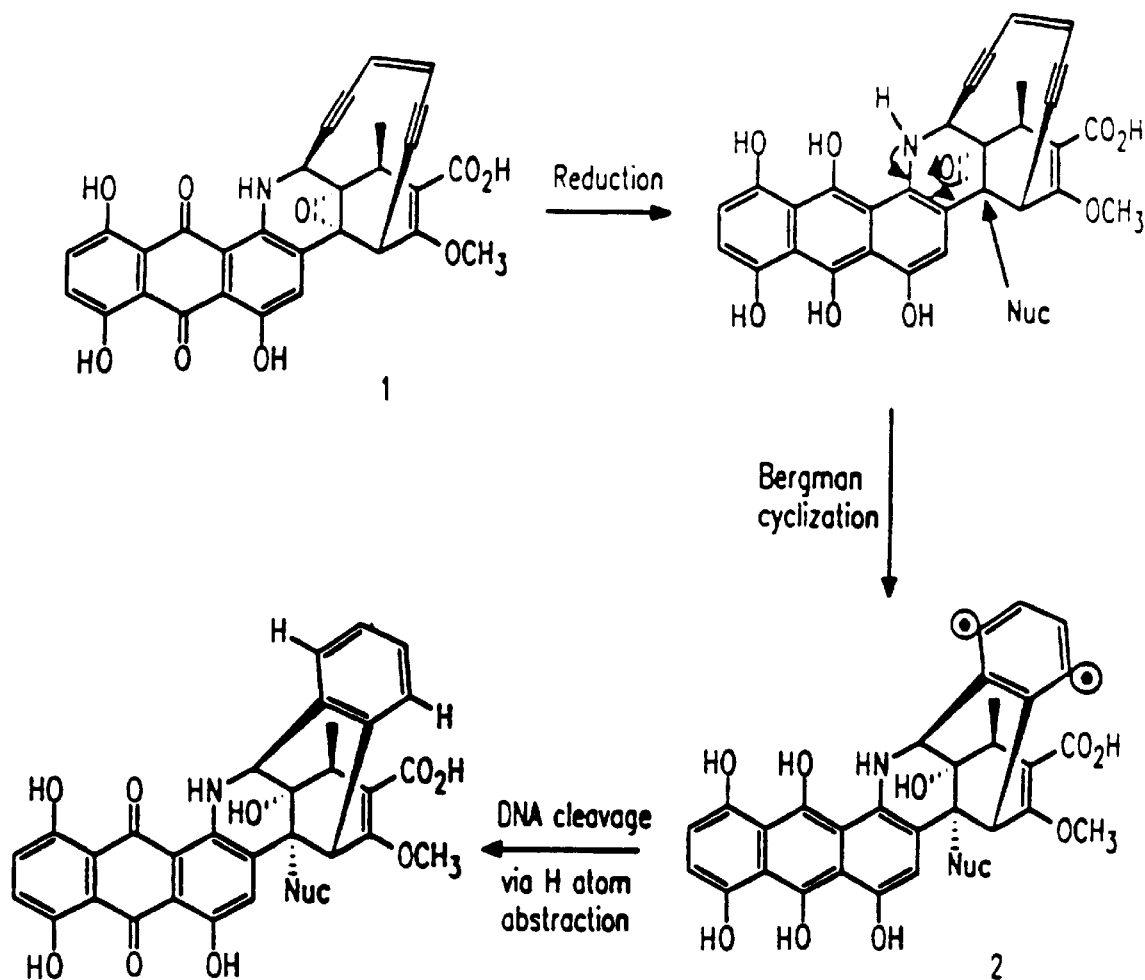
FIG. 1 illustrates the proposed mode of action of enediyne antibiotic dynemicin A.
Figure 2:
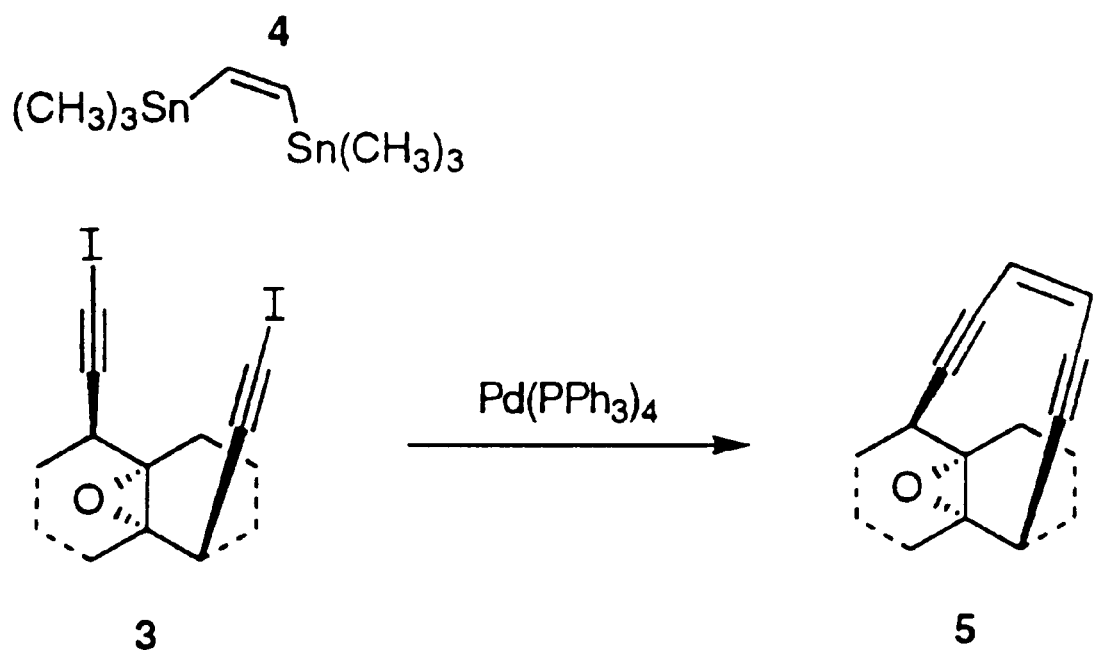
FIG. 2 illustrates the cross-coupling of diiodoalkynes with cis-distannylethylenes to form cyclic enediynes.

The synthesis of intermediates generalized as 5 (FIG. 2) by cross coupling of diiodoalkynes (cf 3) to cis-distannylethylenes (cf 4) mediated by tetrakis(triphenyl-phosphine)palladium(0) has been described. Yoon, T.; Shair, M.D.; Danishefsky, S.J.; Schulte, G. K. *J. Org. Chem.*, 1994, 59, 3752; Shair, M. D.; Yoon, T.; Danishefsky, S. J. *J. Org. Chem.*, 1994, 59, 3755.

Figure 3:
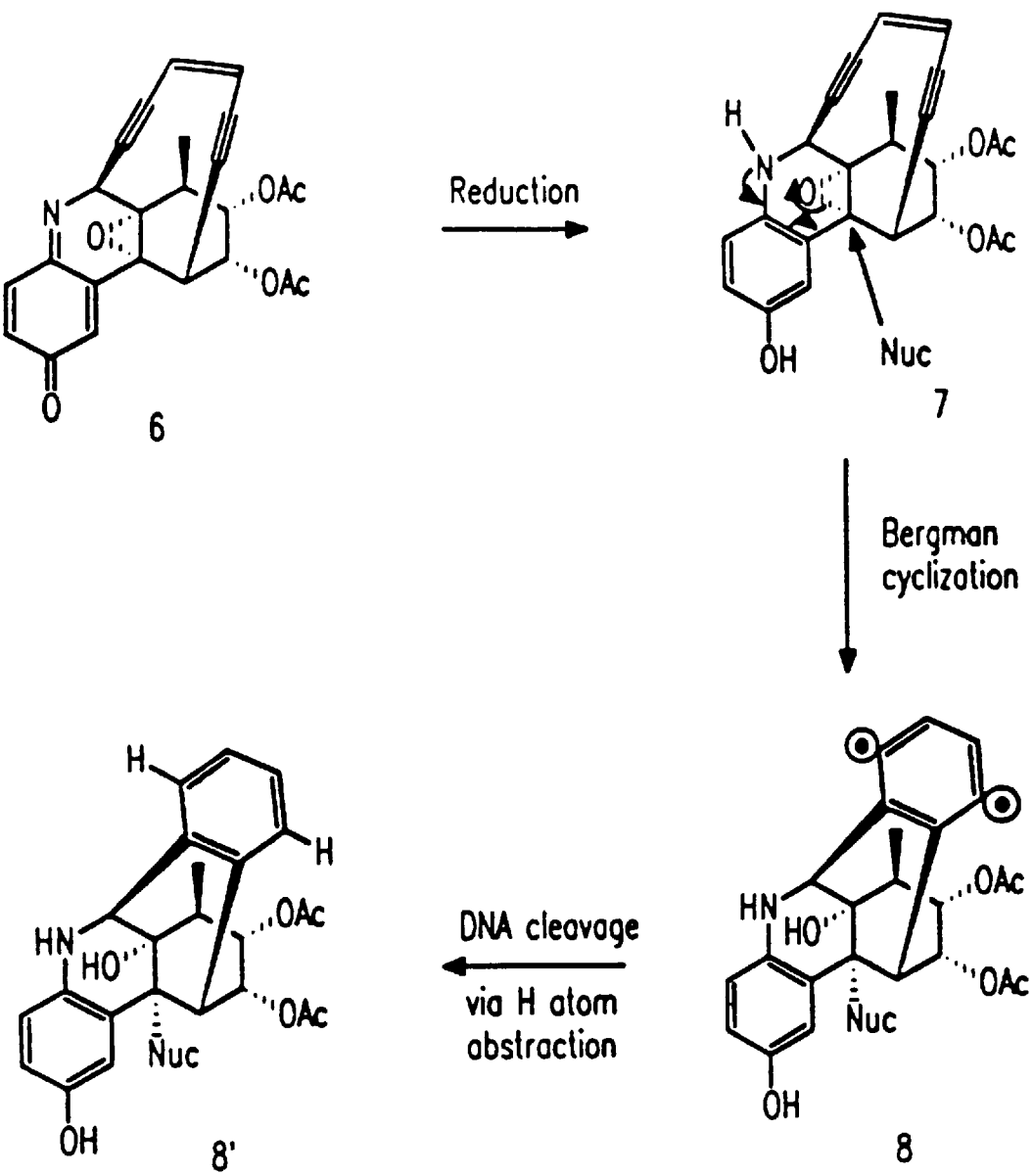
FIG. 3 illustrates the proposed mode of action of quinone imine enediyne 6.

This capability has been applied to the synthesis of quinone imines of the type 6 (FIG. 3). The intent was that such structures might suffer reductive activation to set off the dynemicin-like cascade (cf. 6→7→8). Compound 6 would be accessed by oxidation of a transient hydro-isoquinoline precursor such as 7. Since a system such as 7 is likely to be vulnerable to epoxide opening (and to subsequent 1,4-diyl formation), it must be generated under mild conditions from a readily deprotectable carbamate precursor. Favorable preliminary results in deprotecting TEOC (Me$_3$Si (CH$_2$)$_2$OCO) carbamates of unstable amines recommended it as a protecting group for 7.

Hitchcock, S. A.; Boyer, S. H.; Chu-Moyer, M. Y.; Olson, S. H.; Danishefsky, S. J. *Ancew. Chem. Int. Ed. Encl.*, 1994, 33, 858; Kim, G. et al. *J. Am. Chem. Soc.*, 1990, 112, 2003.

The TEOC group could not be used from the start since it would be necessary to desilylate at several stages along the way while the urethan would remain intact. Accordingly, the allyloxycarbonyl urethan 9 (Yoon, T.; Shair, M. D.; Danishefsky, S. J.; Schulte, G. K. *J. Orc. Chem.*, 1994, 59, 3752; Yoon, T. Ph.D. Thesis, Yale University, 1994) was used, as shown (FIG. 4(b)). Following the protocol of Yoon, et al. (Yoon, T.; Shair, M. D.; Danishefsky, S. J.; Schulte, G. K. *J. Org. Chem.*, 1994, 59, 3752; Shair, M.D.; Yoon, T.; Danishefsky, S. J. *J. Org. Chem.*, 1994, 59, 3755), compound 9 was converted to 10. Since the present method later requires a palladium-mediated cross-coupling reaction, the allyl carbamate was cleaved at the stage of 10 and a TEOC group installed, as shown in 11. Kunz, H.; Unverzagt, C.

Angew. Chem, Int. Ed. Enql., 1984, 23, 436. Diyne 11 was converted to 12 as shown in FIG. 4. After acylation, the two silicon-based deprotections were accomplished with TBAF. Rapid oxidation of the resultant fleeting intermediate 7 with PhI(OAc)$_2$ furnished quinone imine 6. The conversion of 7→6 is apparently the first example of a chemical reaction on such an epoxy enediyne where the nitrogen is not conjugated to a carbonyl group. Also, diol 12 was converted to ketone 14 and then, in sequence, to vinylogous carbamate 15 (FIG. 5). Once again, de-protection of the carbamate by de-silylation led to 16 which was rapidly oxidized, as disclosed hereinabove, to 17.

Practical routes to both dynemicin and analogues thereof required examination of the dienophilicity of the quinone imine linkage in the context of the bridging enediyne linkage (FIG. 6). The dienophilicity concept was tested in a dynemicin analogue prepared from quinone imine 6 and isobenzofuran 17a. (The isobenzofuran 17a was generated in situ as required: Warrener, R. N. *J. Ora. Chem.*, 1971, 93, 2346; Priestly, G. M.; Warrener, R. N. *Tetrahedron Lett.*, 1972, 4295.) Cycloaddition occurred at 0° in methylene chloride to furnish an 86% yield of two products formulated as 18 and 19 in a ratio of 2.5:1. (The 2.5:1 ratio obtained in this cycloaddition appears to arise from an endo:exo selection rather than a facial selectivity issue. It is reasonable but unproven that cycloaddition occurs on the face opposite to the enediyne.) Compound 6 manifests broad cytotoxicity against a variety of tumor cell lines with an IC$_{50}$ ca 5×10$^{-4}$ μM (see Table 1). Its potency is considerably greater than that of the widely used drug mitomycin C. For instance, with human promyelytic leukemia cell line (HL-60) its potency relative to mitomycin C (MMC) as measured by relative IC50 values is ca. 83:1. In acute lymphoblastic T cells (CCRF-CEM), the ratio is ca. 280:1. In corresponding comparisons with m-AMSA with the same lines, it is 70 and 400 times as potent, respectively. (m-AMSA (4'-(9-acridinylamino)methanesulfon-m-anisidide) is a known DNA topoisomerase II inhibitor: Osheroff, N.; Corbett, A. H.; Robinson, M. J. *Biochemistry*, 1993, 32, 3638.)

TABLE 1

Cytotoxicity of 6 versus mitomycin C (MMC) and m-AMSA.

| Compound | IC$_{50}$ (μM) | Cell Line |
|---|---|---|
| quinone imine 6 | 0.00058 | Human promyelocytic leukemic cell (HL-60) |
| mitomycin C | 0.0484 | |
| m-AMSA | 0.0388 | |
| quinone imine 6 | 0.0005 | Human acute lymphoblastic T cells (CCRF-CEM) |
| mitomycin C | 0.140 | |
| m-AMSA | 0.199 | |

The properties of compound 6 as a DNA damaging agent have been examined using PBR$_{322}$ DNA (see FIG. 7). Reductive activation with NADPH and DTT were compared, the former method being more effective. In the nicking assay, compound 6 also outperformed MMC. Compound 6 at higher concentrations (500 μM) exhibited significant amounts of linearization under activation by NADPH. Given the lack of an apparent intercalating arm, the double-stranded cleavage is noteworthy.

In Vivo Effects of Quinone Imine Diyne 6

In a preliminary examination, compound 6 showed unusually high tumor reduction in several mouse models. Compound 6 (0.1–0.5 mg/kg; i.p. (QDx5) reduced tumor volume by 42–63% in mice bearing B-16 melanoma or sarcoma 180. In each case compared, compound 6 outperformed mitomycin C in reducing tumor mass. It is likely that the anti-tumor effects observed arise from a diyl intermediate (cf. 8).

TABLE 2

Comparison of cytotoxic effects of enediyne quinone imine-6 (EQI-6), mitomycin C end amsacrine in various human and animal cell lines[a]

| | Human Leukemic Cells | | | | Human Solid Tumor Cells | | Hamster Lung Cells | |
|---|---|---|---|---|---|---|---|---|
| | | | | | 833K | | DC-3F/ADII | |
| Compound | HL60 | CCRF/CEM | CCRF/VBL (MDR/pg-p) | CCRF/VM-1 (MDR/TopoII) | SK-Br-3 (Breast) | (Testicular) | DC-3F | (MDR/Actinomycin D) |
| EQI-6 | 0.0058 | 0.0005 | 0.0019 | 0.0019 | 0.034 | 0.007 | 0.0018 | 0.0059 |
| Mitomycin | 0.048 | 0.140 | 0.566 | 0.216 | 0.993 | 0.318 | 0.081 | 0.113 |
| m-AMSA | 0.039 | 0.199 | 0.565 | 1.714 | 0.551 | 0.043 | 0.0088 | 0.071 |

[a]HL60, human promyelocytic leukemic cells; CCRF/CEM, human lymphoblastic cells; CCRF/vBL100, CCRF/CEM cells resistance to vinblastine (59-fold) and showed multiple drug resistance with expression of membrane p-glycoprotein; CCRF/VM-1, CCRF/CEM cells resistance to VM-26 (50-fold) and showed multiple drug resistance due to mutations in DNA-topoisomerase II gene; SK-Br-3, human breast adenocarcinoma cells; 833K, human testicular teratocarcinoma cells;DC-3F, Chinese hamster lung cells; DC-3F/ADII, DC-3F cells resistance actinomycin D (32-fold) and showed p-glycoprotein multi-drug resistance. The values given are the concentrations required to inhibit cell growth by 50% (IC$_{50}$) in μM.

Table 2 shows that EQI-6 is far more potent than mitomycin C and m-MSA in all 8 cell lines tested. EQI-6 at low concentrations remains sensitive to multiple drug resistance (MDR) tested, for both MDR due to expression of p-glycoprotein or due to mutation to DNA topoisomerase II gene. Furthermore, EQI-6 is active against both leukemic and solid tumor human cell lines.

TABLE 3

Cytotoxic Effects of EQI-6 and Mitomycin C

Cytotoxic Concentration in $\mu M$

| | Human Promyelocytic leukemic cell (HL-60) | | | Human Acute Lymphoblastic T cell (CCRF-CEM) | | | CCRF-CEM Resistant to Vinblastine (CCRF-CEM/VBL) | | | CCRF-CEM Resistant to VP-16 (CCRF-CEM/VM-1) | | |
|---|---|---|---|---|---|---|---|---|---|---|---|---|
| Cmpd | $IC_{50}$ | $IC_{90}$ | $IC_{95}$ | $IC_{50}$ | $IC_{90}$ | $IC_{95}$ | $IC_{50}$ | $IC_{90}$ | $IC_{95}$ | $IC_{50}$ | $IC_{90}$ | $IC_{95}$ |
| EQI-6 | 0.0058 (1) | 0.0026 (1) | 0.0044 (1) | 0.0005 (1) | 0.0022 (1) | 0.0037 (1) | 0.0189 (1) | 0.0062 (1) | 0.0093 (1) | 0.0019 (1) | 0.0089 (1) | 0.0151 (1) |
| Mitomycin C | 0.0484 (83.4×) | 0.197 (75.8×) | 0.319 (72.5×) | 0.140 (280×) | 0.364 (165×) | 0.503 (136×) | 0.566 (299.5×) | 2.33 (375.8×) | 3.77 (405.4×) | 0.216 (113.7×) | 0.895 (45.5×) | 1.373 (90.9×) |
| m-AMSA | 0.0388 (66.9) | 0.176 (67.7×) | 0.294 (66.8×) | 0.199 (398×) | 1.545 (702×) | 3.101 (838×) | 0.565 (298.9×) | 2.455 (396×) | 4.045 (434.9×) | 1.714 (902.1×) | 3.572 (401.3×) | 4.586 (303.7×) |

TABLE 4

Cytotoxic Effects of EQI-6 and Mitomycin C

Cytotoxic Concentration in $\mu M$

| | Human Breast Adenocarcinoma cells SK-Br-3 | | | Human Testicular Cells (833k) | | | Chinese Hamster Lung Cell (DC-3F) | | | Chinese Hamster Lung Cells Resistant to Actinomycin D (DC-3F/ADII) | | |
|---|---|---|---|---|---|---|---|---|---|---|---|---|
| Compound | $IC_{50}$ | $IC_{90}$ | $IC_{95}$ | $IC_{50}$ | $IC_{90}$ | $IC_{95}$ | $IC_{50}$ | $IC_{90}$ | $IC_{95}$ | $IC_{50}$ | $IC_{90}$ | $IC_{95}$ |
| EQI-6 | 0.034 (1) | 0.187 (1) | 0.332 (1) | 0.007 (1) | 0.025 (1) | 0.039 (1) | 0.0018 (1) | 0.011 (1) | 0.0199 (1) | 0.0059 (1) | 0.0154 (1) | 0.0214 (1) |
| Mitomycin C | 0.993 (29.2×) | 21.8 (16.6×) | 62.3 (187.7×) | 0.318 (45.4×) | 1.53 (61.2×) | 2.61 (66.9×) | 0.0812 (45.1×) | 0.374 (34×) | 0.629 (31.6×) | 0.113 (92.2×) | 0.380 (24.7×) | 0.575 (26.9×) |
| m-AMSA | 0.551 (16.2×) | 84.1 (449.7×) | 464.7 (139.7×) | 0.043 (6.14×) | 0.189 (7.56×) | 0.311 (7.97×) | 0.0088 (4.9×) | 0.053 (4.8×) | 0.0975 (4.9×) | 0.0707 (12×) | 0.8248 (53.6×) | 1.902 (88.9×) |

TABLE 5

Antitumor activity of quinone imine 6 against solid tumors in $BD_2F_1$ mice[a]

| | | B-16 MELANOMA | | SARCOMA 180 | |
|---|---|---|---|---|---|
| COMPOUND | DOSE (mg/kg) | AWC[b] (g) | AVE TUMOR VOLUME (T/C) | AWC (g) | AVE TUMOR VOLUME (T/C) |
| CONTROL | 0 | +0.1 | 1.00 | +0.1 | 1.00 |
| IQ-6 | 0.1 | −1.1 | 0.716 | −0.9 | 0.439 |
|  | 0.5 | +0.1 | 0.537 | −1.1 | 0.226 |
|  | 5.0* | −2.7[c] | 0.063 | −2.1[c] | 0.073 |

[a]Tumor (2 × 10⁶ cells) was inoculated s.c. Treatment started day 4, QD × 5, i.p.; control had nine mice, and each dose two mice; tumor size was evaluated on Day 7 after the beginning of treatment.

[b]AWC: Average body weight change.

[c]One of two mice died on day 5 after treatment.

*QD × 2, i.p.

TABLE 6

Antitumor Activity of Mitomycin against Solid Tumors in B6D2F Mice[a]

| | | SARCOMA 180 | | MELANOMA B-16 | |
|---|---|---|---|---|---|
| COMPOUND | DOSE (mg/kg) | AWC (g) | AVE TUMOR VOLUME (T/C) | AWC (g) | AVE TUMOR VOLUME (T/C) |
| CONTROL | 0 | −1.2 | 1.00 | +2.7 | 1.00 |
| Mit c | 0.2 | −0.5 | 0.845 | −1.9 | 0.952 |
|  | 0.5 | −2.3 | 0.625 | −0.9 | 0.756 |
|  | 2.0 | −1.4 | 0.188 | +0.4 | 0.143 |

[a]Tumor (2 × 10⁶ cells) was inoculated s.c. Treatment started day 4, I.P., QD × 5; control had 3 mice, and each dose had 3 mice; Tumor size was evaluated on day 7 after the beginning of treatment.

[b]AWC: Average weight change.

TABLE 7

Anticancer activity of enediyne quinone imine 6 in BDF mice bearing Lewis lung adenocarcinoma[a]

| Compound | Dose (mg/kg) | AWC[b] (g) Day 7 | Day 10 | Day 14 | Average Tumor Volume (T/C) Day 7 | Day 10 | Day 14 |
|---|---|---|---|---|---|---|---|
| Control | 0 | −1.0 | −0.1 | +0.5 | 1.0 | 1.0 | 1.0 |
| EQI-6 | 0.2 | −2.3 | −0.2 | +0.3 | 1.184 | 0.899 | 0.814 |
|  | 0.4 | −2.3 | −1.6 | −0.5 | 0.414 | 0.521 | 0.456 |
|  | 0.8 | −3.2 | −1.5 | +0.1 | 0.345 | 0.266 | 0.213 |
| Mit C | 0.4 | −1.8 | −1.2 | +0.6 | 0.490 | 0.411 | 0.515 |
|  | 0.8 | −2.2 | −1.8 | +0.2 | 0.356 | 0.363 | 0.437 |
|  | 2.0[c] | −2.7 | — | — | 0.169 | — | — |

[a]Tumor (4 × 10^6 cells) was inoculated S.C. Treatment started on day 4, I.P., QDX5. Control had 4 mice and each dose had 3 mice. Tumor sizes were evaluated on day 7, day 10 and day 14 after beginning of treatment.
[b]AWC: Average body weight change
[c]All of three mice died on day 8 or day 9.

Tables 5–7 showed that EQI-6 markedly inhibited solid tumor growth in tumor bearing mice. At 0.5 mg/kg i.p. QDx5, B-16 melanoma and sarcoma were inhibited 46.3% and 77.4%, respectively. Whereas, the same dose of mitomycin C inhibited 24.6% and 37.5%, respectively (Tables 5 and 6). For Lewis lung adenocarcinoma (Table 7), 0.8 mg/kg i.p. QDx5 of EQI-6 and mitomycin C inhibited the tumor 79.3% and 56.3%, respectively, at day 14 after the treatments. Although EQI-6 is far more potent than mitomycin C in vitro, the in vivo toxicity of EQI-6 is slightly more potent than mitomycin C. Therapeutic efficacy in mice for both appeared similar. EQI-6 appeared very toxic to mice at 5.0 mg/kg QDx5 i.p.; accordingly more frequent administration at lower doses is preferred.

TABLE 8

Cytotoxicity of enediynes as assayed by growth inhibition

| Compound | IC$_{50}$ ($\mu$M) in cell lines |  |  |  |  |
|---|---|---|---|---|---|
|  | HL-60 | MT-2 | MT-4 | 833K | SKBr-3 |
| EQI-7 | 0.012 | 0.015 | 0.0035 | 0.015 | 0.015 |
| EQI-6 | 0.007 | ND | ND | ND | ND |
| Mitomycin c | 0.08 | 0.10 | 0.15 | 0.30 | 0.30 |

Cells were platted on day 1, drug was added on day 2, and XTT assays (for HL-60, MT-2, MT-4 leukemic cells) or SRB assays (for 833K and SK-Br-3 solid tumor cells) were carried out on day 5.

EQI-7 and EQI-6 are both very potent in inhibiting tumor cell growth, and are much more potent than mitomycin C in five different cell lines.

TABLE 9

Single Drug Effect in the HL 60 Cell Line; XTT Assay.

| Compound | Concentration | O.D. (72 h) | Fa | Parameters |
|---|---|---|---|---|
|  | $\mu$M | 450–630 nm |  |  |
| EQI-8 | 0.05 | 1.7535 | 0.1049 |  |
|  | 0.025 | 1.91 | 0.0250 |  |
|  | 0.01 | 1.9535 | 0.0028 | Dm 0.124 $\mu$M |
|  | 0.005 | 1.975 |  | m 2.323 |
|  | 0.0025 | 1.971 |  | r 0.9996 |
|  | 0 | 1.959 |  |  |

TABLE 9-continued

Single Drug Effect in the HL 60 Cell Line; XTT Assay.

| Compound | Concentration | O.D. (72 h) | Fa | Parameters |
|---|---|---|---|---|
| EQI-7 | 0.10 | 0.062 | 0.9617 |  |
|  | 0.05 | 0.118 | 0.9271 | Dm |
|  |  |  |  | 0.019 $\mu$M; |
|  |  |  |  | 0.012 $\mu$M |
|  | 0.025 | 0.644 | 0.6019 | m 2.145 |
|  | 0.01 | 1.358 | 0.1606 | r 0.9921 |
|  | 0.005 | 1.526 | 0.0567 |  |
|  | 0 | 1.6178 |  |  |
| EQI-6 |  |  |  | Dm = 0.0006$\mu$ M, 0.007 $\mu$M |
| Mitomicin C |  |  |  | Dm = 0.048 $\mu$M |

TABLE 10

Single Drug Effect in the DC-3F 60 Cell Line; SRB Assay

| Compound | Concentration | O.D. (72 h) | Fa | Parameters |
|---|---|---|---|---|
|  | $\mu$M | 450–630 nm |  |  |
| EQI-8 | 0.05 | 0.1205 | .09308 |  |
|  | 0.025 | 0.586 | 0.6682 |  |
|  | 0.01 | 1.24 | 0.2978 | Dm 0.0125 $\mu$M |
|  | 0.005 | 1.4215 | 0.1951 | m 1.456 |
|  | 0.0025 | 1.615 | 0.0855 | r 0.9815 |
|  | 0.00 | 1.706 | 0.034 |  |
|  | 0 | 1.766 |  |  |
| EQI-7 | 0.01 | 0.053 | 0.9703 |  |
|  | 0.005 | 0.202 | 0.8868 |  |
|  | 0.0025 | 0.521 | 0.708 | Dm 0.0015 |
|  | 0.001 | 1.392 | 0.2199 | m 1.733 |
|  | 0.00 | 1.5415 | 0.1361 | r 0.9927 |
| EQI-6 |  |  |  | Dm 0.001 $\mu$M |
| Mitomycin C |  |  |  | Dm 0.059 $\mu$M |

TABLE 11

Anticancer Activity of EQI-7 and Mitomycin C in B6D2F1 Mice Bearing Lewis Lung Adenocarcinoma[a]

| Compound | Dose (mg/kg) | AWC[b] (g) Day 7 | AWC[b] (g) Day 10 | Avg Tumor Vol (T/C) Day 7 | Avg Tumor Vol (T/C) Day 10 |
|---|---|---|---|---|---|
| Control | 0 | +0.4 | +1.0 | 1.000 | 1.000 |
| EQI-7 | 0.5[c] | −1.2 | −1.7 | 0.426 | 0.504 |
|  | 1.0[d] | −3.9 | −4.8 | 0.159 | 0.183 |
|  | 1.5[e] | −4.8 | −4.0 | 0.114 | 0.254 |
|  | 3.0[f] |  |  |  |  |
| Mitomycin C | 0.5 | −1.5 | −0.1 | 0.530 | 0.712 |
|  | 1.0 | −0.8 | −0.9 | 0.380 | 0.451 |
|  | 1.5 | −1.5 | −1.3 | 0.340 | 0.402 |
|  | 2.0[g] | −1.8 | 1.6 | 0.286 | 0.485 |

[a]Tumor (2.5 × 10E6 cells) was inoculated S.C. on day (−3). Treatment started on day 1, I.P., Q.D.X5. Control had 6 mice and each dose had 5 mice. Tumor size was evaluated on day 7, day 10 and day 14.
[b]AWC: Average Weight Change.
[c]One of 5 mice died on day 13.
[d]4 of 5 mice died on day 11, 11, 12 and 12.
[e]5 mice died on day 6, 8, 8, 9 and 11.
[f]5 mice died on day 5, 5, 6, 6 and 6.
[g]One of 5 mice died on day 7.

TABLE 12

Antitumor Activity of EQI-6 and Mitomycin C against Sarcoma 180 in B6D2F1 Mice

| Compound | Mice | Dose (mg/kg) | Day 7 AWC[b] (g) | Day 7 Avg Tumor Volume (T/C) | Day 14 AWC (g) | Day 14 Avg Tumor Volume (T/C) |
|---|---|---|---|---|---|---|
| Control | 8 | 0 | +0.1 | 1.000[c] | +0.8 | 1.000[c] |
| EQI-6 | 6 | 0.15 | −0.8 | 0.614 | +0.3 | 0.550 |
|  | 6 | 0.2 | −1.5 | 0.301 | −0.9 | 0.261 |
|  | 6 | 0.3 | −2.2 | 0.189 | −1.1 | 0.124 |
| Mit. C | 6 | 0.15 | −0.6 | 0.650 | +0.2 | 0.814 |
|  | 6 | 0.2 | +0.8 | 0.538 | −0.6 | 0.485 |
|  | 6 | 0.3 | −1.8 | 0.249 | −1.0 | 0.394 |

[a]Tumor (3 × 10⁶ cells) was inoculated S.C. on day −3. Antitumor treatment started on day 1, b.i.d.X5, IP.
[b]AWC: Average weight change.
[c]The control tumor volumes for day 7 and day 14 were 0.111 cm³ and 0.607 cm³, respectively.

TABLE 13

Cytotoxic Effect of Dynemycin A Analogue EQI-6 and Mitomycin C.

Cytotoxic Concentration in μM

| Compound | Human Breast Adenocarcinoma Cells (SK-Br-3) $IC_{50}$ | $IC_{90}$ | $IC_{95}$ | Chinese Hamster Lung Cells (DC-3F) $IC_{50}$ | $IC_{90}$ | $IC_{95}$ | Chinese Hamster Lung Cells Resistant to Mitomycin D (DC-3F/ADII) $IC_{50}$ | $IC_{90}$ | $IC_{95}$ |
|---|---|---|---|---|---|---|---|---|---|
| EQI-6 | 0.039 | 1.11 | 3.47 | 0.001 | 0.002 | 0.003 | 0.001 | 0.004 | 0.005 |
| MITOMYCIN C | 2.336 | 62.93 | 192.89 | 0.059 | 0.166 | 0.235 | 0.074 | 0.264 | 0.406 |
| m-AMSA |  |  |  | 0.004 | 0.017 | 0.028 | 0.033 | 0.18 | 0.321 |

TABLE 14

Cytotoxic Effect of Dynemycin A Analogue EQI-6 and Mitomycin C.

| | Cytotoxic Concentration in $\mu$M | | | | | | | | |
|---|---|---|---|---|---|---|---|---|---|
| | Human Acute Lymphoblastic T Cells (CCRF-CEM) | | | CCRF-CEM Cells Resistance to Vinblastine (CCRF-DEM/VLB$_{100}$) | | | CCRF-CEM-Cells Resistant to VM-1 (CCRF-CEM/VM-1) | | |
| Compound | IC$_{50}$ | IC$_{90}$ | IC$_{95}$ | IC$_{50}$ | IC$_{90}$ | IC$_{95}$ | IC$_{50}$ | IC$_{90}$ | IC$_{95}$ |
| EQI-6 | 0.003 | 0.008 | 0.013 | 0.006 | 0.014 | 0.019 | 0.008 | 0.024 | 0.036 |
| MITOMYICN C | 0.096 | 0.37 | 0.584 | 0.917 | 2.399 | 3.327 | 0.113 | 0.675 | 1.239 |
| m-AMSA | 0.129 | 0.755 | 1.378 | 0.964 | 7.233 | 14.353 | 4.047 | 10.966 | 15.391 |

TABLE 15

Cytotoxic Effect of Dynemycin A Analogue EQI-6 and Mitomycin C.

| | Cytotoxic Concentration in $\mu$M | | | | | | | | | | | |
|---|---|---|---|---|---|---|---|---|---|---|---|---|
| | MT$_4$ Cells | | | Leukemia Cells MT$_2$ CEells | | | HUMAN Promyelocytic (HL-60) | | | Human Testicular Cells (833K) | | |
| Compound | IC$_{50}$ | IC$_{90}$ | IC$_{95}$ | IC$_{50}$ | IC$_{90}$ | IC$_{95}$ | IC$_{50}$ | IC$_{90}$ | IC$_{95}$ | IC$_{50}$ | IC$_{90}$ | IC$_{95}$ |
| EQI-6 | 0.001 | 0.005 | 0.01 | 0.003 | 0.012 | 0.018 | 0.005 | 0.011 | 0.014 | 0.005 | 0.040 | 0.082 |
| Mito-mycin C | 0.115 | 0.253 | 0.331 | 0.169 | 0.398 | 0.532 | 0.051 | 0.167 | 0.25 | 0.394 | 2.286 | 4.155 |
| m-AMSA | | | | 0.019 | 0.038 | 0.048 | | | | | | |

What is claimed is:

1. A method of inhibiting growth of tumor cells which comprises contacting the tumor cells with a compound having the structure:

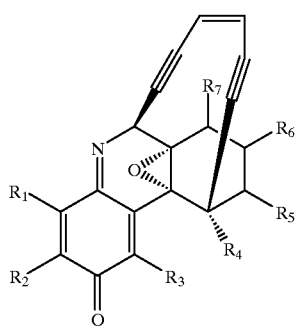

wherein $R_1$, $R_2$ and $R_3$ are H, $R_4$ is H, OH, or OCOCH$_3$; wherein $R_5$ is H, or OCOCH$_3$; wherein $R_6$ is H, or CO$_2$H; and wherein $R_7$, is H or CH$_3$.

2. A method of inhibiting growth of tumor cells which comprises contacting the tumor cells with a compound having the structure:

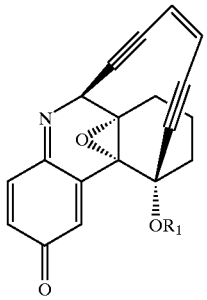

wherein $R_1$ is H, or COCH$_3$.

3. The method of claim 1, wherein $R_5$ is OCOCH$_3$, $R_6$ is CO$_2$H; and $R_7$ is CH$_3$.

4. The method of claim 1 or 2, wherein the tumor cells are selected from the group consisting of colon adenocarcinoma, ovarian carcinoma, human melanoma, colon cancer, human bladder tumor, human breast carcinoma.

5. The method of claim 1 or 2, wherein the tumor cells are multi-drug resistant.

6. The method of claim 2, wherein $R_1$ is H.

* * * * *

UNITED STATES PATENT AND TRADEMARK OFFICE
CERTIFICATE OF CORRECTION

| | | |
|---|---|---|
| PATENT NO. | : 6,020,341 | Page 1 of 1 |
| APPLICATION NO. | : 08/849658 | |
| DATED | : February 1, 2000 | |
| INVENTOR(S) | : Samuel Danishefsky | |

It is certified that error appears in the above-identified patent and that said Letters Patent is hereby corrected as shown below:

In The Specification

In column 1, beginning at line 11 and ending at line 15, please delete:

"The invention described herein was made in the course of work under Grant Number CA28824 from the National Institutes of Health, U.S. Department of Health and Human Services. The U.S. Government may have certain rights in this invention."

and insert:

--This invention was made with government support under grant number CA028824 awarded by the National Institutes of Health. The government has certain rights in the invention.--

Signed and Sealed this
Twenty-ninth Day of March, 2016

Michelle K. Lee
*Director of the United States Patent and Trademark Office*